(12) United States Patent
Beckman et al.

(10) Patent No.: US 12,403,159 B2
(45) Date of Patent: Sep. 2, 2025

(54) THERAPEUTIC METAL COMPLEXES AND LIGANDS AND METHODS OF MAKING AND USING THE SAME

(71) Applicant: Oregon State University, Corvallis, OR (US)

(72) Inventors: Joseph Beckman, Corvallis, OR (US); James Hurst, Beaverton, OR (US); John Sirois, Corvallis, OR (US); Chris Beaudry, Corvallis, OR (US)

(73) Assignee: Oregon State University, Corvallis, OR (US)

( * ) Notice: Subject to any disclaimer, the term of this patent is extended or adjusted under 35 U.S.C. 154(b) by 0 days.

(21) Appl. No.: 18/102,474

(22) Filed: Jan. 27, 2023

(65) Prior Publication Data

US 2023/0172977 A1    Jun. 8, 2023

Related U.S. Application Data

(60) Division of application No. 16/802,410, filed on Feb. 26, 2020, now Pat. No. 11,596,651, which is a continuation of application No. PCT/US2018/049163, filed on Aug. 31, 2018.

(60) Provisional application No. 62/553,714, filed on Sep. 1, 2017.

(51) Int. Cl.
| | | |
|---|---|---|
| *A61K 33/34* | (2006.01) | |
| *A61K 31/155* | (2006.01) | |
| *A61K 31/4545* | (2006.01) | |
| *A61K 45/06* | (2006.01) | |
| *C07F 1/08* | (2006.01) | |

(52) U.S. Cl.
CPC ............ *A61K 33/34* (2013.01); *A61K 31/155* (2013.01); *A61K 31/4545* (2013.01); *A61K 45/06* (2013.01); *C07F 1/08* (2013.01)

(58) Field of Classification Search
None
See application file for complete search history.

(56) References Cited

U.S. PATENT DOCUMENTS

| 4,107,210 A | 8/1978 | Freiter |
|---|---|---|
| 2012/0270850 A1 | 10/2012 | Barnham et al. |

FOREIGN PATENT DOCUMENTS

| CA | 2166676 | 7/1996 | | |
|---|---|---|---|---|
| JP | 2012-511513 A | 5/2012 | | |
| JP | 2016-540828 A | 12/2016 | | |
| NL | 7403524 A | 3/1974 | | |
| WO | WO 2008/025941 | 3/2008 | | |
| WO | WO 2008/061306 | 5/2008 | | |
| WO | WO 2010/066010 | 6/2010 | | |
| WO | WO/2015/070177 | * | 5/2014 | ............ A61K 31/55 |
| WO | WO 2017/070752 | 5/2017 | | |
| WO | WO 2017/214546 | 12/2017 | | |
| WO | WO 2018/204564 | 11/2018 | | |

OTHER PUBLICATIONS

Trist et al (Acta Neuropathol 135:155-156, 2018) (Year: 2018).*
Hall et al (Arch Pharm Pharm Med Chem 333:217-225, 2000) (Year: 2000).*
Forsyth et al (Ann Neurol 41:722-730, 1997) (Year: 1997).*
STN Accession No. 1975:78476 (Year: 1975).*
STN Accession No. 1979:213592 (Year: 1979).*
STN Accession No. 1976:38573 (Year: 1976).*
STN Accession No. 1997:675201 (Year: 1997).*
Alsop et al., Investigations into some aryl substituted bis(thiosemicarbazones) and their copper complexes, *Inorganica Chimica Acta*, vol. 358(9), pp. 2770-2780, Apr. 12, 2005.
Basken et al., "Elucidation of the Human Serum Albumin (HSA) Binding Site for the Cu-PTSM and Cu-ATSM Radiopharmaceuticals," *Pharmacokinetics, Pharmacodynamics and Drug Metabolism*, 98(6): 2170-2179, Oct. 20, 2008.
CAS Registry No. 1207290-67-2, entry date Feb. 24, 2010.
CAS Registry No. 53557-00-9, entry date Nov. 16, 1984.
CAS Registry No. 68341-03-07, entered Nov. 16, 1984.
Chinese Office action for related Chinese Application No. 201880065301.9, dated Oct. 28, 2022 (*with English-language translation of Search Report and summary pages*).
Coats et al., "Comparative analysis of the cytotoxicity of substituted [Phenylglyoxal bis(4-methyl-3-thiosemicarbazone)]copper(II) chelates," *Journal of Medicinal Chemistry*, 19(1): 131-136, Jan. 1, 1976.
Coats et al., "Comparative analysis of the cytotoxicity of substituted [Phenylglyoxal bis(4-methyl-3-thiosemicarbazone)]copper(II) chelates. 2. Parabolic correlations and their implications for selective toxicity," *Journal of Medicinal Chemistry*, 21(8): 804-809, Aug. 1, 1978.
Cowley et al., Bifunctional chelators for copper radiopharmaceuticals: the synthesis of [Cu(ATSM)-amino acid] and [Cu(ATSM)-octreotide] conjugates, *Dalton Transactions*, vol. 2, pp. 209-217, Nov. 14, 2006.
Dearling et al., "Copper bis(thiosemicarbazone) complexes as hypoxia imaging agents: structure-activity relationships," *J Biol Inorg Chem*, vol. 7, pp. 249-259, Sep. 8, 2001.
Dearling et al., "Redox-active metal complexes for imaging hypoxic tissues: structure-activity relationships in copper(II) bis(thiosemicarbazone) complexes," *Chem Commun.*, No. 22, pp. 2531-2532, 1998.
Dearling et al., "Some thoughts on the mechanism of cellular trapping of Cu(II)-ATSM," *Nuclear Medicine and Biology*, 37(3): 237-243, Jan. 15, 2010.

(Continued)

*Primary Examiner* — Craig D Ricci
(74) *Attorney, Agent, or Firm* — Klarquist Sparkman, LLP

(57) ABSTRACT

Disclosed herein are compound embodiments that are useful for treating a variety of diseases, particularly neurological diseases, motor neuron diseases, copper deficiency-related diseases, and/or mitochondrial deficiencies. The compound embodiments described herein also can be used in PET methods. Also disclosed herein are embodiments of methods of making and using the compound embodiments, as well as pharmaceutical formulations comprising the disclosed compound embodiments.

15 Claims, 7 Drawing Sheets

(56) References Cited

OTHER PUBLICATIONS

Durackova et al., "Thiohydrazone copper(II) complexes. The relationship between redox properties and superoxide dismutase mimetic activity," *Bioelectrochemistry and Bioenergetics*, 48(1): 109-116, Feb. 1999.
Examination Report issued for AU Application No. 2018325283 on Nov. 25, 2022.
Hall et al., The Cytotoxicity of Symmetrical and Unsymmetrical Bis(thiosemicarbazones) and Their Metal Complexes in Murine and Human Tumor Cells, *Arch Pharm*, 333(7): 217-225, Jul. 12, 2000.
Hickey et al., Intracellular Distribution of Fluorescent Copper and Zinc Bis(thiosemicarbazonato) Complexes Measured with Fluorescence Lifetime Spectroscopy, *Inorganic Chemistry*, vol. 54(19), pp. 9556-9567, Sep. 23, 2015.
Hilton et al., "$Cu^{II}$(atsm) improves the neurological phenotype and survival of $SOD1^{G93A}$ mice and selectively increases enzymatically active SOD1 in the spinal cord," *Scientific Reports*, Article No. 42292, Feb. 13, 2017.
International Search Report and Written Opinion issued for International Application No. PCT/US2018/049163 on Nov. 20, 2018.
Japanese Office Action for related Japanese Patent Application No. 2020-512506, dated Oct. 11, 2022 (*with English-language machine translation*).
John et al., "Structure-Activity Relationships for Metal-Labeled Blood Flow Tracers: Comparison of Keto Aldehyde Bis(thiosemicarbazonato)copper(II) Derivatives," *J. Med. Chem.*, 33(6): 1764-1770, Jun. 1, 1990.
Lim et al., "Copper and zinc bis(thiosemicarbazonato) complexes with a fluorescent tag: synthesis, radiolabelling with copper-64, cell uptake and fluorescence studies," *J Biol Inorg Chem*, vol. 15, pp. 225-235, Sep. 22, 2009.
McAllum et al., "ZNII (atsm) is protective in amyotrophic lateral sclerosis model mice via a copper delivery mechanism," vol. 81, pp. 20-24, *Neurobiology of Disease*, Mar. 10, 2015.
Minkel et al., "Structure-function correlations in the reaction of bis(thiosemicarbonazato) Copper (II) complexes," *Cancer Research*, vol. 38, pp. 124-129, Jan. 1978.
Soon et al., "Diacetylbis(N(4)-methylthiosemicarbazonato) Copper(II) ($Cu^{II}$(atsm)) Protects against Peroxynitrite-induced Nitrosative Damage and Prolongs Survival in Amyotrophic Lateral Sclerosis Mouse Model," *J. Biol. Chem.*, 286(51): 44035-44044, Dec. 23, 2011.
Vieira et al., "CuATSM efficacy is independently replicated in a SOD1 mouse model of ALS while unmetallated ATSM therapy fails to reveal benefits," *IBRO Reports*, vol. 7, pp. 47-53, Mar. 12, 2017.
Wada et al., "Cu-ATSM, an Intracellular-Accessible Superoxide Dismutase (SOD)-Like Copper Complex: Evaluation in an Ischemia-Reperfursion Injury Model," *Biol. Pharm. Bull.*, 17(5): 701-704, May 1994.
Warren et al., "The mass spectra of some copper(II) complexes related to anti-carcinogens," *Organic Mass Spectrometry*, 5(15): 15-18, Jan. 1971.
Williams et al., "Copper delivery to the CNS by CuATSM effectively treats motor neuron disease in SODG93A mice co-expressing the Copper-Chaperone-for-SOD," *Neurobiology of Disease*, vol. 89, 9 pages, Jan. 27, 2016.
Yokoyama et al., Development of Neutral and Bifunctional Radiopharmaceuticals Using $^{62}$Cu-Dithiosemicarbazone DTS) Chelate-Basic Studies on 64Cu chelates- , *Radioisotopes*, vol. 35(5), pp. 249-255 (*with English-language abstract*), May 1, 1986.
Gummerus et al., "Condensation products of some alpha-diketones especially 3-methyl-2-hydroxy-2-cyclopentenone with thiosemicarbazide," *Commentaliones Hysico Mathematicae*, 32(5): 1966. (Abstract only).
Beraldo et al., "Copper(II) and nickel(II) complexes of the bis{N(3)-substituted thiosemicarbazones} of phenylglyoxal and 1-phenylpropane-1,2-dione," *Transition Met. Chem.*, vol. 22, pp. 459-464, Sep. 1997.
Sirois et al., "Oxidative release of copper from pharmacologic copper bis(thiosemicarbazonato) compounds," *Inorg. Chem.*, vol. 57, pp. 8923-8932, Jul. 6, 2018.
Examination Report issued for European Application No. 18778677.7 issued on Mar. 15, 2023.

* cited by examiner

THERAPEUTIC METAL COMPLEXES AND LIGANDS AND METHODS OF MAKING AND USING THE SAME

CROSS REFERENCE TO RELATED APPLICATION

This application is a divisional of U.S. application Ser. No. 16/802,410, filed on Feb. 26, 2020, which is a continuation of International Application No. PCT/US2018/049163, filed on Aug. 31, 2018, which claims the benefit of the earlier filing date of U.S. Provisional Patent Application No. 62/553,714, filed on Sep. 1, 2017; each of these prior applications is incorporated herein by reference in its entirety.

ACKNOWLEDGMENT OF GOVERNMENT SUPPORT

This invention was made with government support under Contract No. W81XWH-15-1-0289, awarded by the Department of Defense. The government has certain rights in the invention.

FIELD

The present disclosure concerns embodiments of a therapeutic compound, particularly therapeutics capable of treating neurological diseases, as well as embodiments of a method for making and using such compound embodiments.

BACKGROUND

Amyotrophic lateral sclerosis (ALS) is estimated to affect 30,000 Americans and over 400,000 people worldwide at any given time. Approximately 5000 Americans receive the diagnosis each year. The disease causes the unrelenting death of motor neurons, resulting in a progressive paralysis that kills its victims within one to five years on average. Only two agents have been approved for treating ALS by the FDA, and both solely slow disease progression in a subset of patients and extend life at best by a few months. In addition, many common breeds of dogs, including Corgis, German Shepherds and Rhodesian Ridgebacks, frequently carry a homozygous mutation in the SOD gene. Between 6-12 years of age, these dogs develop canine degenerative myelopathy, a progressive disease that affects motor neurons with many similarities to human illness.

A need exists in the art for therapeutics that can reproducibly treat ALS and other neurological and/or copper deficiency-related diseases.

SUMMARY

Disclosed herein are embodiments of a compound having a structure satisfying Formula I

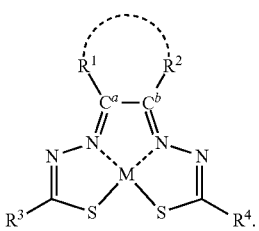

Formula I

In yet additional embodiments, the compound can have a structure satisfying other formulas described herein. Variables illustrated above in Formula I are described herein.

Also disclosed herein are embodiments of a pharmaceutical formulation, comprising a compound having a structure satisfying any one or more of the formulas described herein and a dosage form. In some embodiments of the pharmaceutical formulation, only a small amount, if any, of the compound crystalizes when combined with the pharmaceutical dosage form.

Also described herein are embodiments of a method, comprising administering to a subject or a sample a therapeutic amount of a compound as described herein. In particular disclosed embodiments, a method for treating a motor neuron disease is disclosed, wherein the method comprises administering to a subject a therapeutic amount of a compound described herein. In some embodiments, the motor neuron disease is selected from ALS, Lou Gehrig's disease, primary lateral sclerosis, Kennedy's syndrome, frontal temporal dementia associated with ALS, spinal muscular atrophy, or any combination thereof.

Also disclosed herein are embodiments of a method, comprising administering a compound as described herein, wherein the metal component of the compound is an isotope of the metal, to a subject or a sample. In particular disclosed embodiments, the isotope can be $^{60}Cu^{2+}$, $^{61}Cu^{2+}$, $^{62}Cu^{2+}$, $^{63}Cu^{2+}$, $^{64}Cu^{2+}$, or $^{65}Cu^{2+}$. In some embodiments, the method can further comprise imaging the subject or the sample using positron emission tomography to determine the presence of a motor neuron disease.

The foregoing and other objects, features, and advantages of the present disclosure will become more apparent from the following detailed description, which proceeds with reference to the accompanying figures.

DETAILED DESCRIPTION

I. Overview of Terms

Figure 1:
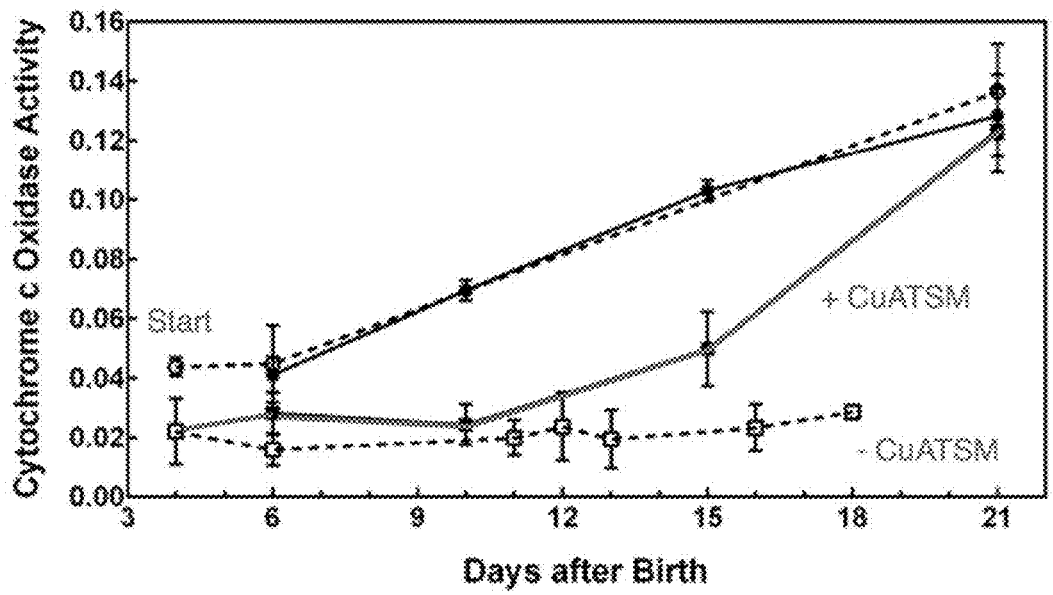
FIG. 1 is a graph of cytochrome c oxidase activity in mouse brains, wherein the line labeled with the symbol "○" represents untreated CCS only mice; the line labeled with "•" represents CuATSM-treated CCS mice; the line labeled with "☐" represents untreated CCS×SOD mice; and the line labeled with "■" represents CuATSM-treated CCS×SOD mice.

The following explanations of terms are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. The term "or" refers to a single element of stated alternative elements or a combination of two or more elements, unless the context clearly indicates otherwise.

Although the steps of some of the disclosed methods are described in a particular, sequential order for convenient presentation, it should be understood that this manner of description encompasses rearrangement, unless a particular ordering is required by specific language set forth below. For example, steps described sequentially may in some cases be rearranged or performed concurrently. Additionally, the description sometimes uses terms like "produce" and "provide" to describe the disclosed methods. These terms are high-level abstractions of the actual steps that are performed. The actual steps that correspond to these terms will vary depending on the particular implementation and are readily discernible by one of ordinary skill in the art. Unless explained otherwise, all technical and scientific terms used herein have the same meaning as commonly understood to one of ordinary skill in the art to which this disclosure belongs. Although methods and compounds similar or equivalent to those described herein can be used in the practice or testing of the present disclosure, suitable methods and compounds are described below. The compounds, methods, and examples are illustrative only and not intended to be limiting, unless otherwise indicated. Other features of the disclosure are apparent from the following detailed description and the claims.

Unless otherwise indicated, all numbers expressing quantities of components, molecular weights, percentages, temperatures, times, and so forth, as used in the specification or claims are to be understood as being modified by the term "about." Accordingly, unless otherwise indicated, implicitly or explicitly, the numerical parameters set forth are approximations that can depend on the desired properties sought and/or limits of detection under standard test conditions/methods. When directly and explicitly distinguishing embodiments from discussed prior art, the embodiment numbers are not approximates unless the word "about" is recited. Furthermore, not all alternatives recited herein are equivalents.

Compound embodiments disclosed herein may contain one or more asymmetric elements such as stereogenic centers, stereogenic axes and the like, e.g., asymmetric carbon atoms, so that the chemical conjugates can exist in different stereoisomeric forms. These compound embodiments can be, for example, racemates or optically active forms. For compound embodiments with two or more asymmetric elements, these compound embodiments can additionally be mixtures of diastereomers. For compound embodiments having asymmetric centers, all optical isomers in pure form and mixtures thereof are encompassed by corresponding generic formulas unless context clearly indicates otherwise or an express statement excluding an isomer is provided. In these situations, the single enantiomers, i.e., optically active forms can be obtained by method known to a person of ordinary skill in the art, such as asymmetric synthesis, synthesis from optically pure precursors, or by resolution of the racemates. Resolution of the racemates can also be accomplished, for example, by conventional methods, such as crystallization in the presence of a resolving agent, or chromatography, using, for example a chiral HPLC column. All isomeric forms are contemplated herein regardless of the methods used to obtain them.

All forms (for example solvates, optical isomers, enantiomeric forms, polymorphs, free compound and salts) of an active agent may be employed either alone or in combination.

Stereochemical definitions and conventions used herein generally follow S. P. Parker, Ed., McGraw-Hill *Dictionary of Chemical Terms* (1984) McGraw-Hill Book Company, New York; and Eliel, E. and Wilen, S., *Stereochemistry of Organic Compounds* (1994) John Wiley & Sons, Inc., New York. Many organic compounds exist in optically active forms, i.e., they have the ability to rotate the plane of plane-polarized light. In describing an optically active compound, the prefixes (+/−) D and L or R and S are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory To facilitate review of the various embodiments of the disclosure, the following explanations of specific terms and abbreviations are provided:

Adjuvant: An excipient that modifies the effect of other agents, typically the active ingredient. Adjuvants are often pharmacological and/or immunological agents. An adjuvant may modify the effect of an active ingredient by increasing a desired neurological response, such as an immune response. An adjuvant may also act as a stabilizing agent for a formulation. Exemplary adjuvants include, but are not limited to, aluminum hydroxide, alum, aluminum phosphate, killed bacteria, squalene, detergents, cytokines, paraffin oil, and combination adjuvants, such as Freund's complete adjuvant or Freund's incomplete adjuvant.

Aldehyde: —C(O)H.

Aliphatic: A hydrocarbon group having at least one carbon atom to 50 carbon atoms ($C_{1-50}$, such as one to 25 carbon atoms ($C_{1-25}$), or one to ten carbon atoms ($C_{1-10}$), and which includes alkanes (or alkyl), alkenes (or alkenyl), alkynes (or alkynyl), including cyclic versions thereof, and further including straight- and branched-chain arrangements, and all stereo and position isomers as well.

Aliphatic-aryl: An aryl group that is or can be coupled to a compound disclosed herein, wherein the aryl group is or becomes coupled through an aliphatic group.

Aliphatic-heteroaryl: A heteroaryl group that is or can be coupled to a compound disclosed herein, wherein the heteroaryl group is or becomes coupled through an aliphatic group.

Alkenyl: An unsaturated monovalent hydrocarbon having at least two carbon atom to 50 carbon atoms ($C_{2-50}$), such as two to 25 carbon atoms ($C_{2-25}$), or two to ten carbon atoms ($C_{2-10}$), and at least one carbon-carbon double bond, wherein the unsaturated monovalent hydrocarbon can be derived from removing one hydrogen atom from one carbon atom of a parent alkene. An alkenyl group can be branched, straight-chain, cyclic (e.g., cycloalkenyl), cis, or trans (e.g., E or 4.

Alkoxy: —O-aliphatic (such as —O-alkyl), with exemplary embodiments including, but not limited to, methoxy, ethoxy, n-propoxy, isopropoxy, n-butoxy, t-butoxy, sec-butoxy, n-pentoxy.

Alkyl: A saturated monovalent hydrocarbon having at least one carbon atom to 50 carbon atoms ($C_{1-50}$), such as one to 25 carbon atoms ($C_{1-25}$), or one to ten carbon atoms ($C_{1-10}$), wherein the saturated monovalent hydrocarbon can be derived from removing one hydrogen atom from one carbon atom of a parent compound (e.g., alkane). An alkyl group can be branched, straight-chain, or cyclic (e.g., cycloalkyl).

Alkylaryl/Alkenylaryl/Alkynylaryl: An aryl group that is or can be coupled to a compound disclosed herein, wherein the aryl group is or becomes coupled through an alkyl, alkenyl, or alkynyl group, respectively.

Alkylheteroaryl/Alkenylheteroaryl/Alkynylheteroaryl: A heteroaryl group that is or can be coupled to a compound disclosed herein, wherein the heteroaryl group is or becomes coupled through an alkyl, alkenyl, or alkynyl group, respectively.

Alkynyl: An unsaturated monovalent hydrocarbon having at least two carbon atom to 50 carbon atoms ($C_{2-50}$, such as two to 25 carbon atoms ($C_{2-25}$), or two to ten carbon atoms ($C_{2-10}$), and at least one carbon-carbon triple bond, wherein the unsaturated monovalent hydrocarbon can be derived from removing one hydrogen atom from one carbon atom of a parent alkyne. An alkynyl group can be branched, straight-chain, or cyclic (e.g., cycloalkynyl).

Amide: —C(O)NR$^a$R$^b$ wherein each of R$^a$ and R$^b$ independently is selected from hydrogen, aliphatic, heteroaliphatic, aryl, heteroaryl, or any combination thereof.

Amine: —NR$^a$R$^b$, wherein each of R$^a$ and R$^b$ independently is selected from hydrogen, aliphatic, aryl, heteroaliphatic, heteroaryl, and any combination thereof. In some embodiments, R$^a$ and R$^b$ can join together to form, with the nitrogen atom to which they are bound, a heterocyclic ring.

Aromatic: A cyclic, conjugated group or moiety of, unless specified otherwise, from 5 to 15 ring atoms having a single ring (e.g., phenyl, pyridinyl, or pyrazolyl) or multiple condensed rings in which at least one ring is aromatic (e.g., naphthyl, indolyl, or pyrazolopyridinyl); that is, at least one ring, and optionally multiple condensed rings, have a continuous, delocalized π-electron system. Typically, the number of out of plane π-electrons corresponds to the Hückel rule (4n+2). The point of attachment to the parent structure typically is through an aromatic portion of the condensed ring system. For example,

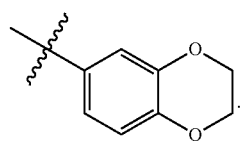 [SMILES: *c1ccc2c(c1)OCCO2]

However, in certain examples, context or express disclosure may indicate that the point of attachment is through a non-aromatic portion of the condensed ring system. For example,

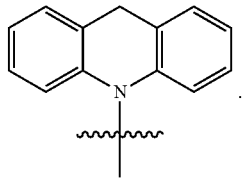 [SMILES: *N1c2ccccc2Cc2ccccc21]

An aromatic group or moiety may comprise only carbon atoms in the ring, such as in an aryl group or moiety, or it may comprise one or more ring carbon atoms and one or more ring heteroatoms comprising a lone pair of electrons (e.g. S, O, N, P, or Si), such as in a heteroaryl group or moiety.

Aryl: An aromatic carbocyclic group comprising at least five carbon atoms to 15 carbon atoms ($C_5$-$C_{15}$), such as five to ten carbon atoms ($C_5$-$C_{10}$), having a single ring or multiple condensed rings, which condensed rings can or may not be aromatic provided that the point of attachment to a remaining position of the compounds disclosed herein is through an atom of the aromatic carbocyclic group. Aryl groups may be substituted with one or more groups other than hydrogen, such as aliphatic, heteroaliphatic, aryl, heteroaryl, other functional groups, or any combination thereof.

Carboxyl: —C(O)OR$^a$, wherein R$^a$ hydrogen, aliphatic, aromatic, aliphatic-aromatic, heteroaliphatic-aromatic, heteroaliphatic, and any combination thereof.

Carrier: An excipient that serves as a component capable of delivering a compound described herein. In some embodiments, a carrier can be a suspension aid, solubilizing aid, or aerosolization aid. In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. In some examples, the pharmaceutically acceptable carrier may be sterile to be suitable for administration to a subject (for example, by parenteral, intramuscular, or subcutaneous injection). In addition to biologically-neutral carriers, pharmaceutical formulations to be administered can contain minor amounts of non-toxic auxiliary substances, such as wetting or emulsifying agents, preservatives, and pH buffering agents and the like, for example sodium acetate or sorbitan monolaurate.

Haloaliphatic: An aliphatic group wherein one or more hydrogen atoms, such as one to 10 hydrogen atoms, independently is replaced with a halogen atom, such as fluoro, bromo, chloro, or iodo.

Haloaliphatic-aryl: An aryl group that is or can be coupled to a compound disclosed herein, wherein the aryl group is or becomes coupled through a haloaliphatic group.

Haloaliphatic-heteroaryl: A heteroaryl group that is or can be coupled to a compound disclosed herein, wherein the heteroaryl group is or becomes coupled through a haloaliphatic group.

Haloalkyl/Haloalkenyl/Haloalkynyl: An alkyl, alkenyl, or alkynyl group (which can be branched, straight-chain, or cyclic) comprising at least one halogen atom to 20 halogen atoms, such as one to 15 halogen atoms, or one to 5 halogen atoms, which can be selected from, but not limited to bromine, chlorine, fluorine, or iodine.

Heteroaliphatic: An aliphatic group comprising at least one heteroatom to 20 heteroatoms, such as one to 15 heteroatoms, or one to 5 heteroatoms, which can be selected from, but not limited to oxygen, nitrogen, sulfur, selenium, phosphorous, and oxidized forms thereof within the group.

Heteroaliphatic-aryl: An aryl group that is or can be coupled to a compound disclosed herein, wherein the aryl group is or becomes coupled through a heteroaliphatic group.

Heteroalkyl/Heteroalkenyl/Heteroalkynyl: An alkyl, alkenyl, or alkynyl group (which can be branched, straight-chain, or cyclic) comprising at least one heteroatom to 20 heteroatoms, such as one to 15 heteroatoms, or one to 5 heteroatoms, which can be selected from, but not limited to oxygen, nitrogen, sulfur, selenium, phosphorous, and oxidized forms thereof within the group.

Heteroalkyl-aryl/Heteroalkenyl-aryl/Heteroalkynyl-aryl: An aryl group that is or can be coupled to a compound disclosed herein, wherein the aryl group is or becomes coupled through a heteroalkyl, heteroalkenyl, or heteroalkynyl group, respectively.

Heteroalkyl-heteroaryl/Heteroalkenyl-heteroaryl/Heteroalkynyl-heteroaryl: A heteroaryl group that is or can be coupled to a compound disclosed herein, wherein the aryl group is or becomes coupled through a heteroalkyl, heteroalkenyl, or heteroalkynyl group, respectively.

Heteroaryl: An aryl group comprising at least one heteroatom to six heteroatoms, such as one to four heteroatoms, which can be selected from, but not limited to oxygen, nitrogen, sulfur, selenium, phosphorous, and oxidized forms thereof within the ring. Such heteroaryl groups can have a single ring or multiple condensed rings, wherein the condensed rings may or may not be aromatic and/or contain a heteroatom, provided that the point of attachment is through an atom of the aromatic heteroaryl group. Heteroaryl groups may be substituted with one or more groups other than hydrogen, such as aliphatic, heteroaliphatic, aryl, heteroaryl, other functional groups, or any combination thereof.

Imidoester: —$C(NH_2^+)OR^a$, wherein $R^a$ is selected from aliphatic, aromatic, aliphatic-aromatic, heteroaliphatic-aromatic, heteroaliphatic, and any combination thereof.

Ketone: —$C(O)R^a$, wherein $R^a$ is selected from aliphatic, aromatic, aliphatic-aromatic, heteroaliphatic-aromatic, heteroaliphatic, and any combination thereof.

Motor Neuron Disease: In some embodiments, the term is used to refer to a group of diseases that affect the nerves in the brain and spinal cord and that can lead to muscle weakness, often with visible wasting symptoms. In some embodiments and in some countries, the term "motor neuron disease" can be used to designate a particular disease and can be synonymous with amyotrophic lateral sclerosis.

Pharmaceutically Acceptable Excipient: A substance, other than an active ingredient (e.g., a compound described herein), that is included in a formulation of the active ingredient. As used herein, an excipient may be incorporated within particles of a pharmaceutical formulation, or it may be physically mixed with particles of a pharmaceutical formulation. An excipient also can be in the form of a solution, suspension, emulsion, or the like. An excipient can be used, for example, to dilute an active agent and/or to modify properties of a pharmaceutical formulation. Excipients can include, but are not limited to, antiadherents, binders, coatings, enteric coatings, disintegrants, flavorings, sweeteners, colorants, lubricants, glidants, sorbents, preservatives, adjuvants, carriers or vehicles. Excipients may be starches and modified starches, cellulose and cellulose derivatives, saccharides and their derivatives such as disaccharides, polysaccharides and sugar alcohols, protein, synthetic polymers, crosslinked polymers, antioxidants, amino acids or preservatives. Exemplary excipients include, but are not limited to, magnesium stearate, stearic acid, vegetable stearin, sucrose, lactose, starches, hydroxypropyl cellulose, hydoxypropyl methylcellulose, xylitol, sorbitol, maltitol, gelatin, polyvinylpyrrolidone (PVP), polyethyleneglycol (PEG), tocopheryl polyethylene glycol 1000 succinate (also known as vitamin E TPGS, or TPGS), carboxy methyl cellulose, dipalmitoyl phosphatidyl choline (DPPC), vitamin A, vitamin E, vitamin C, retinyl palmitate, selenium, cysteine, methionine, citric acid, sodium citrate, methyl paraben, propyl paraben, sugar, silica, talc, magnesium carbonate, sodium starch glycolate, tartrazine, aspartame, benzalkonium chloride, sesame oil, propyl gallate, sodium metabisulphite or lanolin.

Pharmaceutically Acceptable Salt: Pharmaceutically acceptable salts of a compound described herein that are derived from a variety of organic and inorganic counter ions as will be known to a person of ordinary skill in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate, and the like. "Pharmaceutically acceptable acid addition salts" are a subset of "pharmaceutically acceptable salts" that retain the biological effectiveness of the free bases while formed by acid partners. In particular, the disclosed compound embodiments form salts with a variety of pharmaceutically acceptable acids, including, without limitation, inorganic acids such as hydrochloric acid, hydrobromic acid, sulfuric acid, nitric acid, phosphoric acid, and the like, as well as organic acids such as formic acid, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, benzene sulfonic acid, isethionic acid, methanesulfonic acid, ethanesulfonic acid, p-toluenesulfonic acid, salicylic acid, xinafoic acid and the like. "Pharmaceutically acceptable base addition salts" are a subset of "pharmaceutically acceptable salts" that are derived from inorganic bases such as sodium, potassium, lithium, ammonium, calcium, magnesium, iron, zinc, copper, manganese, aluminum salts and the like. Exemplary salts are the ammonium, potassium, sodium, calcium, and magnesium salts. Salts derived from pharmaceutically acceptable organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins, and the like. Exemplary organic bases are isopropylamine, diethylamine, ethanolamine, trimethylamine, dicyclohexylamine, choline, and caffeine. (See, for example, S. M. Berge, et al., "Pharmaceutical Salts," J. Pharm. Sci., 1977; 66:1-19 which is incorporated herein by reference.)

Pharmaceutically/Therapeutically Effective Amount: An amount of a compound sufficient to treat a specified disorder or disease, or to ameliorate or eradicate one or more of its symptoms and/or to prevent the occurrence of the disease or disorder. The amount of a compound which constitutes a "therapeutically effective amount" will vary depending on the compound, the disease state and its severity, the age of the patient to be treated, and the like. The therapeutically effective amount can be determined by a person of ordinary skill in the art.

Prodrug: Compound embodiments disclosed herein that are transformed, most typically in vivo, to yield a biologically active compound, particularly the parent compound, for example, by hydrolysis in the gut or enzymatic conversion. Common examples of prodrug moieties include, but are not limited to, pharmaceutically acceptable ester and amide forms of a compound having an active form bearing a carboxylic acid moiety. Examples of pharmaceutically acceptable esters of the compound embodiments of the present disclosure include, but are not limited to, esters of phosphate groups and carboxylic acids, such as aliphatic esters, particularly alkyl esters (for example $C_{1-6}$ alkyl esters). Other prodrug moieties include phosphate esters, such as $—CH_2—O—P(O)(OR^d)_2$ or a salt thereof, wherein $R^d$ is H or aliphatic (e.g., $C_{1-6}$alkyl). Acceptable esters also include cycloalkyl esters and arylalkyl esters such as, but not limited to, benzyl. Examples of pharmaceutically acceptable amides of the compound embodiments of this disclosure include, but are not limited to, primary amides, and secondary and tertiary alkyl amides (for example with between one and six carbons). Amides and esters of disclosed exemplary embodiments of compound embodiments according to the present disclosure can be prepared according to conventional methods. A thorough discussion of prodrugs is provided in T. Higuchi and V. Stella, "Pro-drugs as Novel Delivery Systems," Vol 14 of the A.C.S. Symposium Series, and in Bioreversible Carriers in Drug Design, ed. Edward B. Roche, American Pharmaceutical Association and Pergamon Press, 1987, both of which are incorporated herein by reference.

Subject: Mammals and other animals, such as humans, companion animals (e.g., dogs, cats, rabbits, etc), utility animals, and feed animals; thus, disclosed methods are applicable to both human therapy and veterinary applications.

Thioketone: $—C(S)R^a$, wherein $R^a$ is selected from aliphatic, aromatic, aliphatic-aromatic, heteroaliphatic-aromatic, heteroaliphatic, and any combination thereof.

Treating/Treatment: Treatment of a disease or condition of interest in a subject, particularly a human or canine having the disease or condition of interest, and includes by way of example, and without limitation:
(i) prophylactic administration to prevent the disease or condition from occurring in a subject, or to ameliorate symptoms associated with the condition if required in particular, when such subject is predisposed to the condition but has not yet been diagnosed as having it;
(ii) inhibiting the disease or condition, for example, arresting or slowing its development;
(iii) relieving the disease or condition, for example, causing regression of the disease or condition or a symptom thereof; or
(iv) stabilizing the disease or condition.

As used herein, the terms "disease" and "condition" can be used interchangeably or can be different in that the particular malady or condition may not have a known causative agent (so that etiology has not yet been determined) and it is therefore not yet recognized as a disease but only as an undesirable condition or syndrome, where a more or less specific set of symptoms have been identified by clinicians.

A person of ordinary skill in the art would recognize that the definitions provided above are not intended to include impermissible substitution patterns (e.g., methyl substituted with five different groups, and the like). Such impermissible substitution patterns are easily recognized by a person of ordinary skill in the art. In formulas and specific compounds disclosed herein, a hydrogen atom is present and completes any formal valency requirements (but may not necessarily be illustrated) wherever a functional group or other atom is not illustrated. For example, a phenyl ring that is drawn as

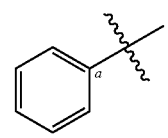 [SMILES: *c1ccccc1]

comprises a hydrogen atom attached to each carbon atom of the phenyl ring other than the "a" carbon, even though such hydrogen atoms are not illustrated.

Any functional group disclosed herein and/or defined above can be substituted or unsubstituted, unless otherwise indicated herein.

II. Introduction

CuATSM has been shown to be protective in the high expressing superoxide dismutase ("SOD") SOD$^{G93A}$ mice by the rigorous criteria established in the art; however, the high copper affinity of CuATSM causes this agent to be an inefficient delivery vehicle to bypass the distribution system that naturally limits copper transport into the central nervous system ("CNS"). Continued treatment with CuATSM may eventually provide sufficient copper for the SOD copper chaperone (referred to as "CCS") to complete the maturation of Cu,Zn SOD; however, CuATSM has many detrimental aspects associated with its use and there is a need in the art for improved therapeutic agents that can treat neurological diseases and/or copper deficiency-related disorders. For example, the rate of copper delivery by CuATSM is slow in vivo. See FIG. 1, which illustrates that CuATSM is slow to deliver copper to the CNS of CCS and CCS×SOD mice. It can take weeks for cytochrome c oxidase and SOD to replenish copper-deficient enzymes in the CNS. The reduction potential of CuATSM is more negative than any common biological reductant. The accepted mechanism of release is that $Cu^{2+}$ in CuATSM is reduced to $Cu^{1+}$, which is more likely to be transferred to intracellular copper carriers. Reduced CuATSM also reduces molecular oxygen to the potentially toxic superoxide radical ($O_2^{-31}$). Fast reoxidation of the CuATSM compound further limits copper release in non-hypoxic tissues as well as producing a damaging species. As a consequence, only a small fraction of copper ions (e.g., $Cu^{2+}$ or $Cu^{1+}$) is slowly released from the CuATSM complex, which limits its acute therapeutic efficacy. Additionally, CuATSM is metabolized by the liver within hours in vivo, which results in removing one of its terminal methyl groups (such as the methyl groups located at the positions illustrated below). Demethylation of CuATSM creates a free amino group that prevents the metabolite's entry into the CNS and favors copper delivery to other targets. Additionally, CuATSM has a much higher affinity for human serum albumin compared to albumins in other non-human animals, such as mice, rats, and dogs, which limits its partitioning into the CNS in human subjects.

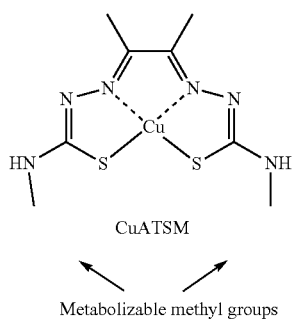

CuATSM

Metabolizable methyl groups

Another limitation is that the ATSM ligand component of the CuATSM complex is pharmacologically active in binding metals and thus can react in potentially undesirable side reactions. For example, ZnATSM (which contains zinc rather than copper) is slightly protective against degeneration in an ALS-SOD mouse model; however, when ZnATSM is applied dermally to mice, the animals experience distress and the compound is ineffective to protect the mice. Also, free ligands such as GTSM and PTSM (both illustrated below) cause a significant delay in growth of juvenile mice

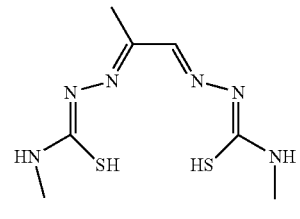

PTSM

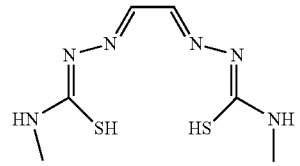

GTSM

CuATSM has a compact symmetric structure, which contributes to another limitation associated with this compound. Its compact structure allows the ATSM ligand component to rapidly form extremely stable crystals, which causes several challenges in making and formulating this compound, hindering its ability to serve as suitable pharmacological agent. For example, the metal-free ATSM ligand component crystallizes within seconds during its synthesis in all common refluxing solvents; thus, it is difficult to subsequently add copper in the final step of the synthesis, particularly at an industrial scale needed to produce the large quantities required for clinical use.

Additionally, the semithiocarbazide side arms of the ATSM ligand have considerable flexibility and readily rotate around the central carbon bond joining the imine methyl groups. This flexibility causes difficulties in using stoichiometric copper to form the final 1:1 complex. Titration of copper into ATSM ligand to form CuATSM does not yield isosbestic behavior, showing the formation of a stoichiometric complex (see FIG. 2, which illustrates that as copper additions approach 1:1, the isosbestic points deviate indicating undesirable nonstoichiometric behavior). Also, mass spectrometry has shown the formation of a complex with an empirical formula consistent with 3 copper atoms and 2 ATSM ligands. The formation of such complexes is problematic as these complexes are difficult to remove. As a consequence, the ATSM must be diluted to minimize the flexible semithiocarbazato groups from producing multimeric complexes of several copper atoms associated with two or more ATSM moieties. Dilute solutions, however are difficult to achieve because of the low solubility of ATSM even under reflux conditions.

Furthermore, CuATSM exhibits a high propensity for crystallization and has a remarkably high melting point of 245° C. This crystallization and high melting point create issues with forming an orally-active CuATSM compound and prevents the use of solid dispersant methods to formulate the complex for oral delivery. As such, producing formulations having appropriate dosage limits of CuATSM remains a limitation in using this compound therapeutically, particularly in view of CuATSM's propensity to gradually crystalize out of matrices and form insoluble crystals. Large amounts of crystallized CuATSM passes into the bowels, and thereby contributes to gastrointestinal distress. Also, the negative potential of the CuATSM makes it very difficult to reduce intracellularly with biological reductants, which is reflected in the slow efficacy in replenishing SOD and COX extending over weeks. As a consequence, most of the CuATSM administered is eliminated in urine with copper still bound.

The compound embodiments described herein address the above-noted limitations of the CuATSM compound. The disclosed compound embodiments exhibit improved formulation characteristics. For example, disclosed embodiments crystallize much less efficiently than CuATSM as crystallization is inhibited in the compound embodiments. Disclosed embodiments also typically have less negative reduction potentials, contributing to their improved ability to release copper in vivo. Compound embodiments disclosed herein also exhibit reduction potentials that allow for easier reduction as compared to CuATSM and thus the disclosed compound embodiments are more effective to deliver copper to areas of a subject, particularly the CNS. The superior features of the disclosed compound embodiments are not limited to those listed above, as is demonstrated by the following disclosure.

III. Compound Embodiments

Disclosed herein are compound embodiments having a structure satisfying Formula I below. While Formula I below is illustrated with a metal species ("M") complexed with the illustrated ligand, the present disclosure contemplates free ligands wherein a metal species has not yet been complexed. When such free ligands are not complexed with a metal species, the free ligands can exist in tautomeric forms, such as is illustrated in Formulas IA and IB below. As such, compound embodiments disclosed herein include metal complexes having structures satisfying Formula I and free ligand components having structures satisfying Formulas IA and IB. Compound embodiments disclosed herein (which include throughout this disclosure either the metal-complexed compounds and/or the free ligand components) can be used as therapeutic compounds, such as to treat neurological diseases and other copper deficiency-related diseases.

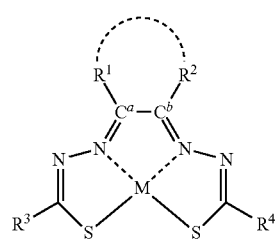

Formula I

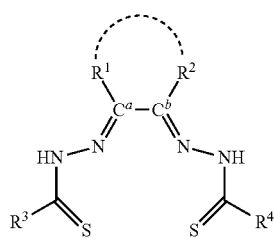

Formula IA

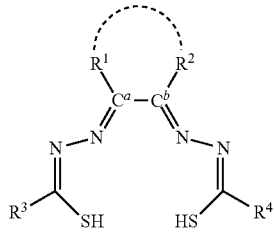

Formula IB

With reference to Formula I, M is a divalent metal or a radioactive isotope thereof. With reference to Formulas I, IA, and IB, the following features can apply:

$R^1$ can be an aliphatic group or an aromatic group, such as an aryl or heteroaryl group, that is directly or indirectly (such as through a linker group) attached to $C^a$;

$R^2$ can be selected from hydrogen, aliphatic, heteroaliphatic, or aromatic (e.g., aryl or heteroaryl), wherein the aromatic group can be directly or indirectly (such as through a linker group) attached to Cb; or $R^1$ and $R^2$ can be bound together form a fused ring system comprising two to seven fused rings; and each of $R^3$ and $R^4$ independently can be selected from —NH$_2$, —NHR, —NRR', —OR, —SR, or —C(R)$_{1-2}$R' wherein each R and R' independently are selected from hydrogen, aliphatic, aryl, heteroaliphatic, aliphatic-aryl, heteroaryl, aliphatic-heteroaryl, heteroaliphatic-aryl, or heteroaliphatic-heteroaryl. In some embodiments, R and R' can, with the nitrogen or carbon atom to which they are bound, form a heterocyclic or a heteroaryl group, or a cyclic aliphatic group; or, when $R^3$ and/or $R^4$ are —C(R)$_1$R', then one of the R or R' groups forms a double bond with the carbon atom and further is joined with the remaining R or R' group to form an aryl group.

In embodiments where $R^1$ and/or $R^2$ are indirectly attached to the respective illustrated imine carbon atom via a linker group, the linker group can be an aliphatic linker, a heteroaliphatic linker, a heteroatom, an aromatic group, or any combination thereof. Exemplary linker groups include, but are not limited to, alkyl, alkynyl, or alkenyl linker groups; polyalkylene glycol linker groups; a heteroatom selected from oxygen, sulfur, or NR (wherein R can be selected from hydrogen, aliphatic, aryl, heteroaliphatic, aliphatic-aryl, heteroaryl, aliphatic-heteroaryl, heteroaliphatic-aryl, or heteroaliphatic-heteroaryl); a carbonyl group; a thioketone group; an amide group; a sulfone group; a sulfoxide group; phenyl; pyridyl; or other suitable linkers.

In some disclosed embodiments, M is copper (e.g., $Cu^{2+}$), iron, palladium, cadmium, manganese, or a radioactive isotope thereof. In yet additional embodiments, M is $Cu^{2+}$, $^{60}Cu^{2+}$, $^{61}Cu^{2+}$, $^{62}Cu^{2+}$, $^{63}Cu^{2+}$, $^{64}Cu^{2+}$, or $^{65}Cu^{2+}$.

In some embodiments, $R^1$ can be selected from phenyl, pyridyl, naphthyl, anthracenyl, quinolinyl, quinazolinyl, quinoxalinyl, benzoquinolinyl, benzoquinoxalinyl, benzoquinazolinyl, or the like. In yet some additional embodiments, $R^1$ can be selected from phenyl-$(R^5)_n$, pyridyl-$(R^5)_n$, naphthyl-$(R^5)_n$, anthracenyl-$(R^5)_n$, quinolinyl-$(R^5)_n$, quinazolinyl-$(R^5)_n$, quinoxalinyl-$(R^5)_n$, benzoquinolinyl-$(R^5)_n$, benzoquinoxalinyl-$(R^5)_n$, benzoquinazolinyl-$(R^5)_n$, wherein each $R^5$ independently is an electron-donating group or an electron-withdrawing group (which can be attached directly or indirectly, such as through an aliphatic or heteroaliphatic linker, to the indicated aromatic group) and n is an integer selected from 1 to 10, such as 1 to 8, or 1 to 6, or 1 to 4. As indicated above, any of these groups listed for $R^1$ can be bound to the remainder of the compound directly or indirectly through a linker as described herein.

In particular disclosed embodiments, each $R^5$ independently can be selected from aliphatic; aryl; haloaliphatic; heteroaliphatic; aliphatic-aryl; heteroaryl; aliphatic-heteroaryl; heteroaliphatic-aryl; heteroaliphatic-heteroaryl; hydroxyl; —$NH_2$; —$P^+(R^d)_3$ or —$N^+(R^d)_3$ (wherein each $R^d$ independently can be selected from hydrogen, aliphatic, aryl, heteroaliphatic, aliphatic-aryl, heteroaryl, aliphatic-heteroaryl, heteroaliphatic-aryl, or heteroaliphatic-heteroaryl); nitro; thiol; halogen; phosphate; phosphoryl; sulfino; sulfo; azide; a linker-X group; or any combination of such groups.

With reference to the above-mentioned "linker-X" group, the linker group can be selected from an aliphatic linker, a heteroaliphatic linker, a heteroatom, or an aromatic group. In particular disclosed embodiments, the linker can be a carbonyl-containing group; an alkylene oxide; an alkyl, alkenyl, or alkynyl group; an imidoester; or other linker groups described herein; or the linker can be generated from a maleimide, a haloacetyl, or a pyridyl disulfide. Also with reference to the "linker-X" group, X is a moiety that includes functional groups suitable to facilitate delivery of the compound to a target. In particular disclosed embodiments, X can be a targeting moiety capable of promoting or facilitating permeation of the compound through a membrane. In some embodiments, the targeting moiety can be a moiety capable of increasing delivery of a compound into the cytosol, such as increasing delivery of the compound by a factor of 10 (as compared to a similar compound that does not comprise a targeting moiety) and/or into mitochondria by a factor of 100 (as compared to a similar compound that does not comprise the targeting moiety). Compound embodiments satisfying these formulas can further comprise a counter ion in embodiments wherein X comprises a charged group, thereby providing electronic neutrality. For example, in some embodiments, each X independently can be selected from a phosphonium group, an ammonium group, or other such group comprising a positively charged moiety. In particular disclosed embodiments, the counter ion used in combination with a hydrophobic, positively charged moiety can be a negatively charged counter ion and typically is a pharmaceutically-acceptable, negatively charged counter ion. Exemplary negatively charged counter ions include, but are not limited to, halogens (e.g., $Br^-$, $Cl^-$, $F^-$, $I^-$), sulfonate (e.g., mesylate), sulfate, hydrobromide, acetate, citrate, maleate, tartrate, phosphate, nitrate, salicylate, fumerate, lactate, or the like.

In particular disclosed embodiments, the linker-X group described herein can be selected from —C(O)$R^c$X, —C[($R^c$)$_2$]$_m$X, —[(CH$_2$)$_2$O]$_m$X, —O(CH$_2$)$_m$X, —[O(CH$_2$)$_2$]$_m$X, —$NR^c$(CH$_2$)$_m$X, —[(CH$_2$)$_2$$NR^c$]$_m$X, —$NR^c$(CH$_2$)$_2$]$_m$X, —C(=$NH_2^+$)$NR^c$X, —CH$_2$C(O)NH$R^c$X, —S$R^c$X, or

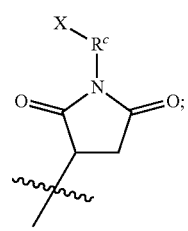

wherein each $R^c$ independently is selected from aliphatic, aryl, heteroaliphatic, aliphatic-aryl, heteroaryl, aliphatic-heteroaryl, heteroaliphatic-aryl, or heteroaliphatic-heteroaryl; each X independently can be selected from —$P^+(R^d)_3$ or —$N^+(R^d)_3$, wherein each $R^d$ independently can be selected from hydrogen, aliphatic, aryl, heteroaliphatic, aliphatic-aryl, heteroaryl, aliphatic-heteroaryl, heteroaliphatic-aryl, or heteroaliphatic-heteroaryl; and each m independently can be an integer selected from 1 to 30, such as 1 to 20, or 1 to 10, or 1 to 5.

In particular disclosed embodiments comprising a linker-X group, the linker-X group can be selected from —C(O)(CH$_2$)$_{1-30}$P$^+$Ph$_3$·Br$^-$, —C(=$NH_2^+$)N(CH$_2$)$_{1-30}$P$^+$Ph$_3$·Br$^-$, —CH$_2$C(O)NH(CH$_2$)$_{1-30}$P$^+$Ph$_3$·Br$^-$, —S(CH$_2$)$_{1-30}$P$^+$Ph$_3$·Br$^-$, —(CH$_2$)$_{1-30}$P$^+$Ph$_3$·Br$^-$, —O(CH$_2$)$_{1-30}$P$^+$Ph$_3$·Br$^-$, —NH(CH$_2$)$_{1-30}$P$^+$Ph$_3$·Br$^-$, —C(O)[O(CH$_2$)$_2$]$_{1-30}$P$^+$Ph$_3$·Br$^-$, —C(=$NH_2^+$)NCH$_2$[O(CH$_2$)$_2$]$_{1-30}$P$^+$Ph$_3$·Br$^-$, —CH$_2$C(O)NH[O(CH$_2$)$_2$]$_{1-30}$P$^+$Ph$_3$·Br$^-$, —[O(CH$_2$)$_2$]$_{1-30}$P$^+$Ph$_3$·Br$^-$, —C(O)(CH$_2$)$_{1-30}$N$^+$Me$_3$·Br$^-$, —C(=$NH_2^+$)N(CH$_2$)$_{1-30}$N$^+$Me$_3$·Br$^-$, —CH$_2$C(O)NH(CH$_2$)$_{1-30}$N$^+$Me$_3$·Br$^-$, —S(CH$_2$)$_{1-30}$N$^+$Me$_3$·Br$^-$, —(CH$_2$)$_{1-30}$N$^+$Me$_3$·Br$^-$, —O(CH$_2$)$_{1-30}$N$^+$Me$_3$·Br$^-$, —NH(CH$_2$)$_{1-30}$N$^+$Me$_3$·Br$^-$, —C(O)[O(CH$_2$)$_2$]$_{1-30}$N$^+$Me$_3$·Br$^-$, —C(=$NH_2^+$)NCH$_2$[O(CH$_2$)$_2$]$_{1-30}$N+Me$_3$·Br$^-$, —CH$_2$C(O)NH[O(CH$_2$)$_2$]$_{1-30}$N+Me$_3$·Br$^-$, —S[O(CH$_2$)$_2$]$_{1-30}$N+Me$_3$·Br$^-$,

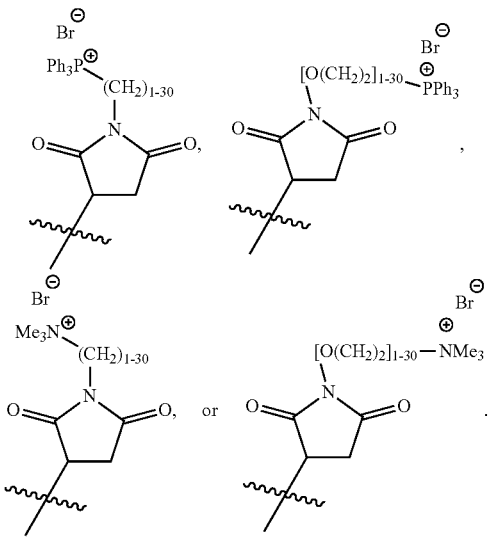

In some embodiments, each $R^5$ independently can be selected from alkyl, alkenyl, alkynyl, amine, carboxylic acid, ester, alkoxy, amide, cyano, ether, haloalkyl, silyl ether, phosphine, thioether, disulfide, isothiocyanate, isocyanate, carbonate, ketone, sulfinyl, sulfonyl, thioketone, isonitrile, or any combination of such groups. In particular disclosed embodiments, n is 1, 2, 3, 4, 5, 6, 7, 8, 9, or 10.

In yet additional embodiments, $R^1$ can be selected from phenyl; —PhC[($R^c$)$_2$]$_m$PPh$_3$; —Ph[(CH$_2$)$_2$O]$_m$PPh$_3$; —Ph[O(CH$_2$)$_2$]$_m$PPh$_3$; —PhOH; —PhOPPh$_3$; —PhNRPPh$_3$; —Ph[(CH$_2$)$_2$NR]$_m$PPh$_3$, or —Ph[NR(CH$_2$)$_2$]$_m$PPh$_3$, wherein R is hydrogen, aliphatic, aryl, heteroaliphatic, aliphatic-aryl, heteroaryl, aliphatic-heteroaryl, heteroaliphatic-aryl, or heteroaliphatic-heteroaryl; —PhO-aliphatic (e.g., —PhOMe, —PhOEt, —PhOPr, —PhOiPr, —PhOnBu, —PhOiBu, —PhOtBu, wherein the OMe, OEt, OPr, or OBu groups are located in the ortho, meta, or para positions of the phenyl ring relative to the position at which the phenyl ring is attached to the remainder of the compound); —PhN(R) aliphatic (e.g., —PhN(R)Me, —PhN(R)Et, —PhN(R)Pr, —PhN(R)iPr, —PhN(R)nBu, —Ph(R)iBu, —PhN(R)tBu, wherein the N(R)Me, N(R)Et, N(R)Pr, or N(R)Bu groups are located in the ortho, meta, or para positions of the phenyl ring relative to the position at which the phenyl ring is attached to the remainder of the compound and wherein R is hydrogen, aliphatic, aryl, heteroaliphatic, aliphatic-aryl, heteroaryl, aliphatic-heteroaryl, heteroaliphatic-aryl, or heteroaliphatic-heteroaryl); or —Ph(Z)$_{1-5}$ (wherein Z is Cl, F, Br, or I, NO$_2$, CF$_3$, C(CF$_3$)$_3$, wherein the halogen atoms and the NO$_2$, CF$_3$, C(CF$_3$)$_3$ groups are located in all positions of the phenyl ring, or may be in the ortho, meta, or para positions of the phenyl ring relative to the position at which the phenyl ring is attached to the remainder of the compound); and n is 1.

In particular disclosed embodiments, $R^1$ is phenyl, -Ph$_p$OMe, -Ph$_p$[O(CH$_2$)]$_{1-10}$PPh$_3$, -Ph$_p$[NH(CH$_2$)]$_{1-10}$PPh$_3$, -Ph$_p$Cl, -Ph$_p$NO$_2$, -Ph$_p$CF$_3$, or -Ph$_p$C(CF$_3$)$_3$, -PhF$_5$, and -Ph$_p$NMe$_2$ wherein p indicates that the OMe, Cl, NO$_2$, CF$_3$, and/or C(CF$_3$)$_3$ groups are in the para position of the phenyl ring relative to the position at which the phenyl ring is attached to the remainder of the compound.

In some embodiments, $R^2$ can be selected from alkyl or phenyl. In particular disclosed embodiments, $R^2$ is methyl, ethyl, propyl, butyl, or phenyl. In some embodiments, the phenyl ring can comprise one or more $R^5$ groups as discussed above for $R^1$. In yet additional embodiments, $R^2$ can be a linker-X group as described above.

In some embodiments, each of $R^3$ and $R^4$ independently is selected from —NH$_2$, —N(H)(CH$_2$)$_n$CH$_3$, —N(H)(CH$_2$)$_n$CF$_3$, —N[(CH$_2$)$_n$CH$_3$]$_2$, or —N[(CH$_2$)$_n$CF$_3$]$_2$, wherein each n independently is an integer selected from 0 to 10 (e.g., 1, 2, 3, 4, 5, 6, 7, 8, 9, or 10). In yet additional embodiments, each of $R^3$ and $R^4$ independently can be selected from —N(H)linker-X, —N[(CH$_2$)$_n$CH$_3$]linker-X, or —N[(CH$_2$)$_n$CF$_3$]linker-X, wherein the linker-X group is as described above for $R^5$ and $R^2$.

In some embodiments, disclosed representative compounds can have structures satisfying any one or more of the following formulas. In some embodiments, the representative compounds can be the free ligand component of the complexes illustrated below.

TABLE 1

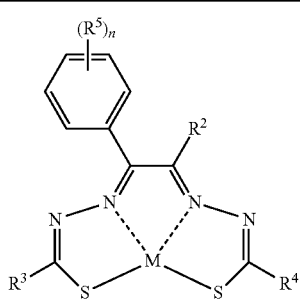

TABLE 1-continued

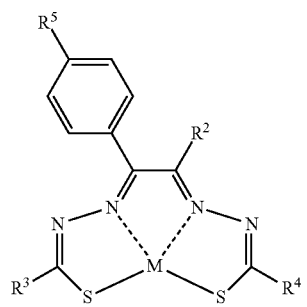

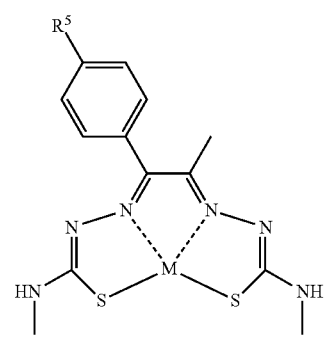

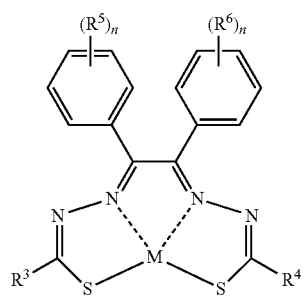

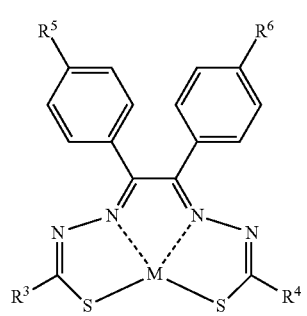

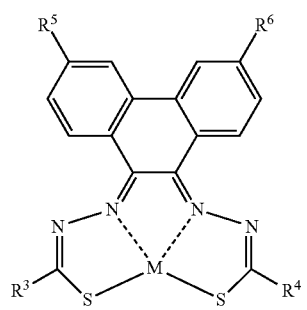

TABLE 1-continued
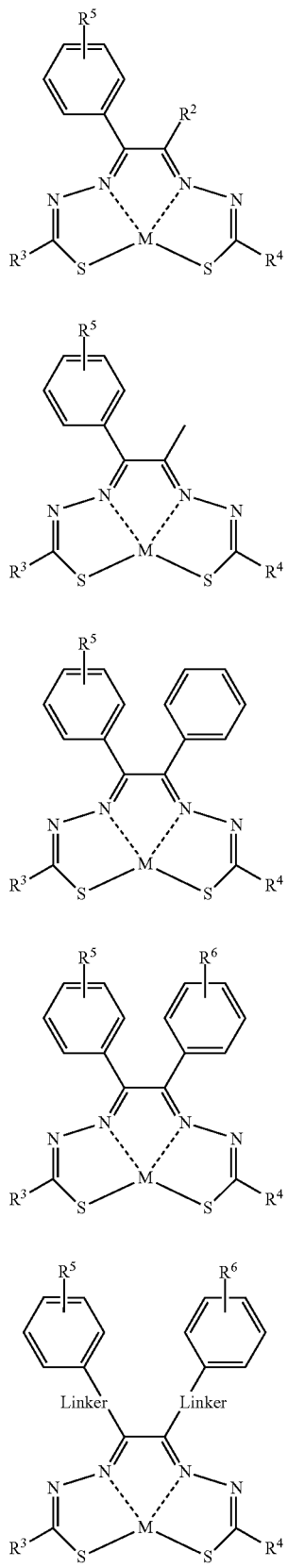
TABLE 1-continued
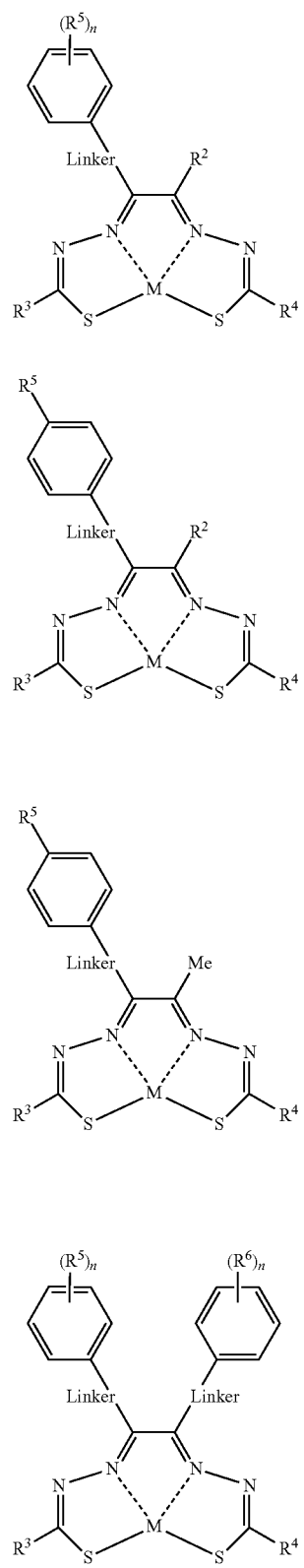

TABLE 1-continued

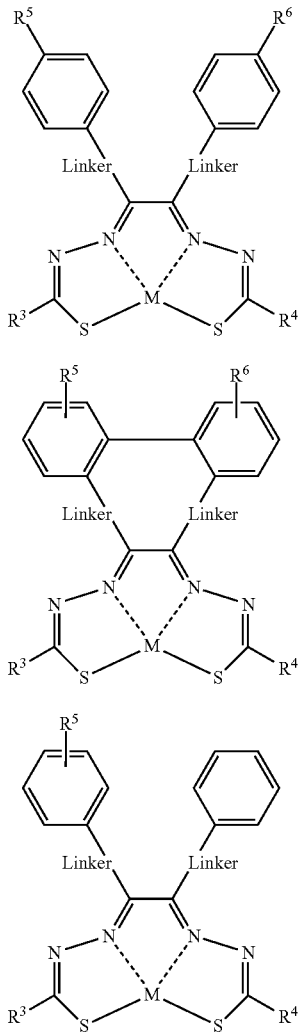

With reference to the above formulas, each of M, $R^3$, $R^4$, each $R^5$, and n independently can be selected from groups recited above for Formulas I, IA, and IB; each $R^6$ independently can be selected from any of the groups recited above for $R^5$. In some embodiments, each $R^5$ can be the same or different from each other $R^5$, each $R^6$ can be the same or different from each other $R^6$, and/or $R^5$ and $R^6$ can be the same or different from each other.

In yet additional embodiments, the compound embodiments described herein can have structures satisfying any one or more of the following formulas. In some embodiments, the representative compounds can be the free ligand component of the complexes illustrated below.

TABLE 2

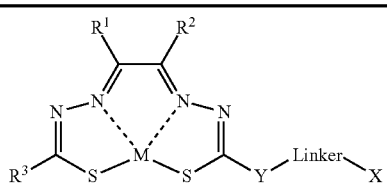

TABLE 2-continued

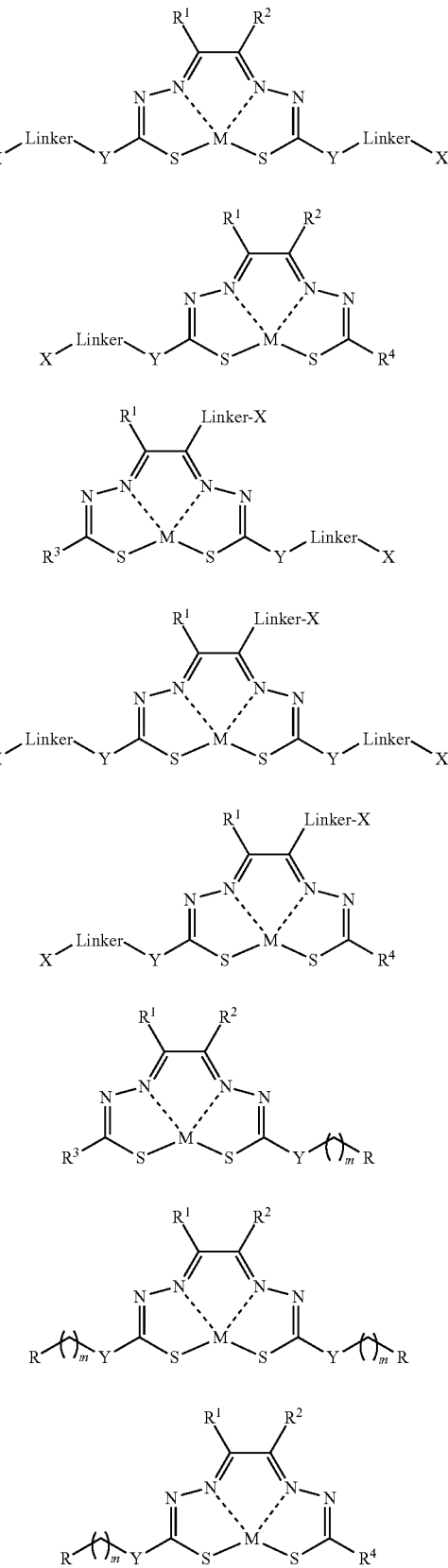

TABLE 2-continued
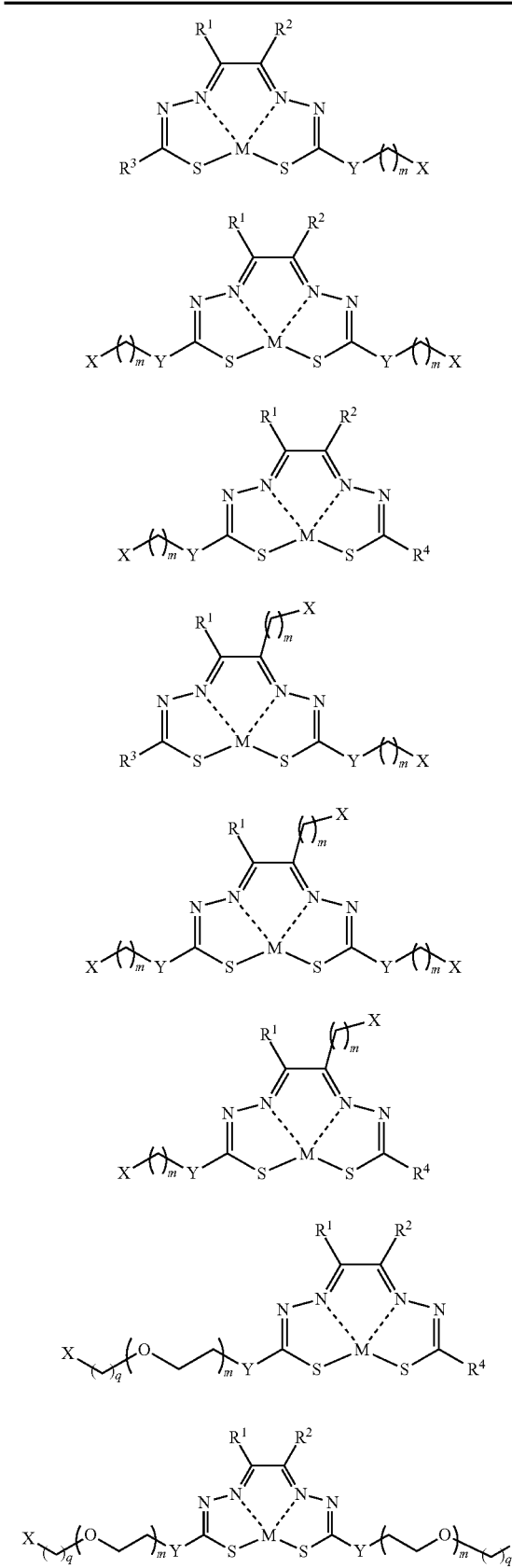
TABLE 2-continued
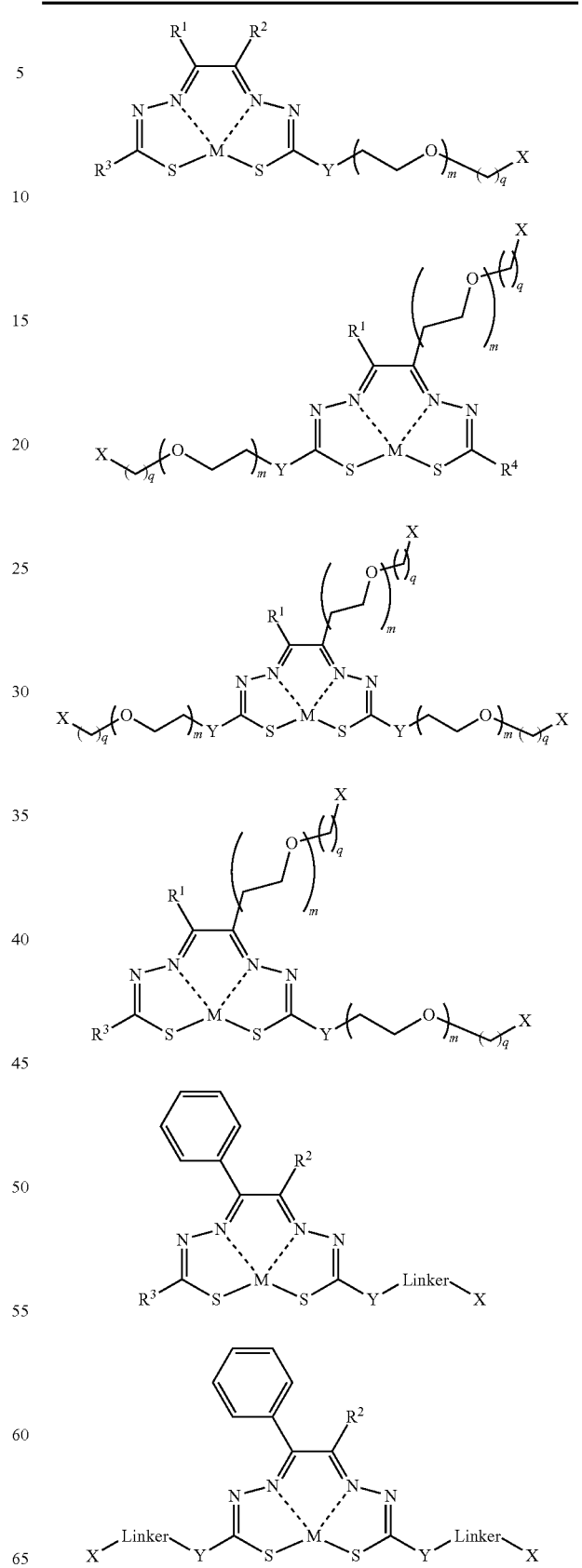

TABLE 2-continued
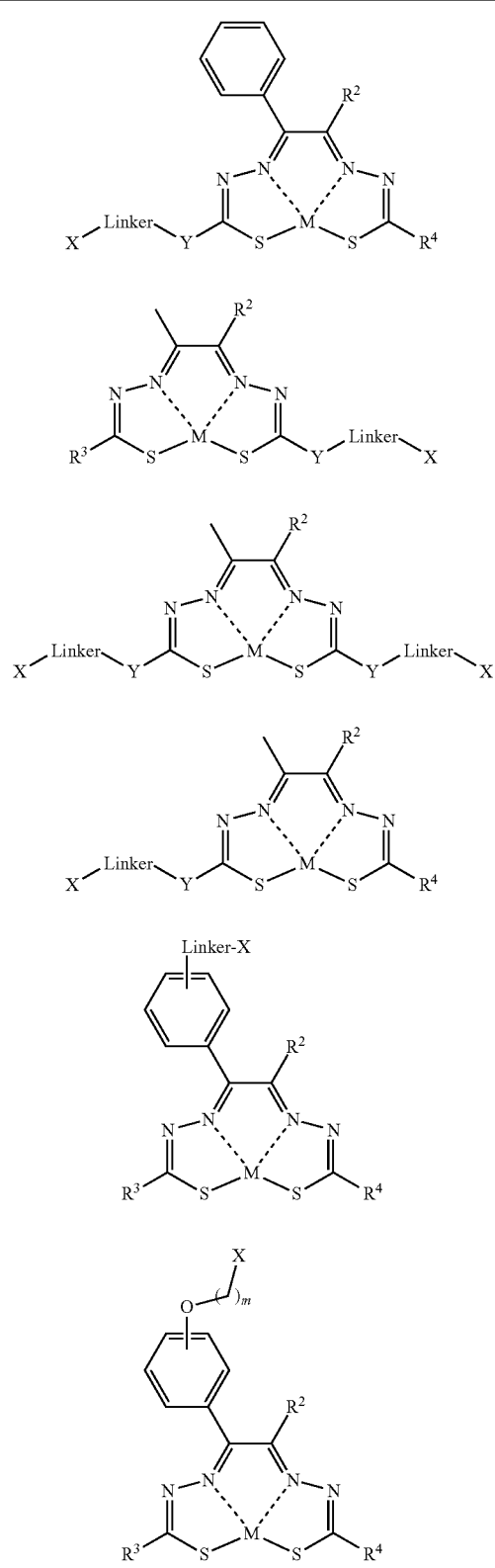
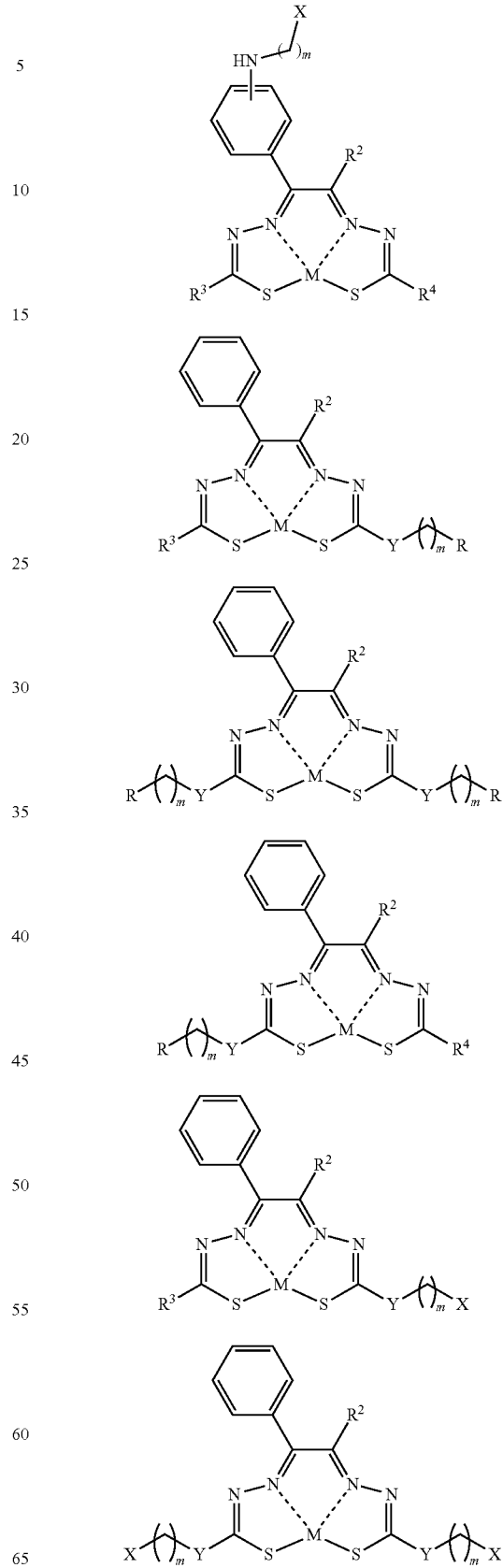

TABLE 2-continued
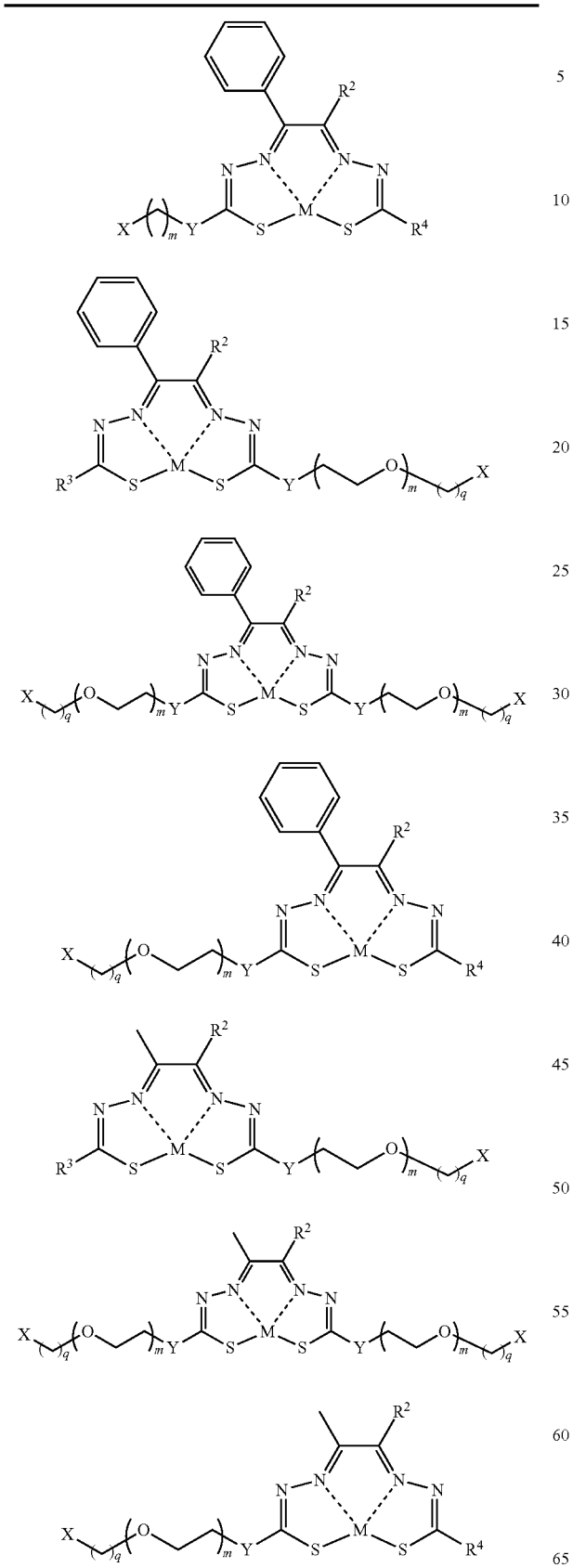
TABLE 2-continued
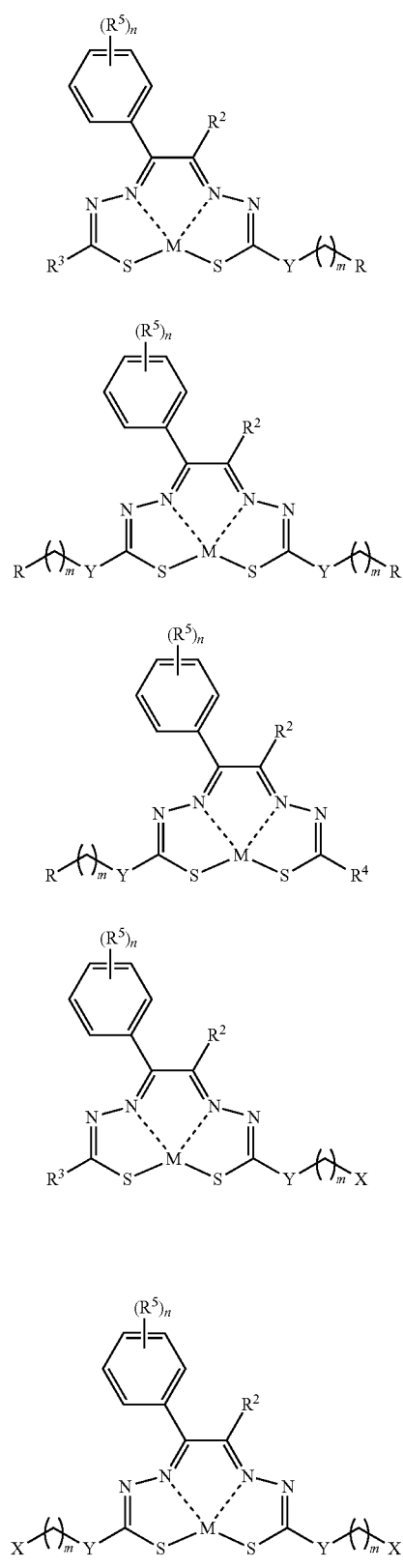

TABLE 2-continued

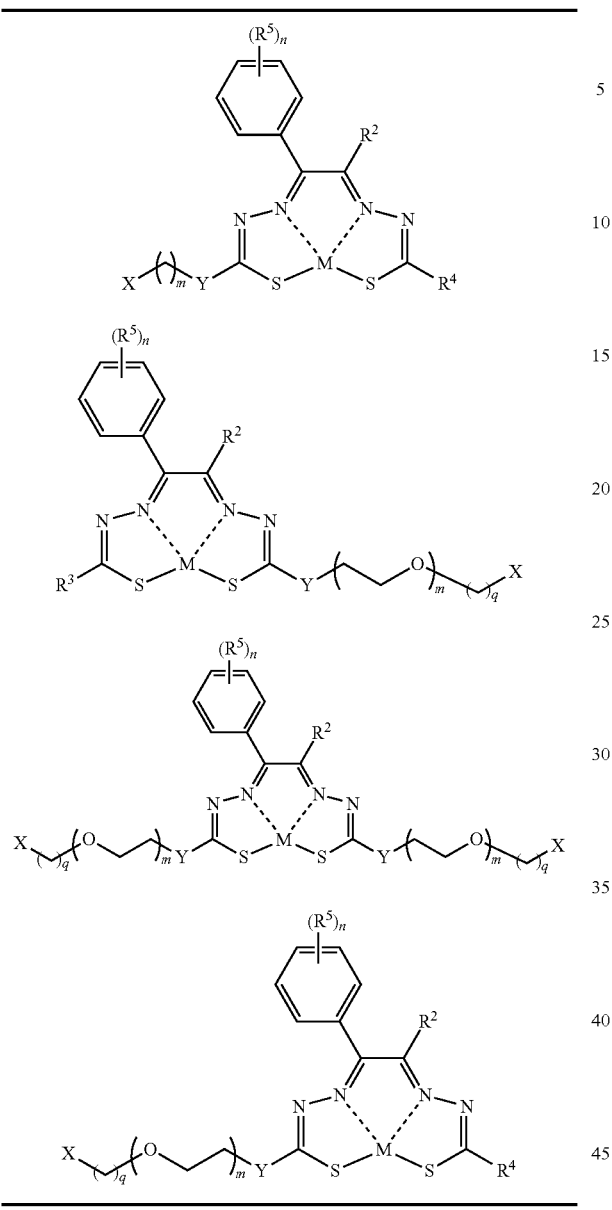

TABLE 3

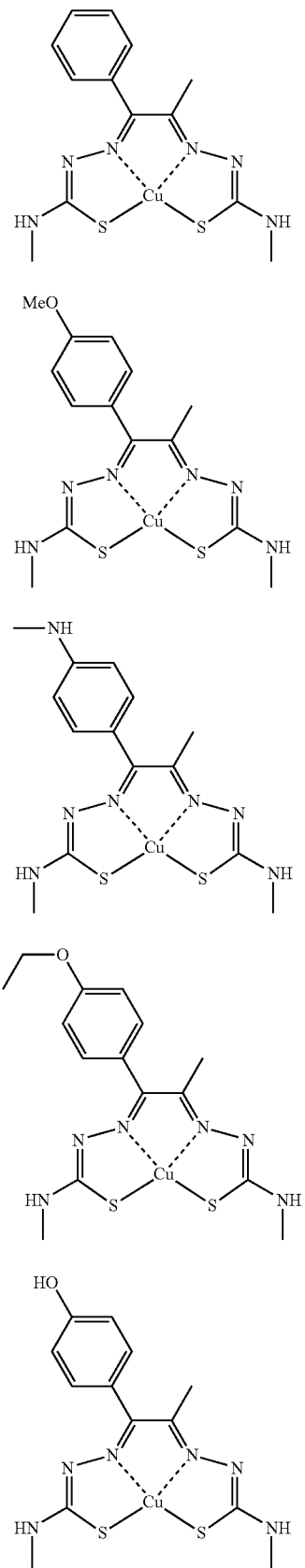

With reference to the formulas above, each of $R^1$, $R^2$, $R^3$, $R^4$ independently can be selected from groups recited above for Formulas I, IA, and IB; each linker and X group can be as recited above for the "linker-X" moieties described above; each Y independently can be selected from O, S, or NR (wherein R is selected from hydrogen, aliphatic, aryl, heteroaliphatic, aliphatic-aryl, heteroaryl, aliphatic-heteroaryl, heteroaliphatic-aryl, heteroaliphatic-heteroaryl, or any combination thereof); each R independently can be methyl, trifluoromethyl, $C(CF_3)_3$; each m is an integer selected from 1 to 30, such as 1 to 20, or 1 to 10, or 1 to 5; each q is an integer selected from 0 to 30, such as 1 to 20, or 1 to 10, or 1 to 5; and each n is an integer selected from 1 to 5.

Representative compounds having structures satisfying any one or more of the formulas above are provided. In some embodiments, the representative compounds can be the free ligand component of the complexes illustrated below.

TABLE 3-continued
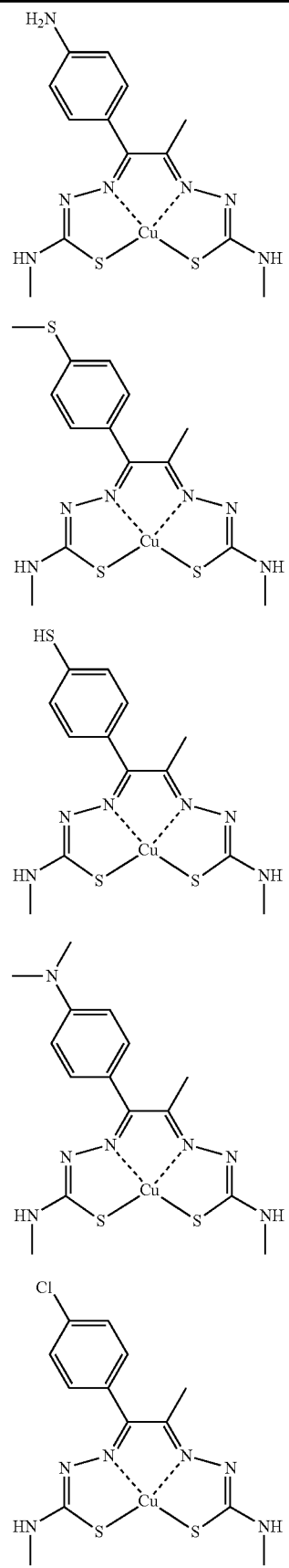
TABLE 3-continued
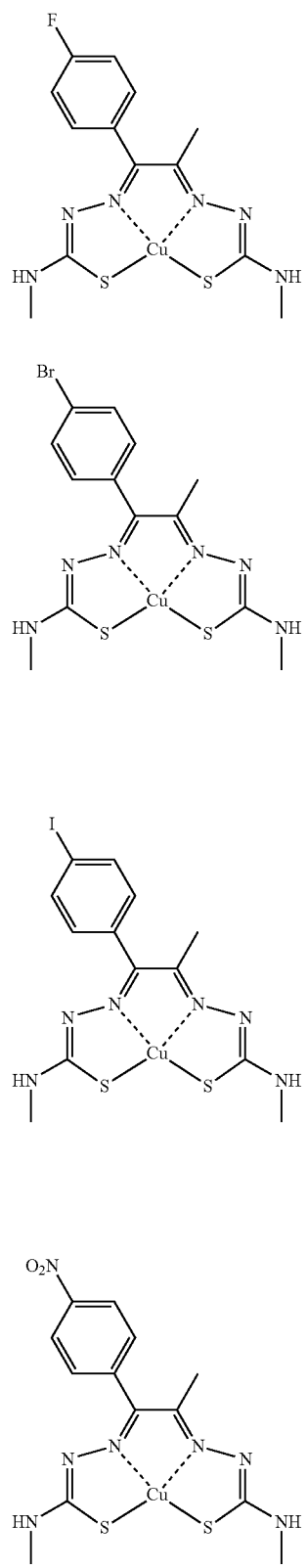

TABLE 3-continued
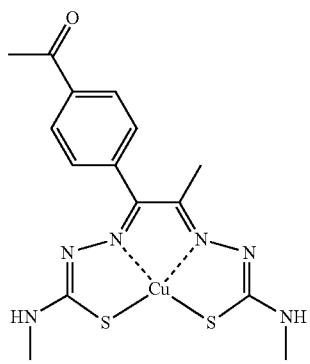
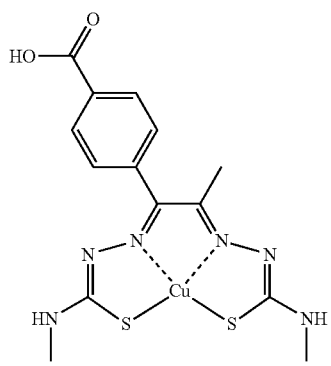
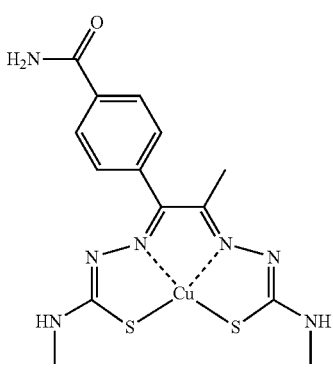
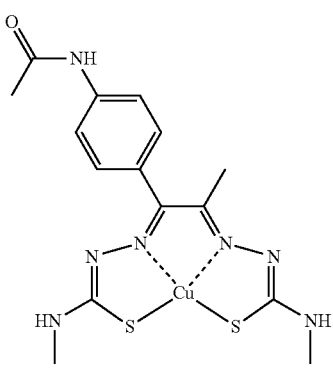
TABLE 3-continued
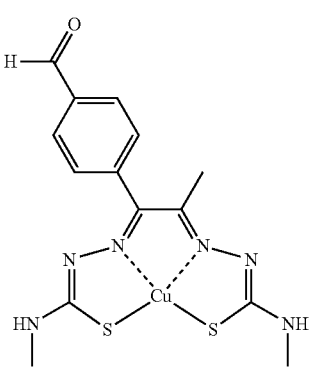
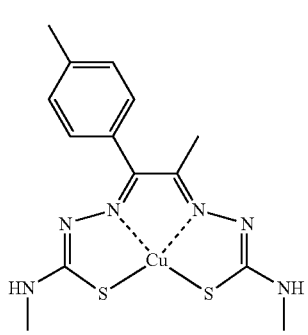
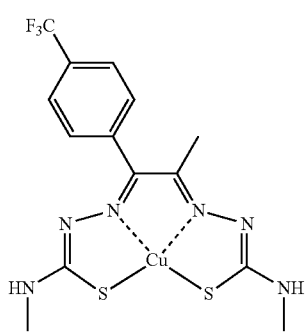
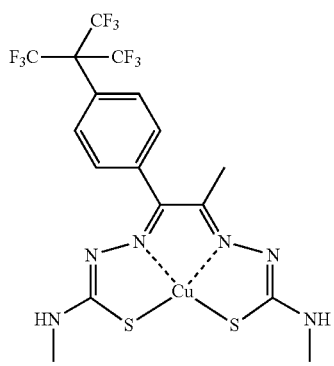

TABLE 3-continued
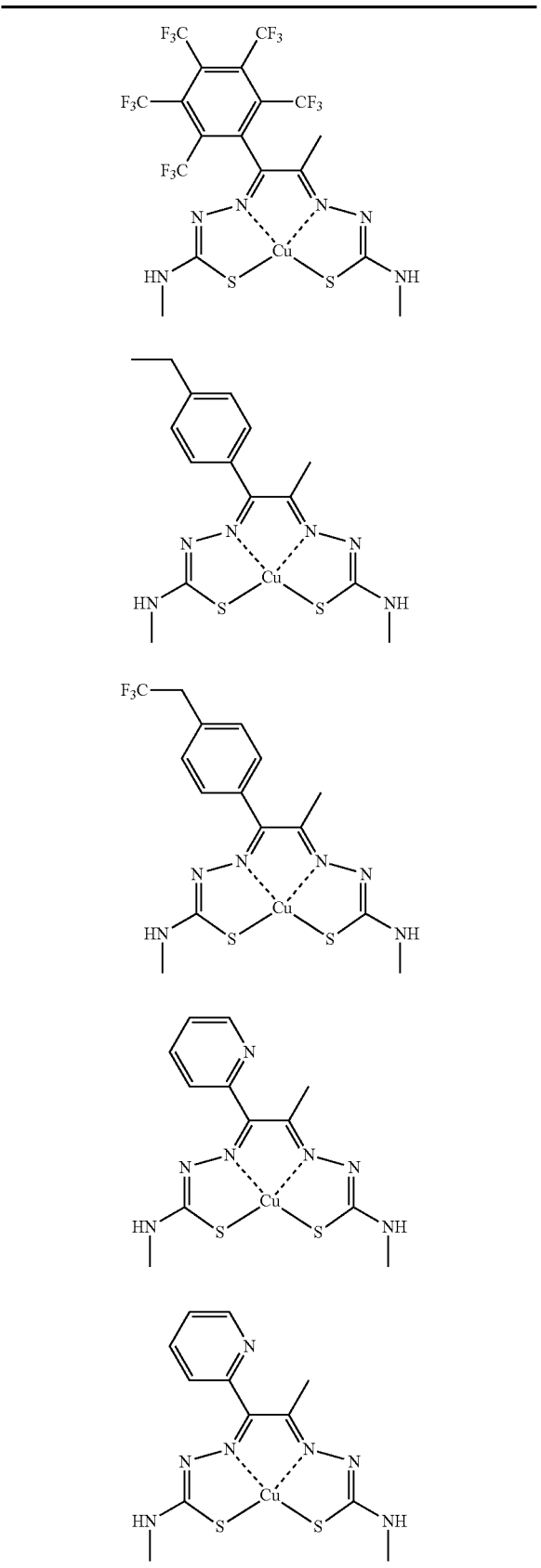
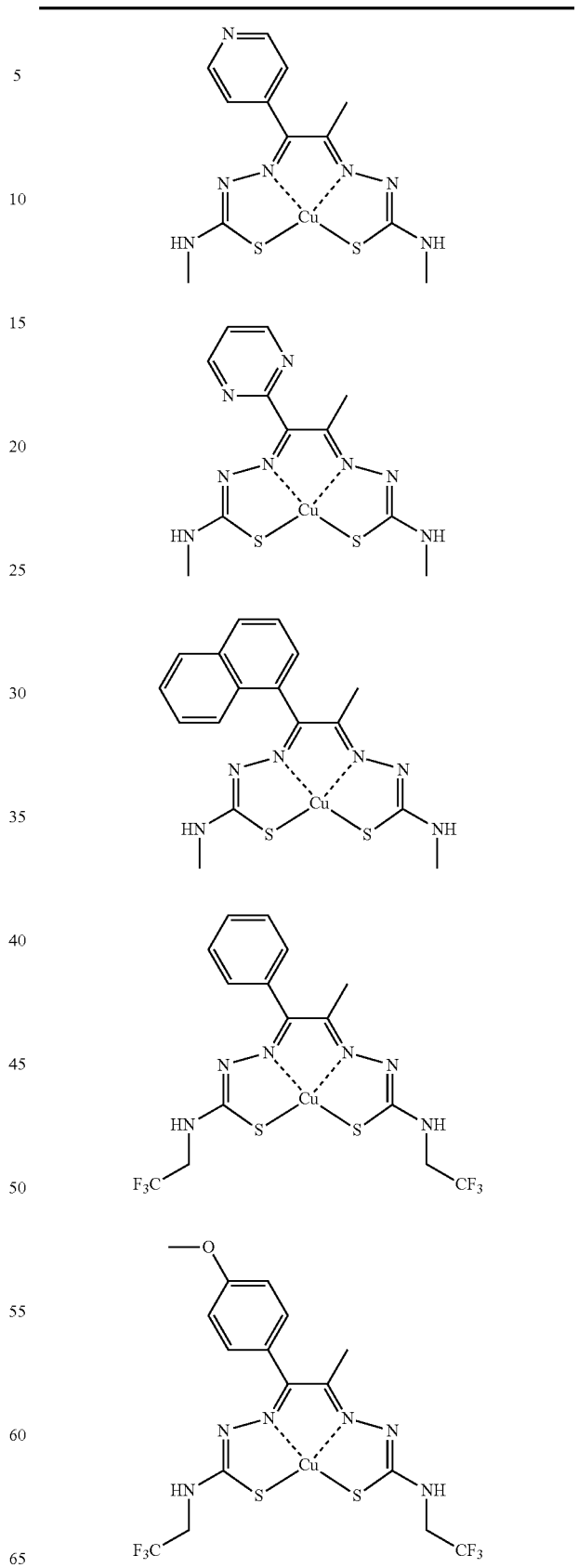

TABLE 3-continued
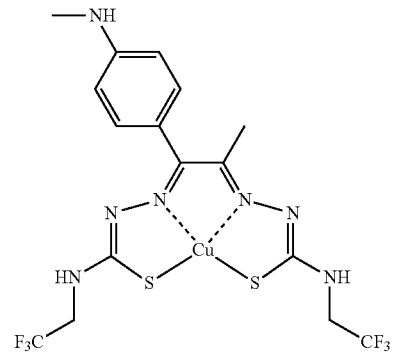
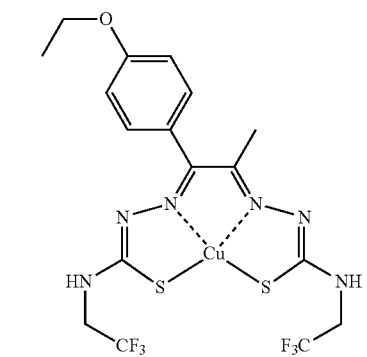
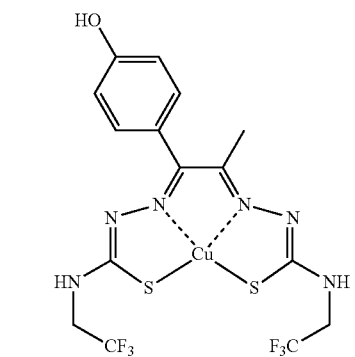
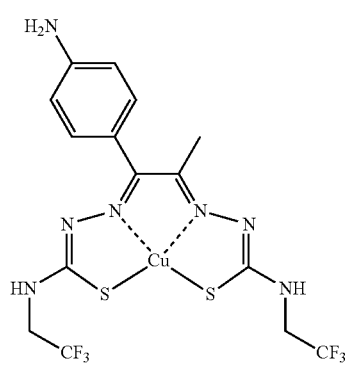
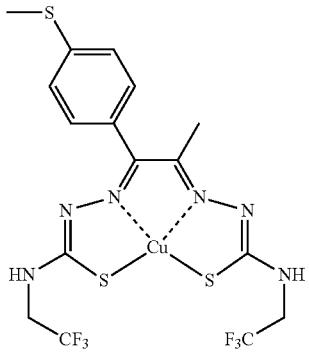
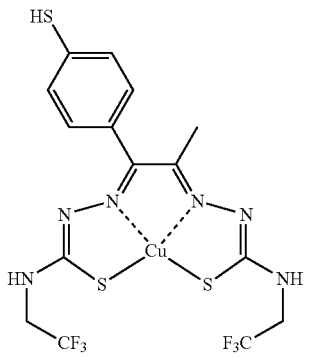
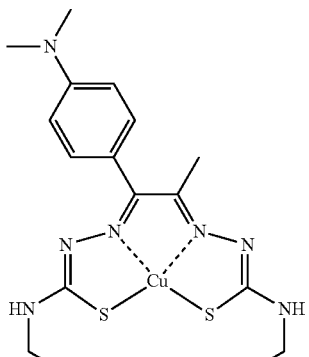
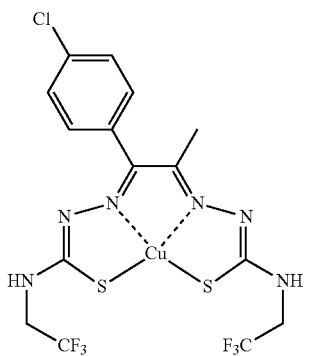

TABLE 3-continued
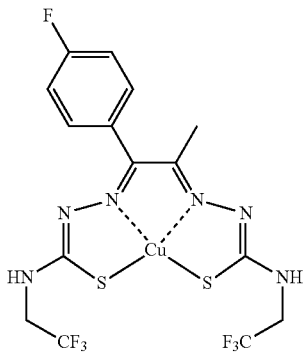
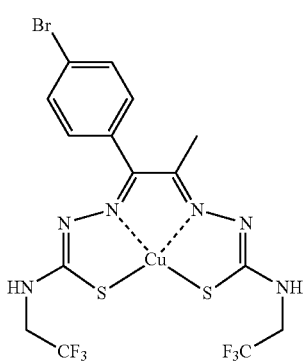
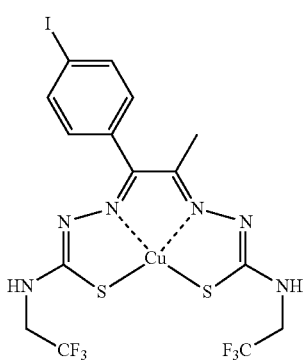
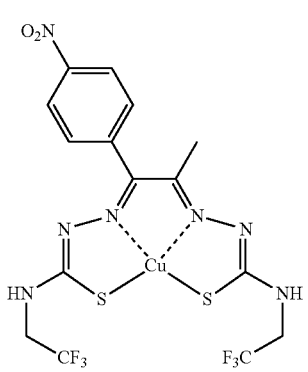
TABLE 3-continued
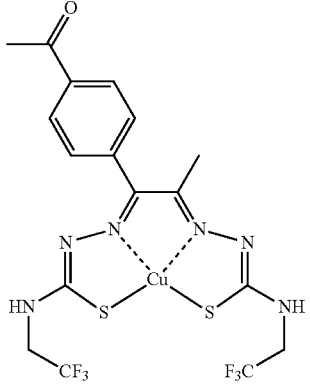
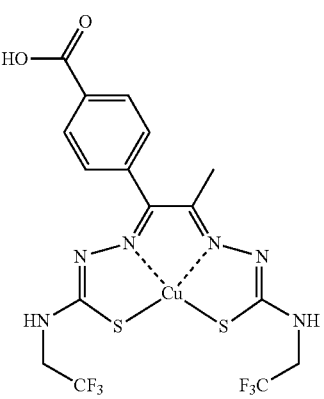
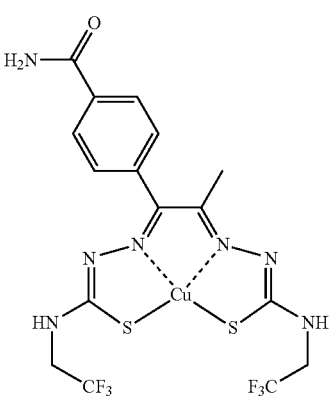
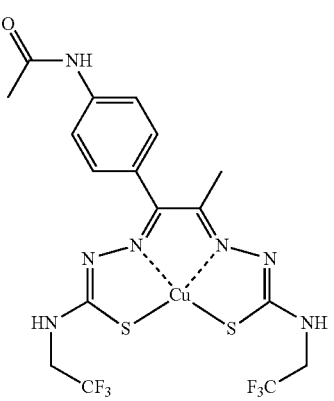

TABLE 3-continued
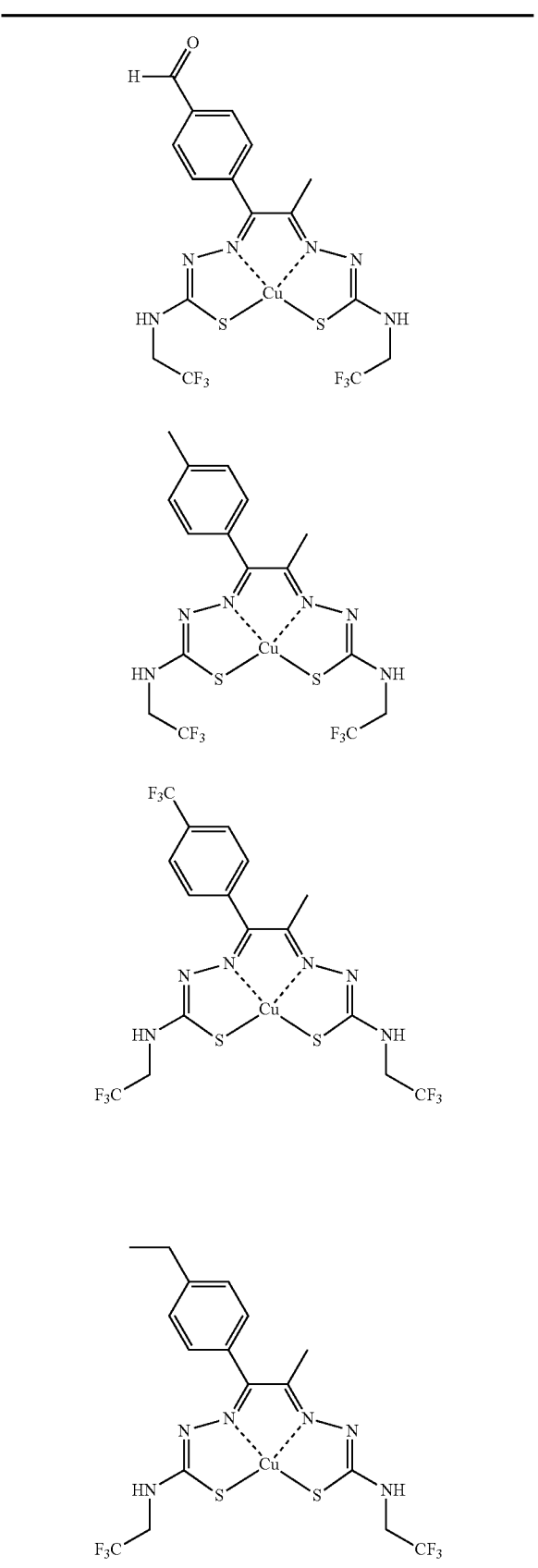
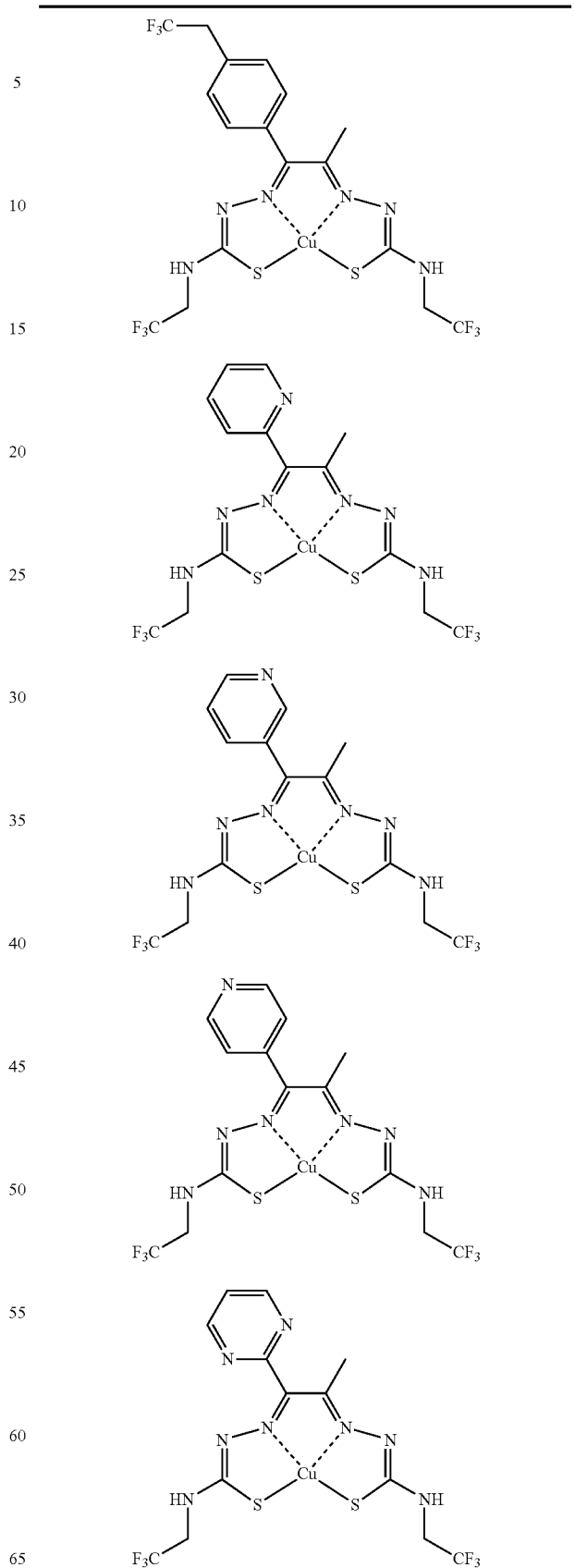

TABLE 3-continued
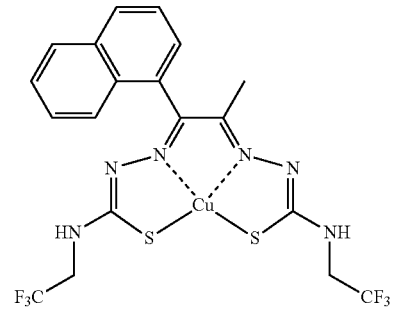
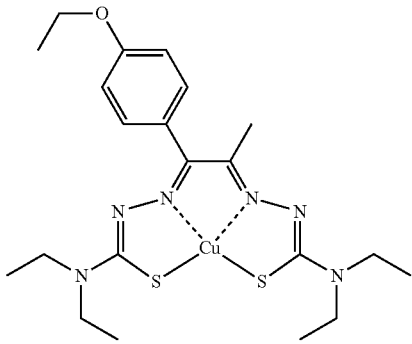
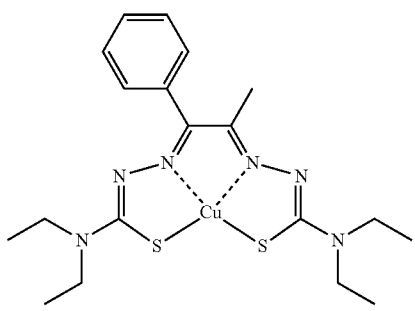
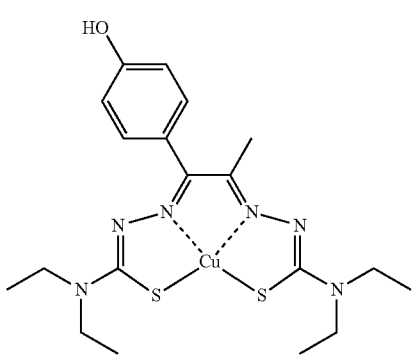
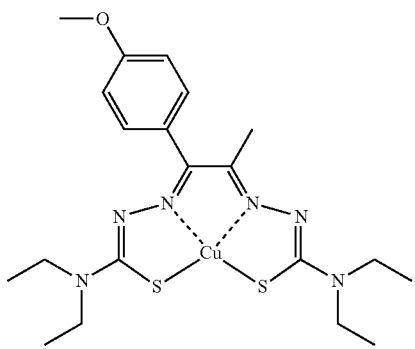
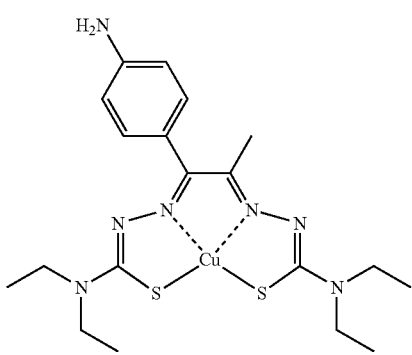
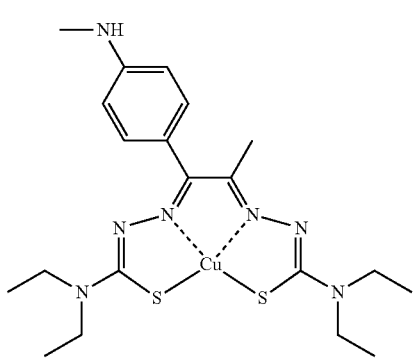
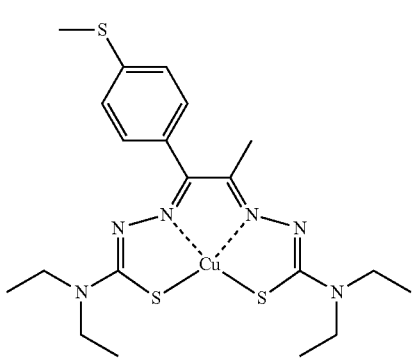

TABLE 3-continued
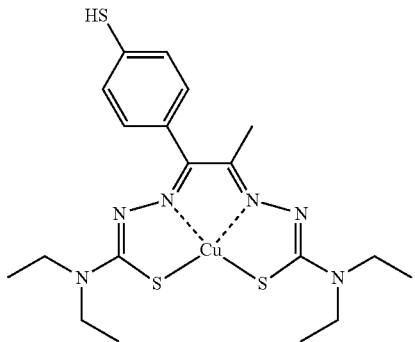
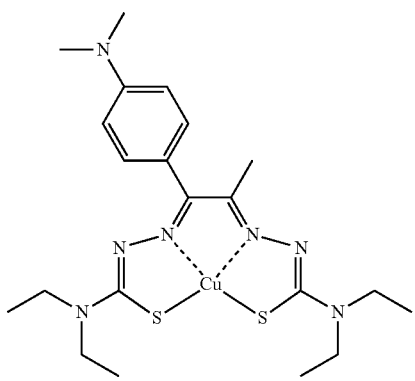
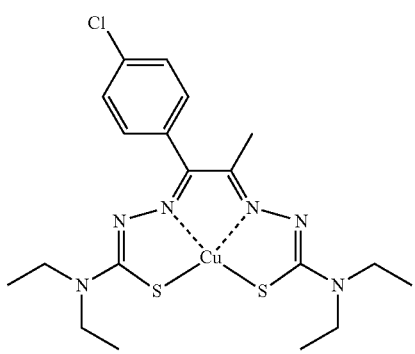
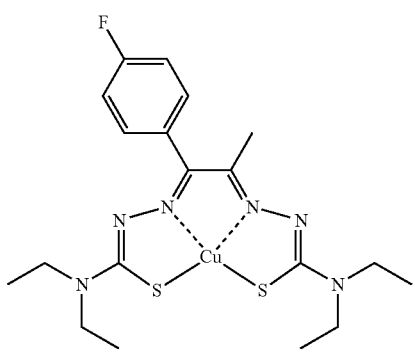
TABLE 3-continued
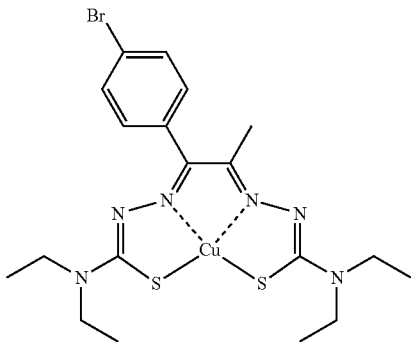
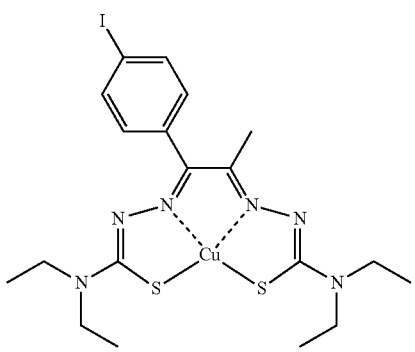
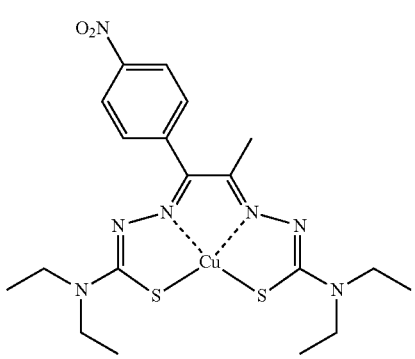
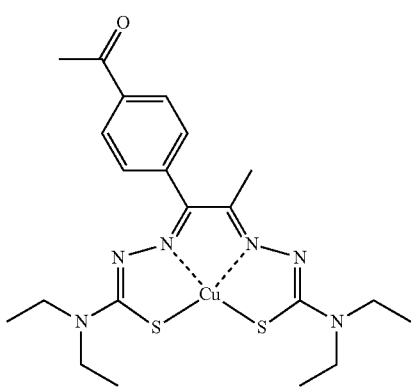

TABLE 3-continued
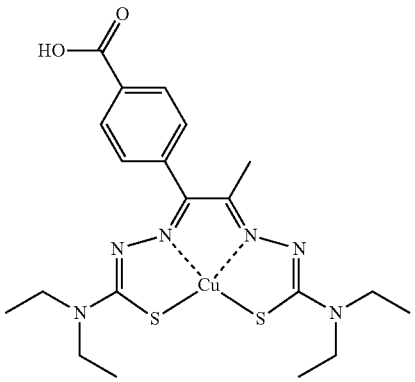
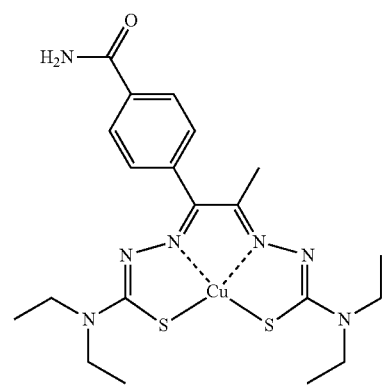
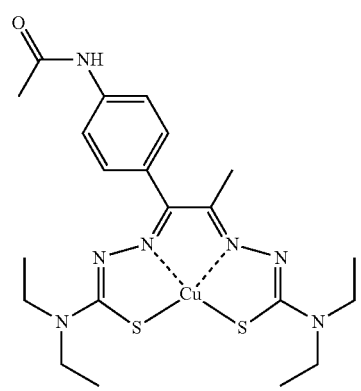
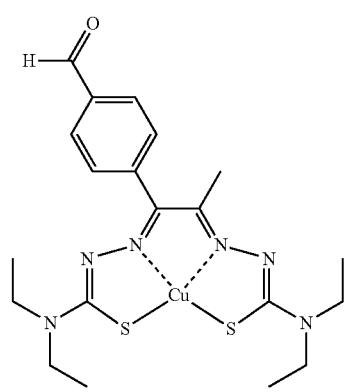
TABLE 3-continued
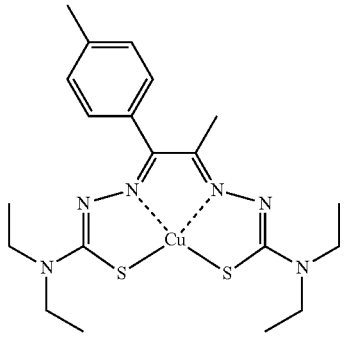
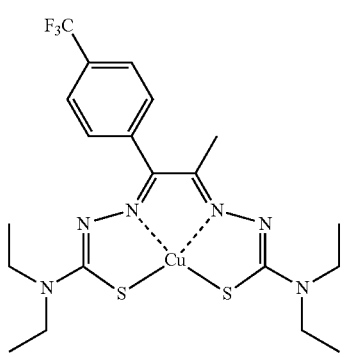
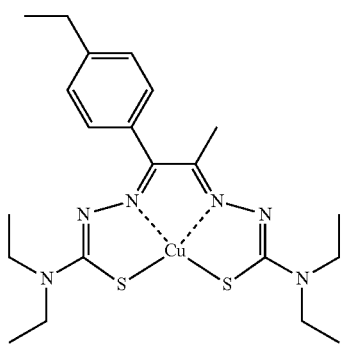
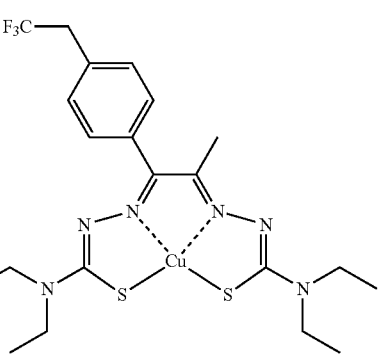

TABLE 3-continued
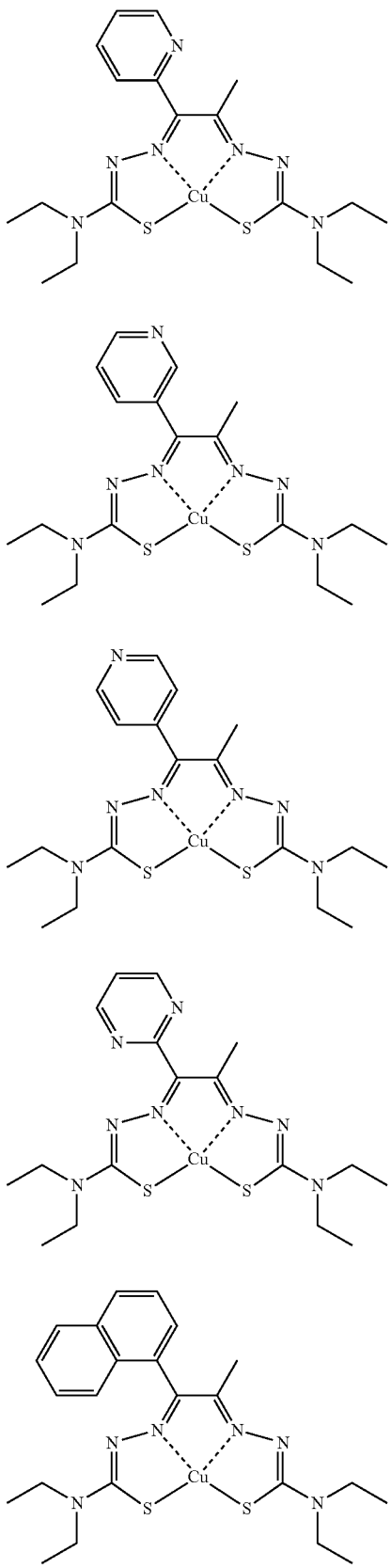
TABLE 3-continued
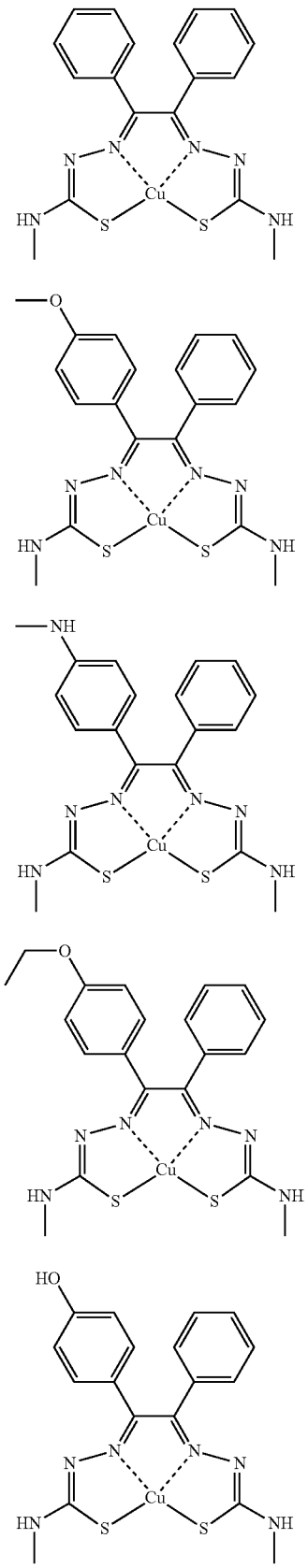

TABLE 3-continued
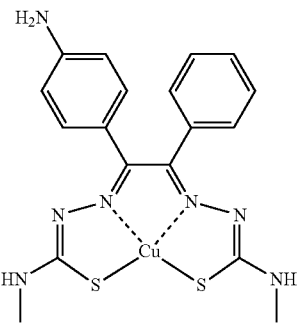
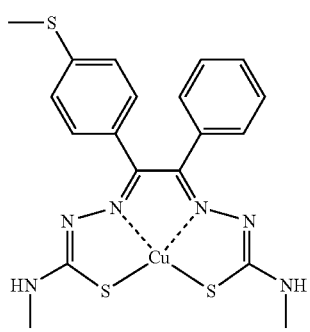
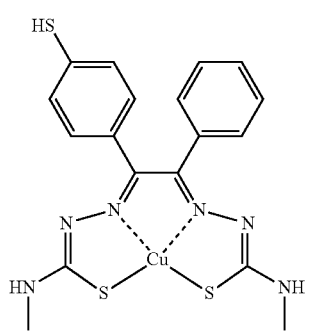
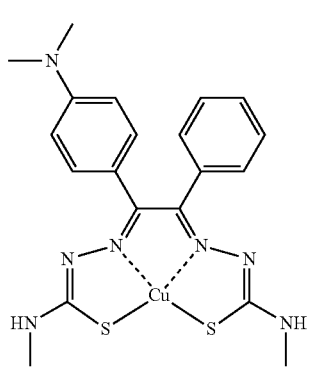
TABLE 3-continued
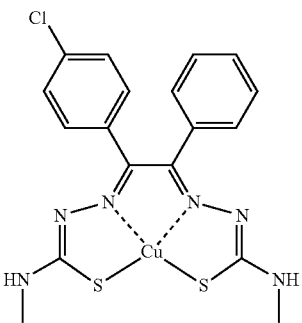
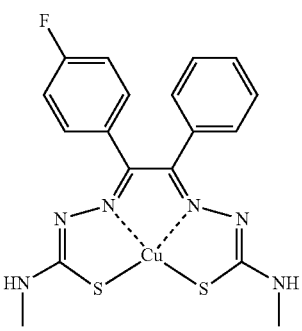
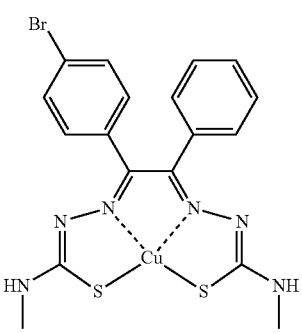
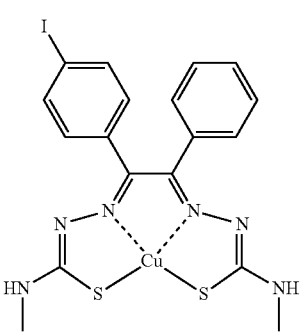
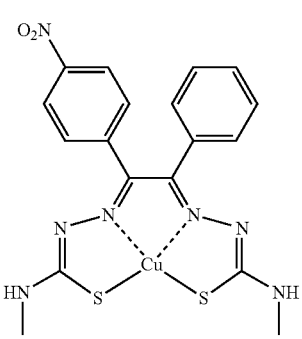

TABLE 3-continued
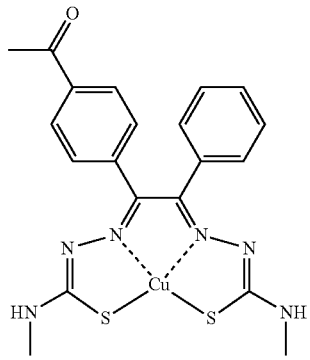
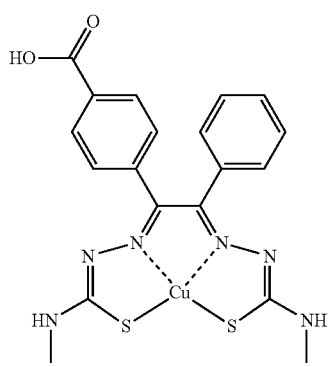
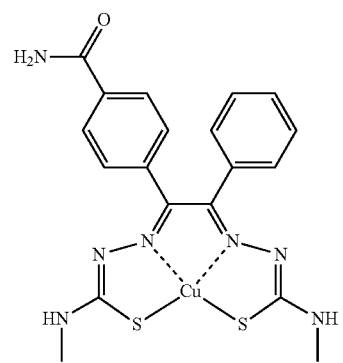
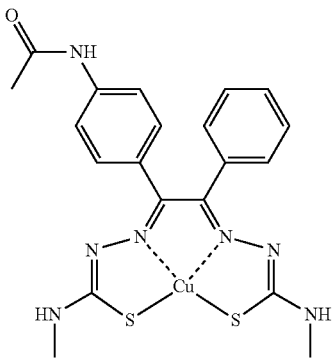
TABLE 3-continued
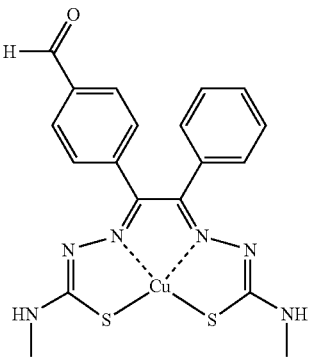
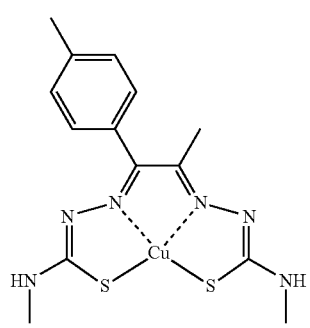
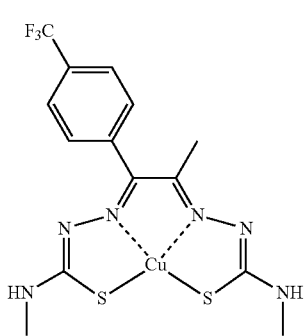
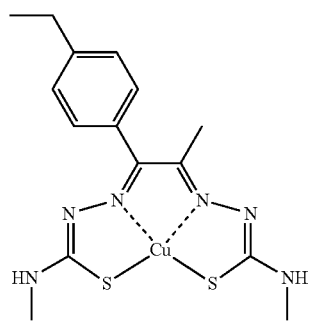

TABLE 3-continued
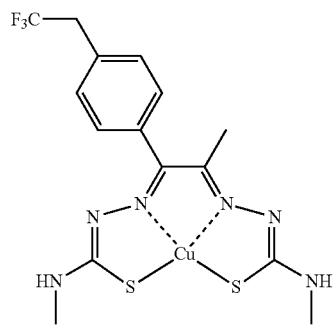
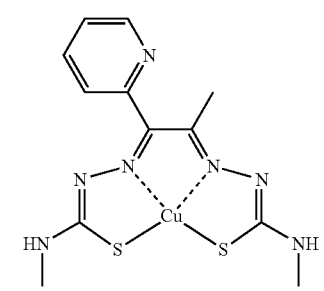
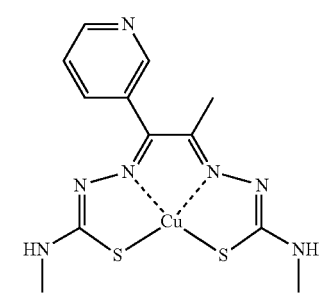
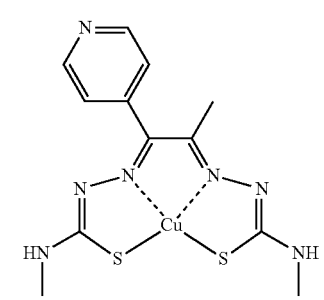
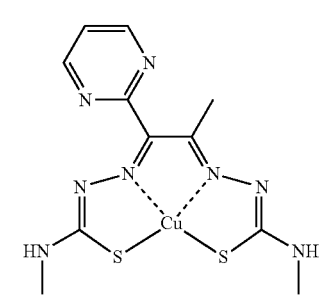
TABLE 3-continued
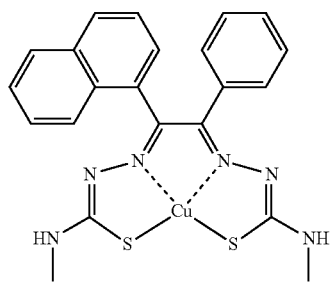
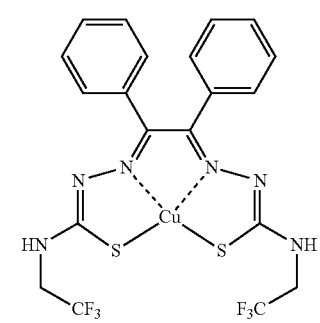
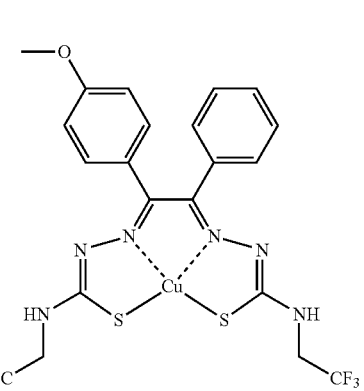
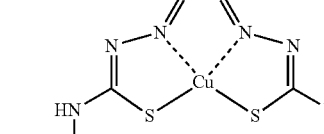

TABLE 3-continued
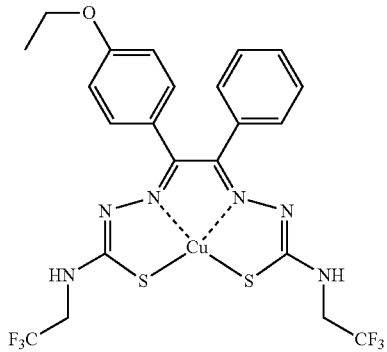
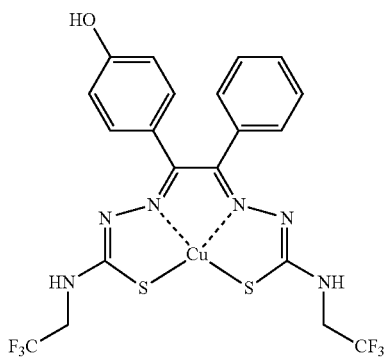
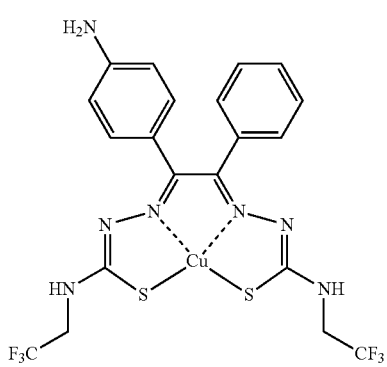
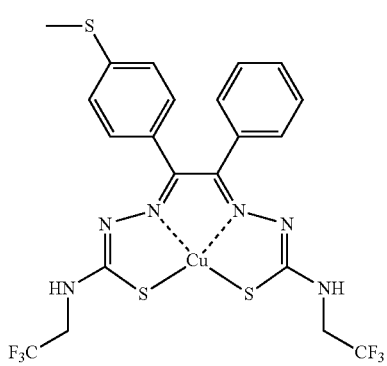
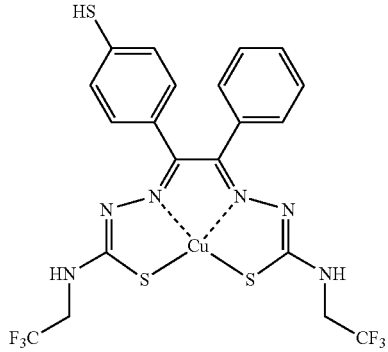
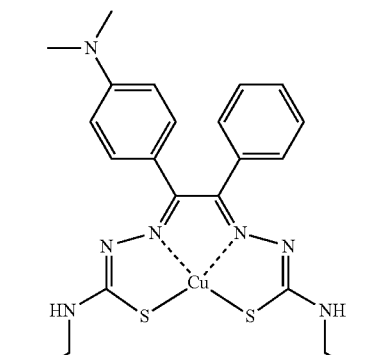
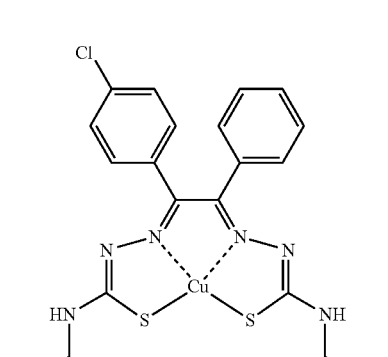
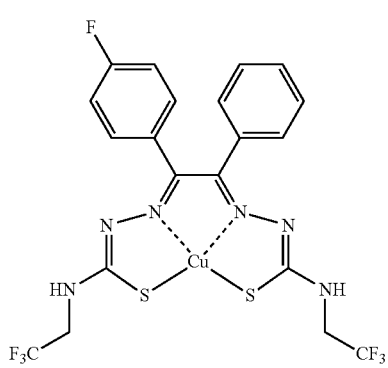

TABLE 3-continued
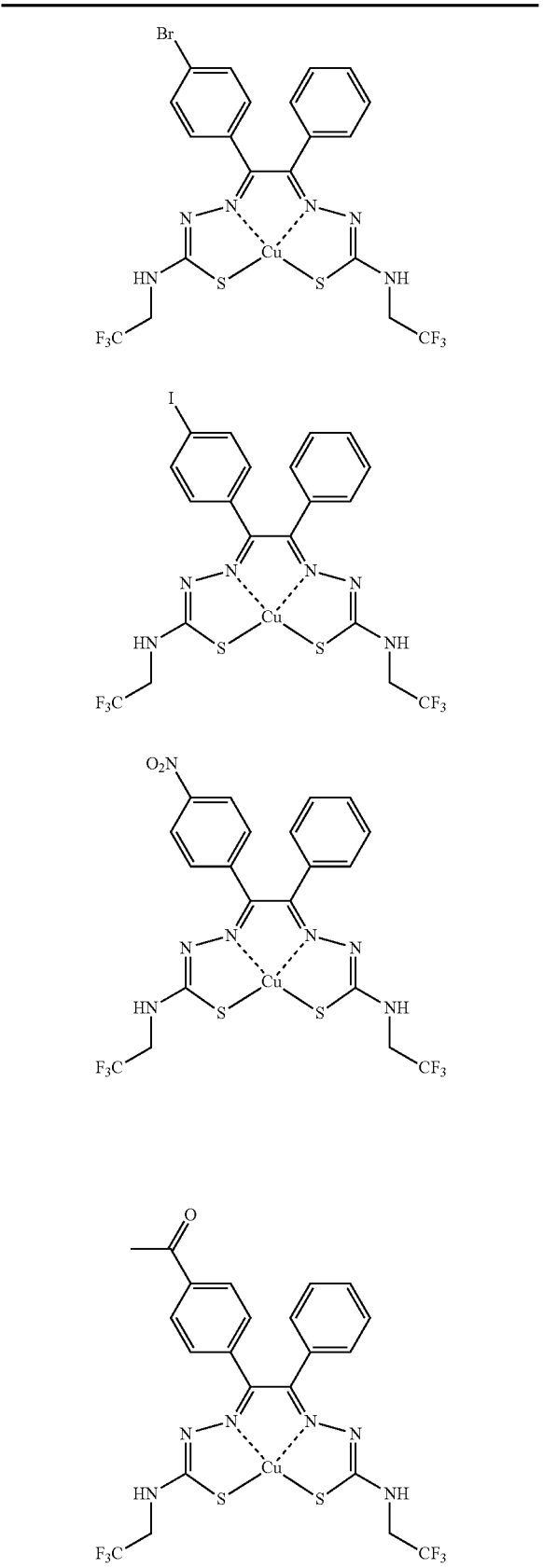
TABLE 3-continued
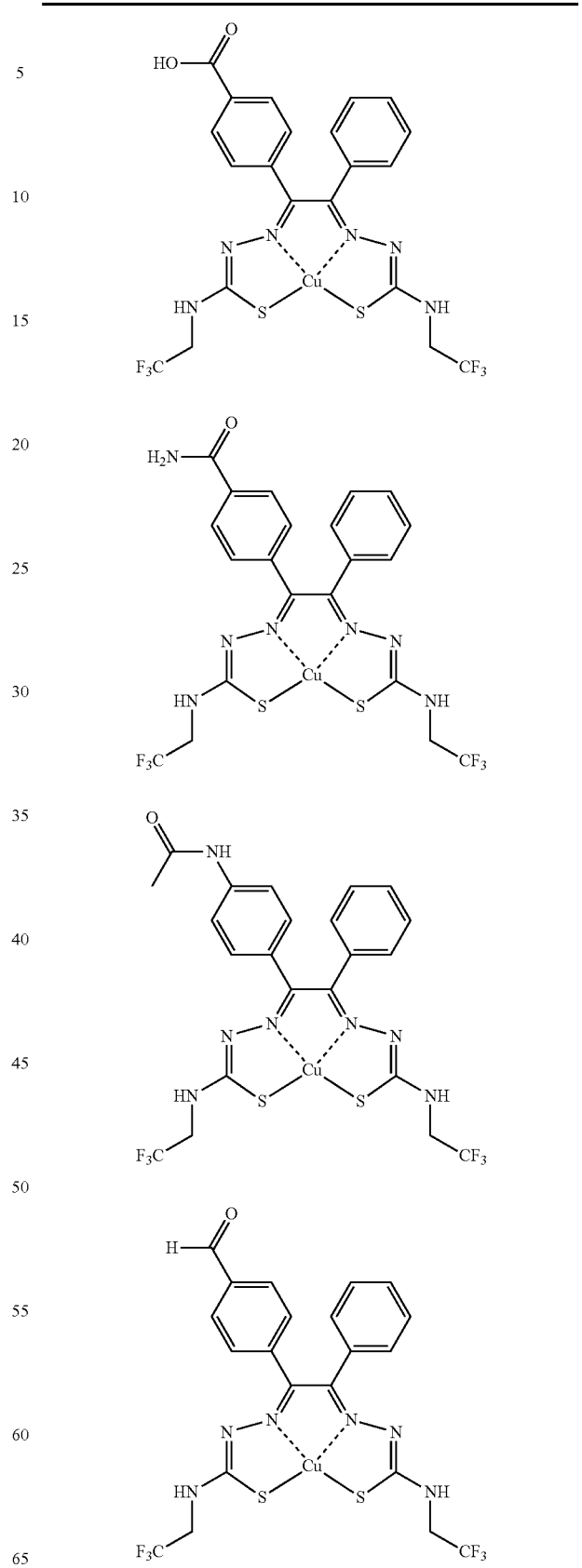

TABLE 3-continued
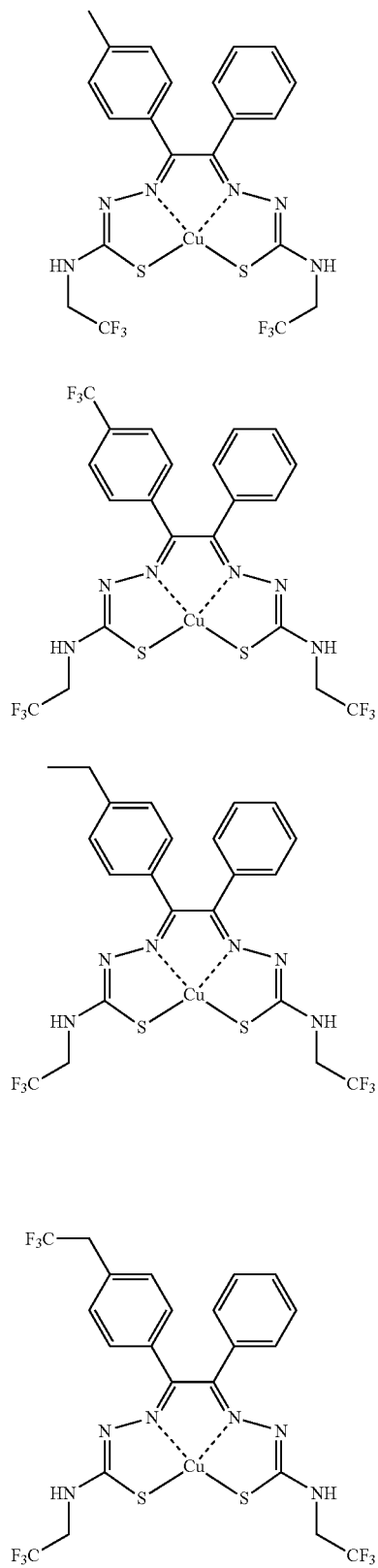
TABLE 3-continued
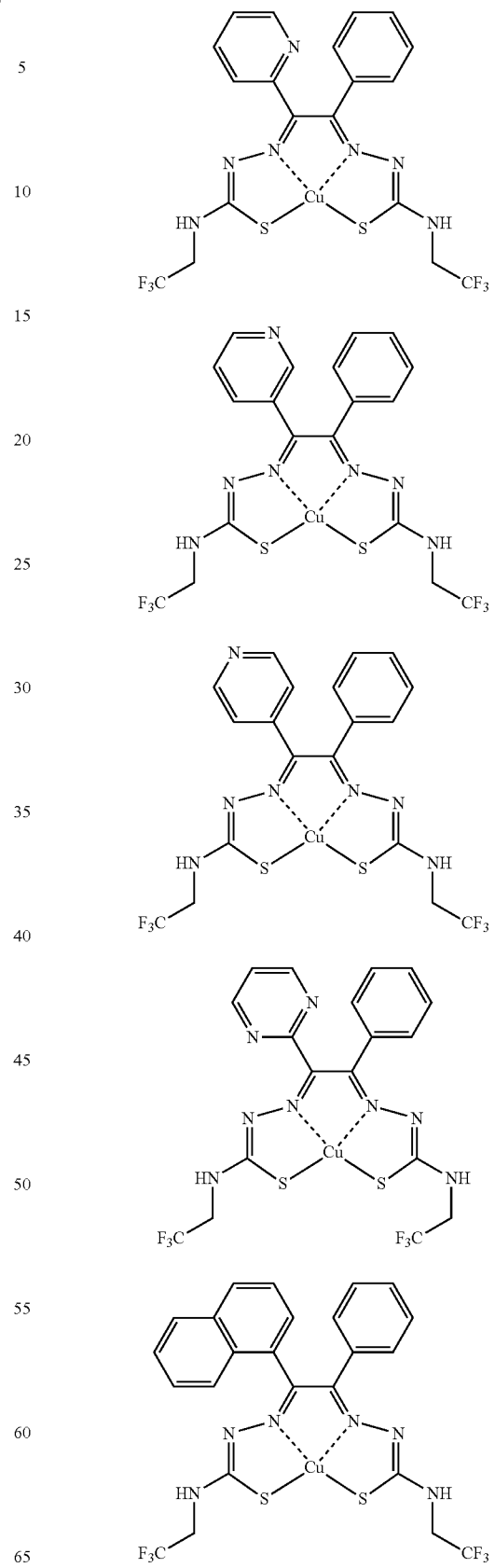

TABLE 3-continued
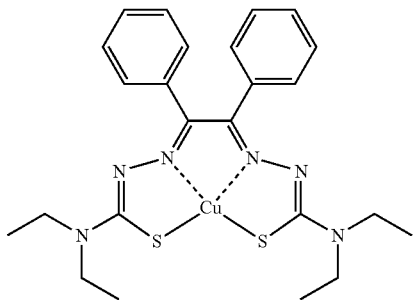
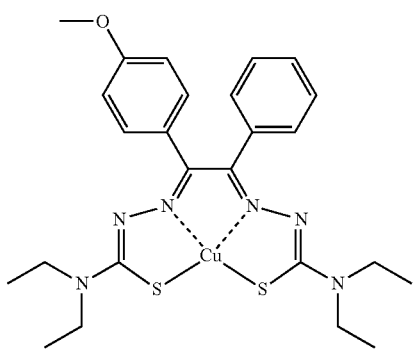
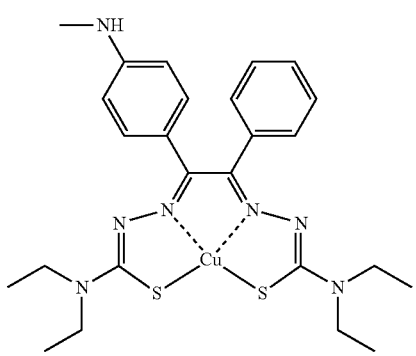
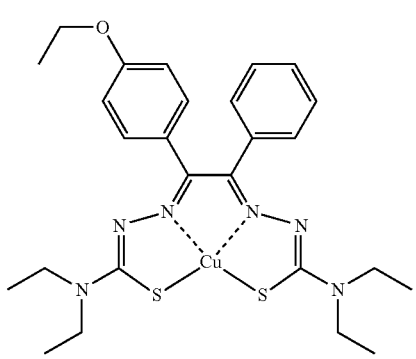
TABLE 3-continued
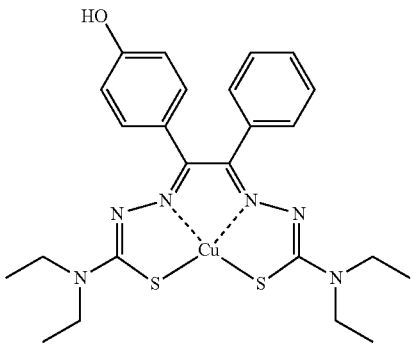
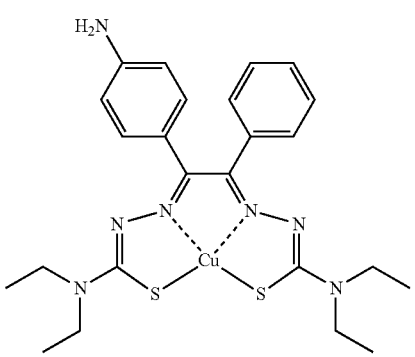
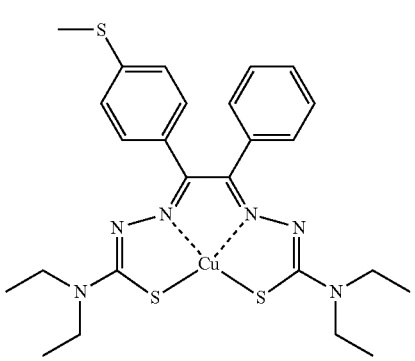
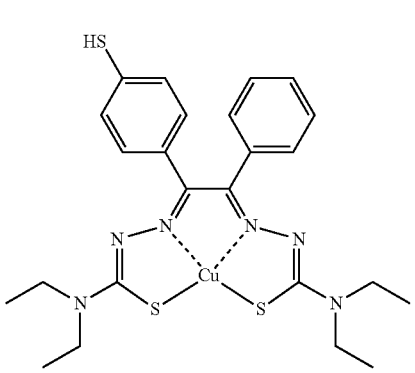

TABLE 3-continued
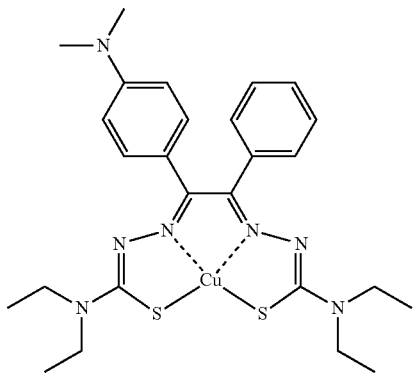
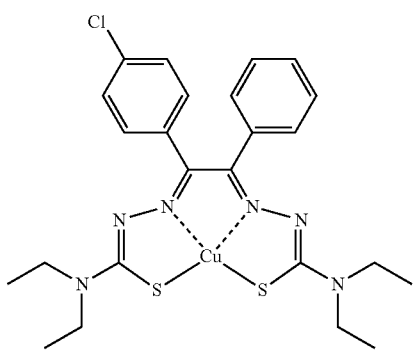
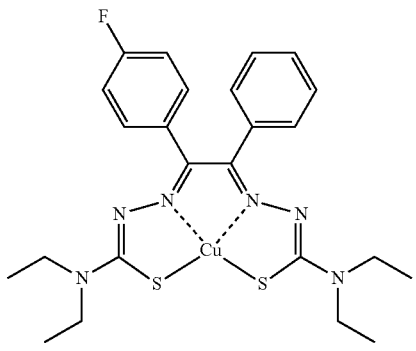
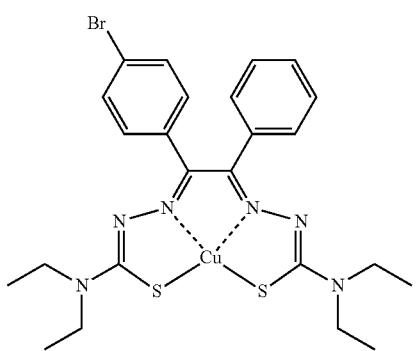
TABLE 3-continued
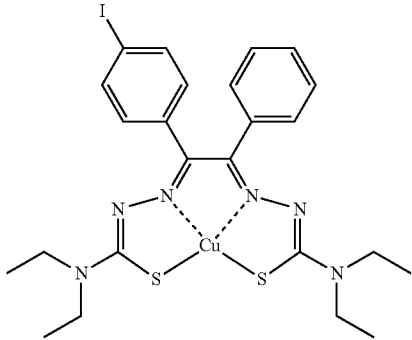
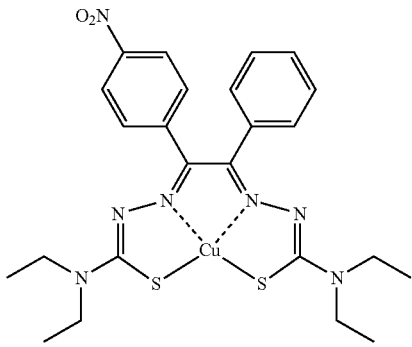
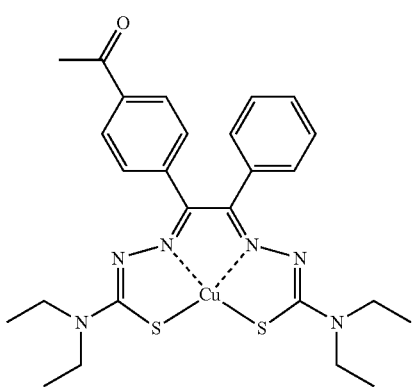
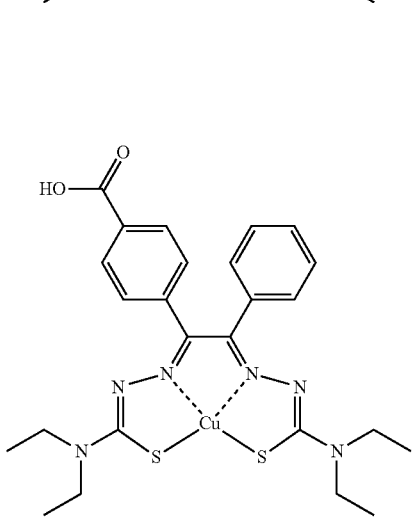

TABLE 3-continued
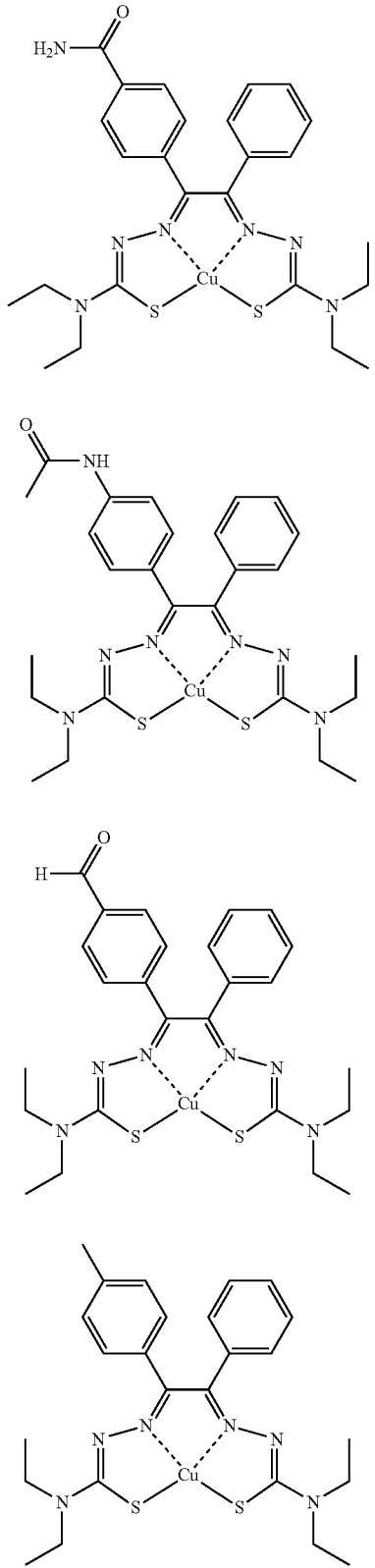
TABLE 3-continued
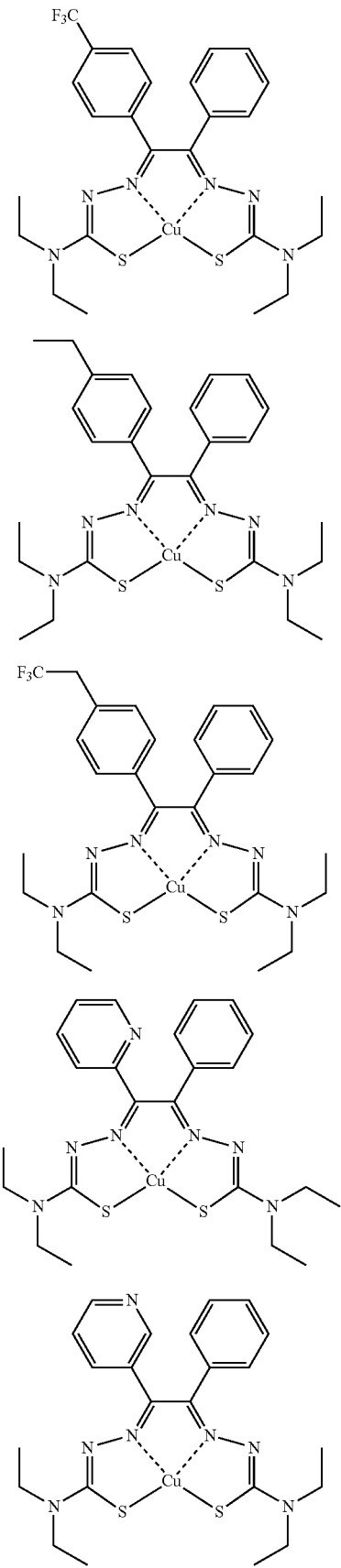

TABLE 3-continued
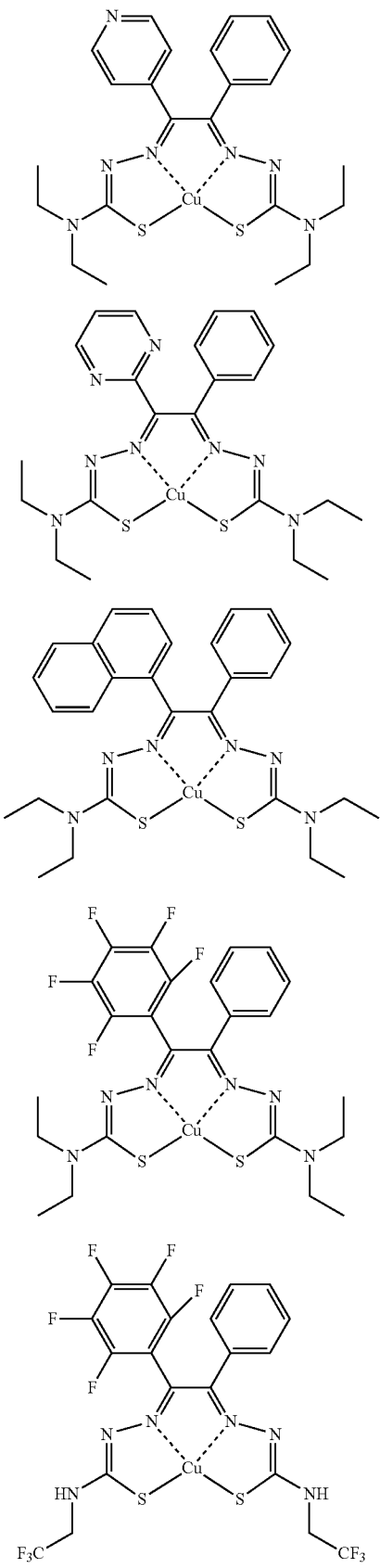
TABLE 3-continued
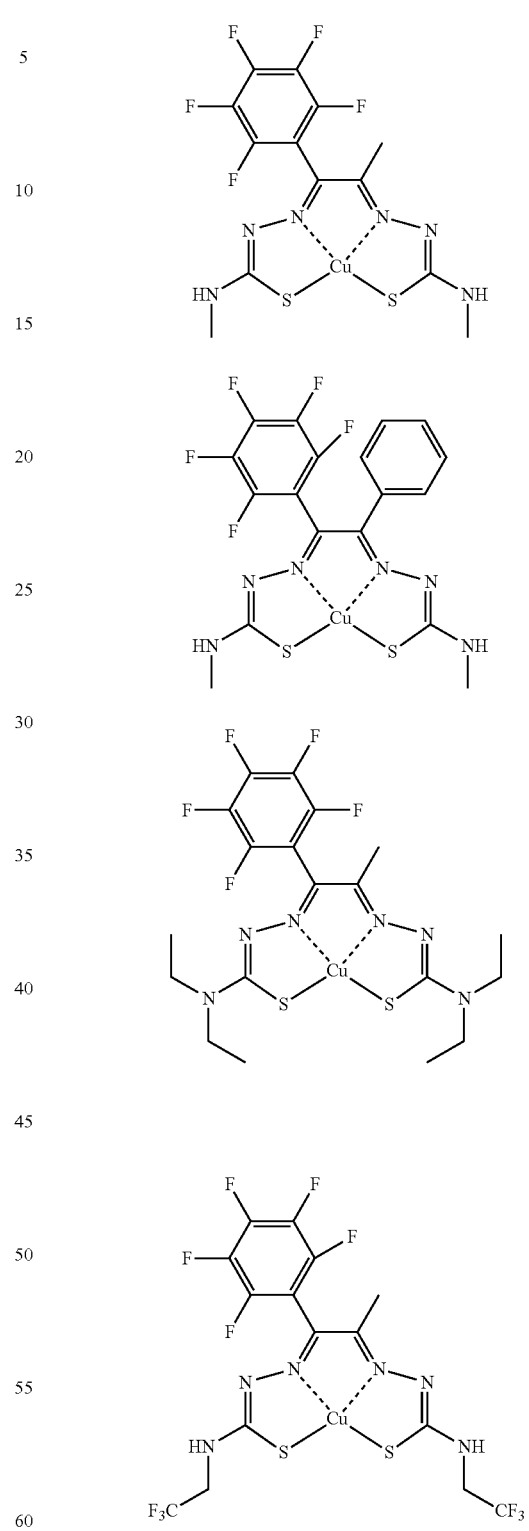
Representative embodiments of compound embodiments comprising groups that facilitate transport through a membrane are illustrated below. In some embodiments, the representative compounds can be the free ligand component of the complexes illustrated below.

TABLE 4
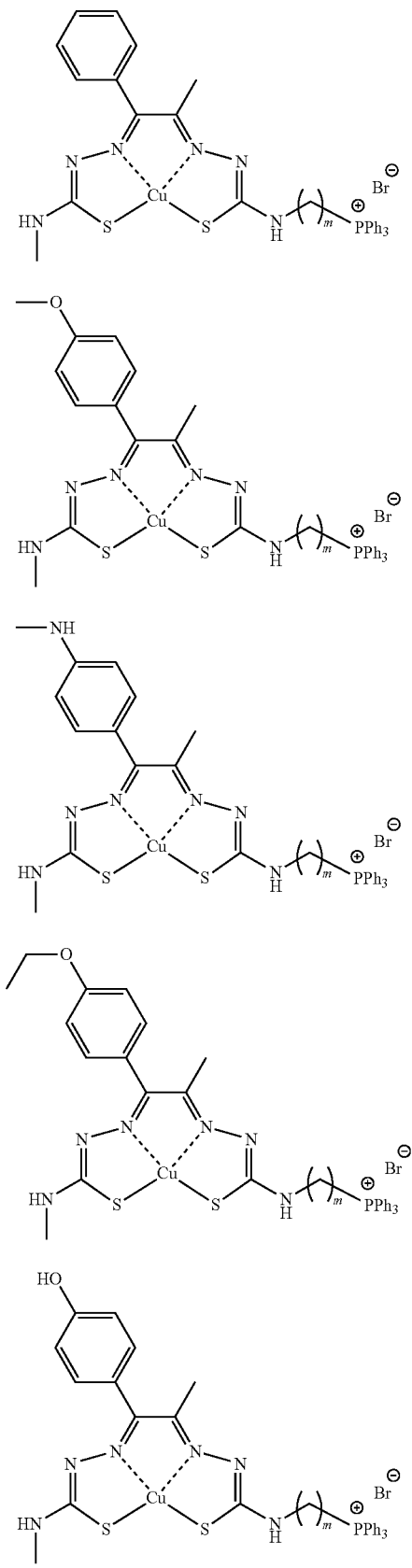
TABLE 4-continued
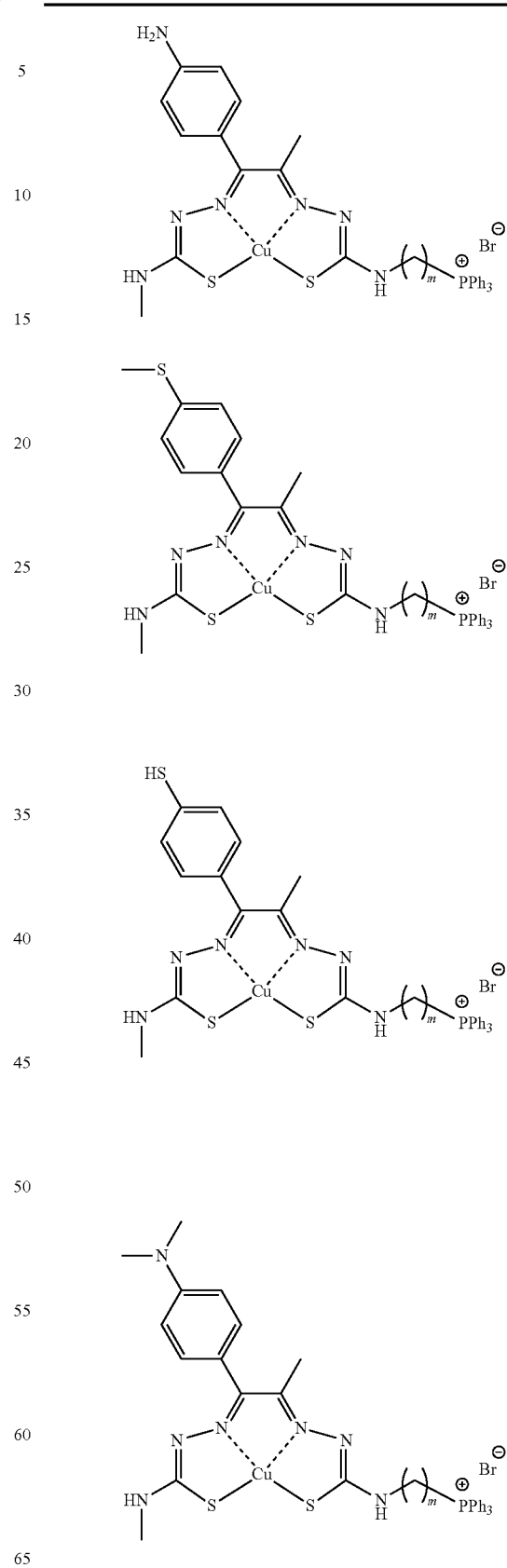

TABLE 4-continued
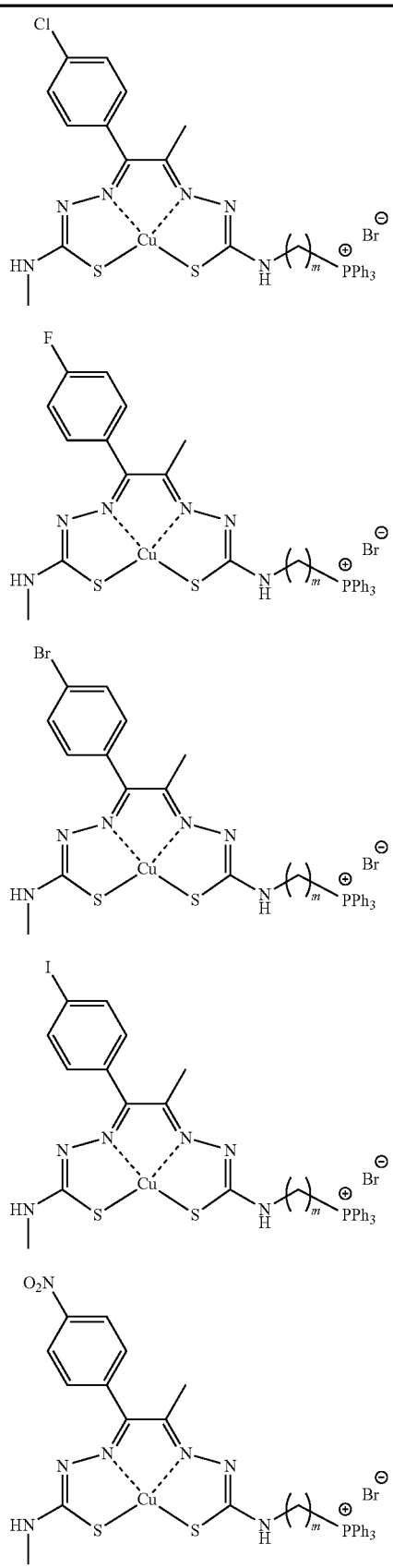
TABLE 4-continued
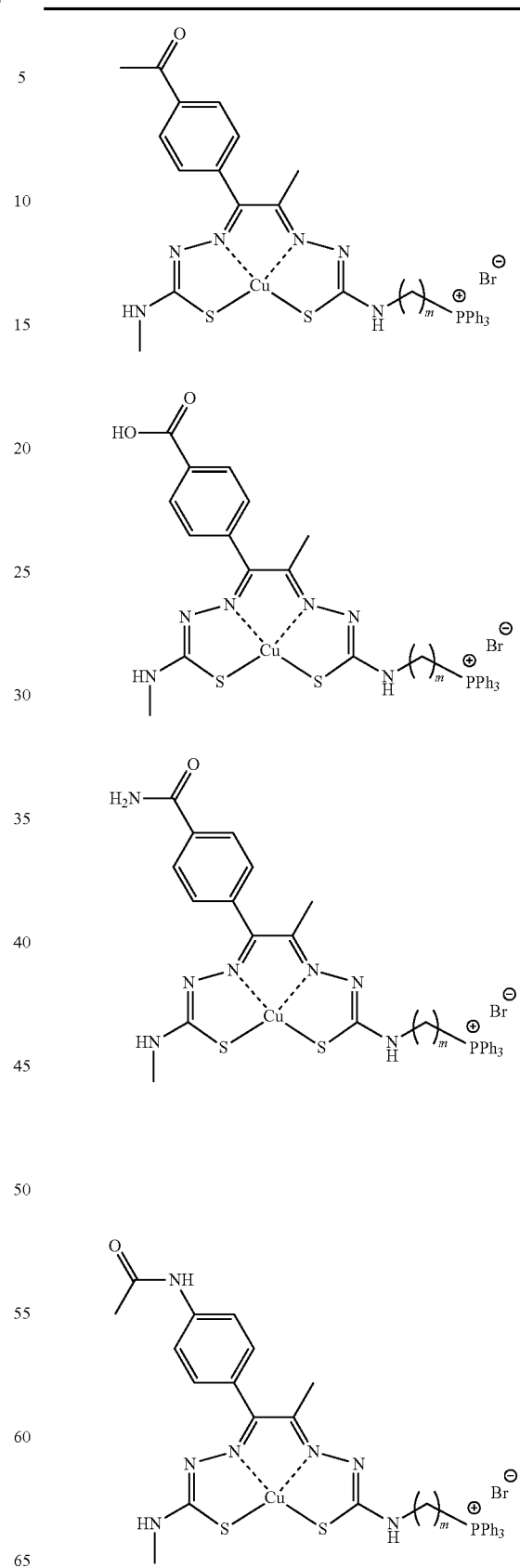

TABLE 4-continued
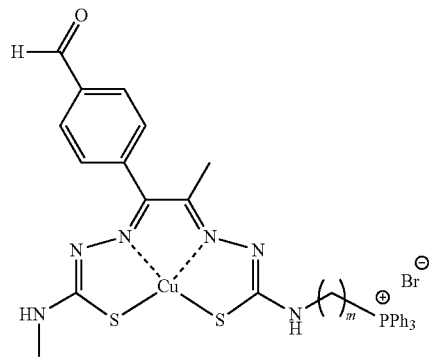
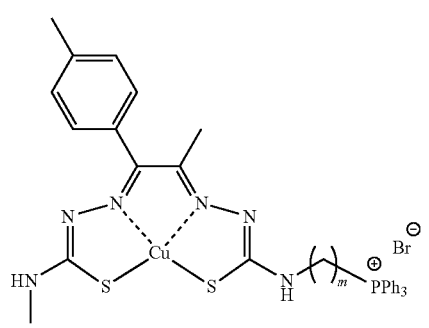
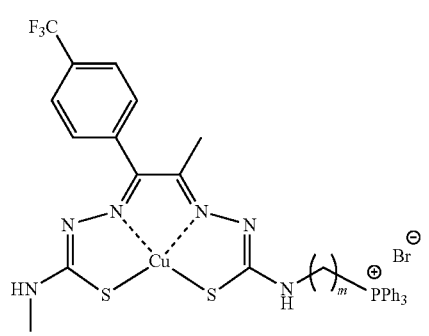
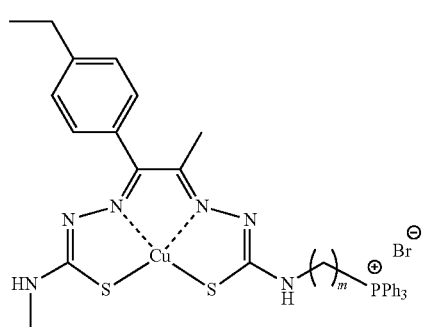
TABLE 4-continued
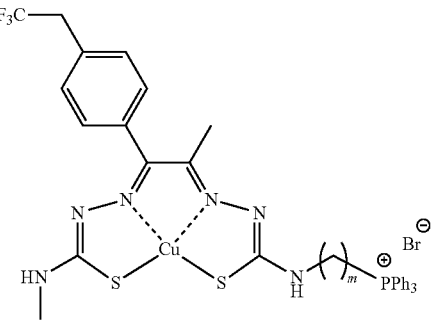
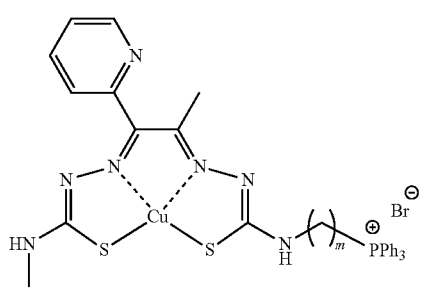
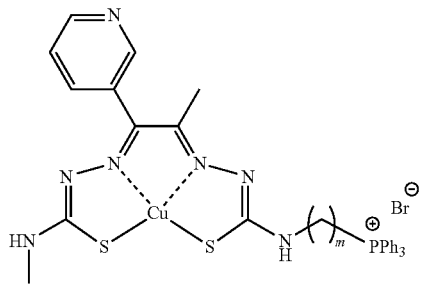
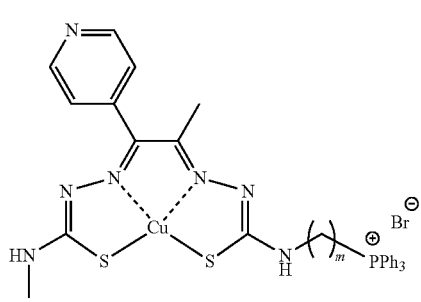
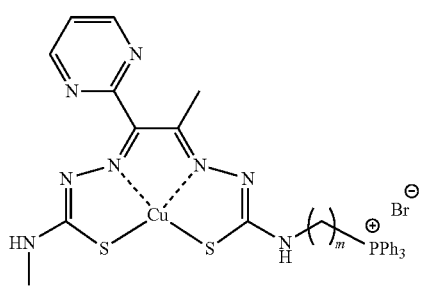

TABLE 4-continued
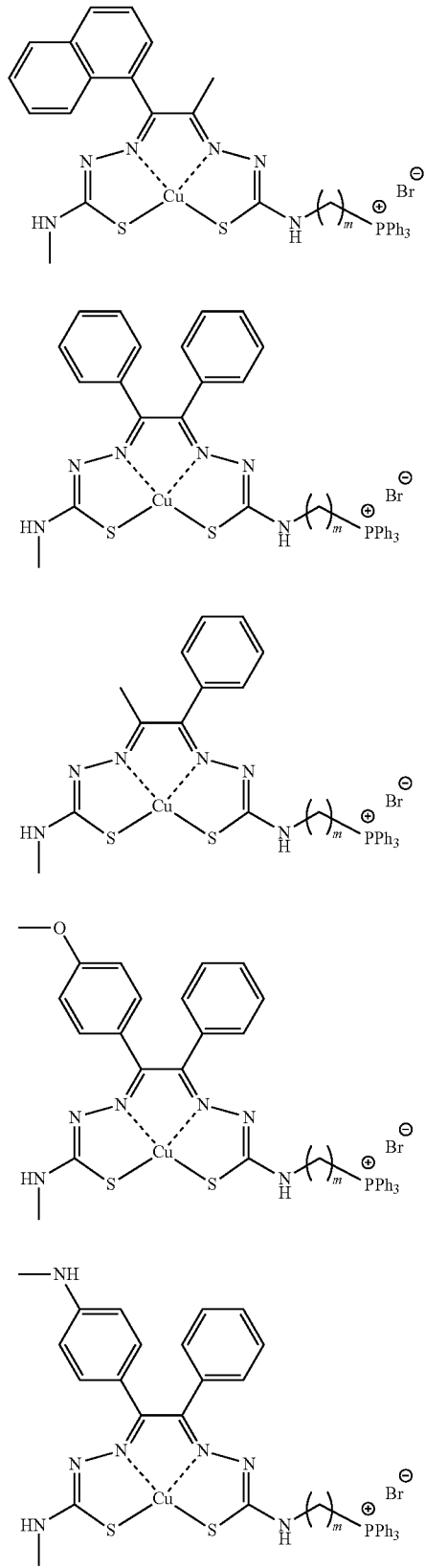
TABLE 4-continued
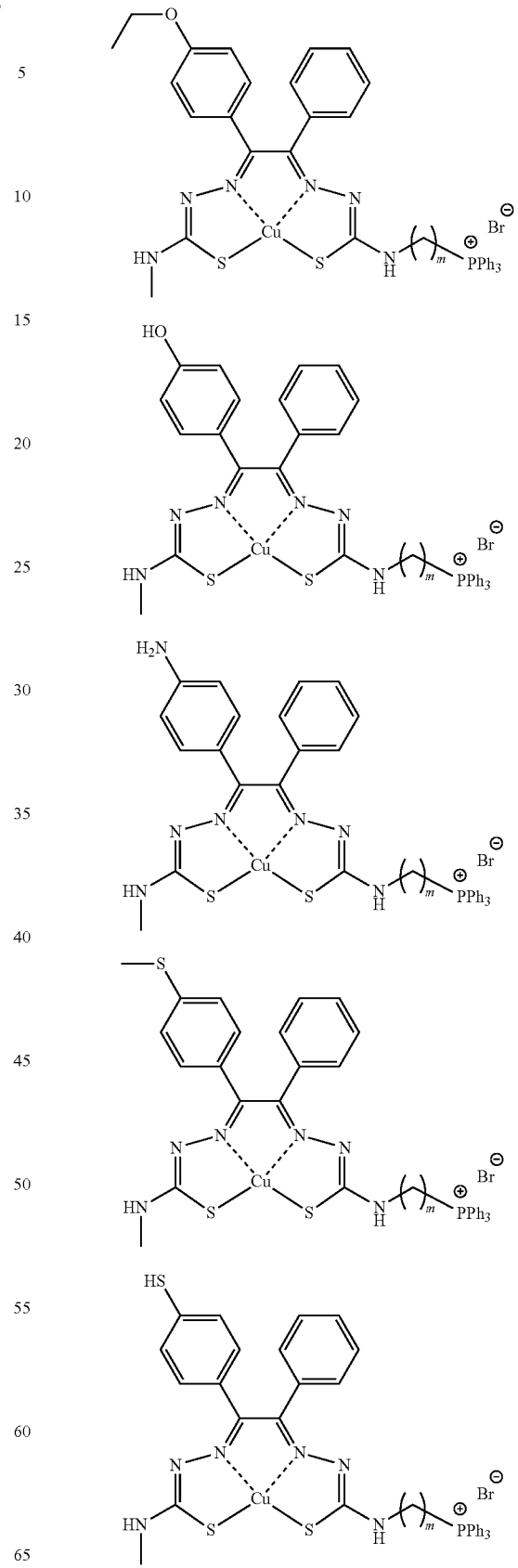

TABLE 4-continued
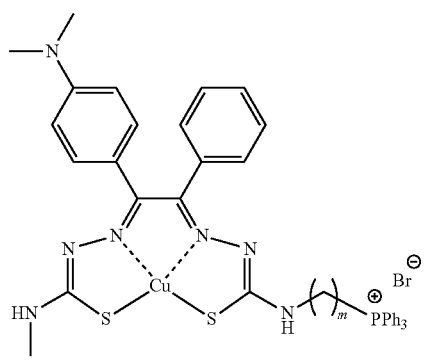
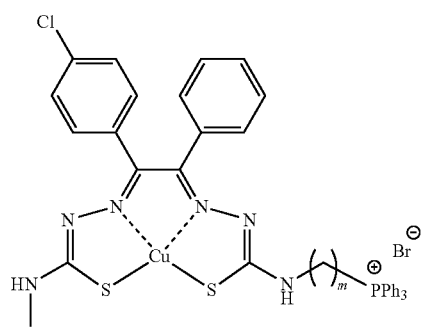
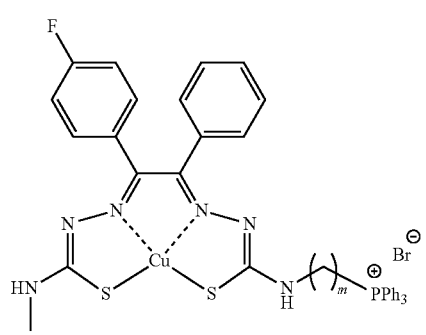
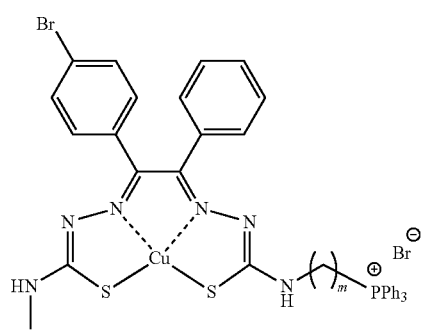
TABLE 4-continued
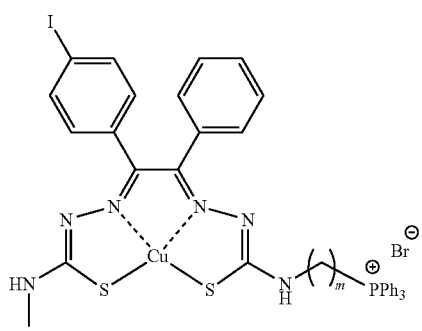
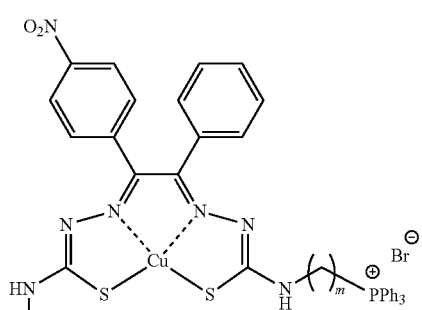
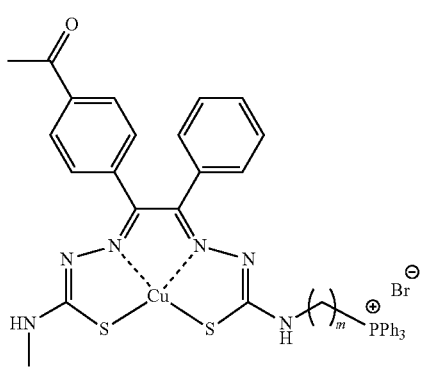
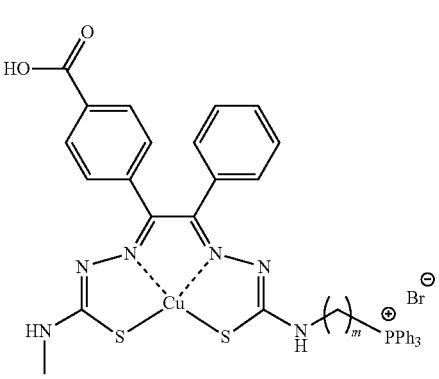

TABLE 4-continued
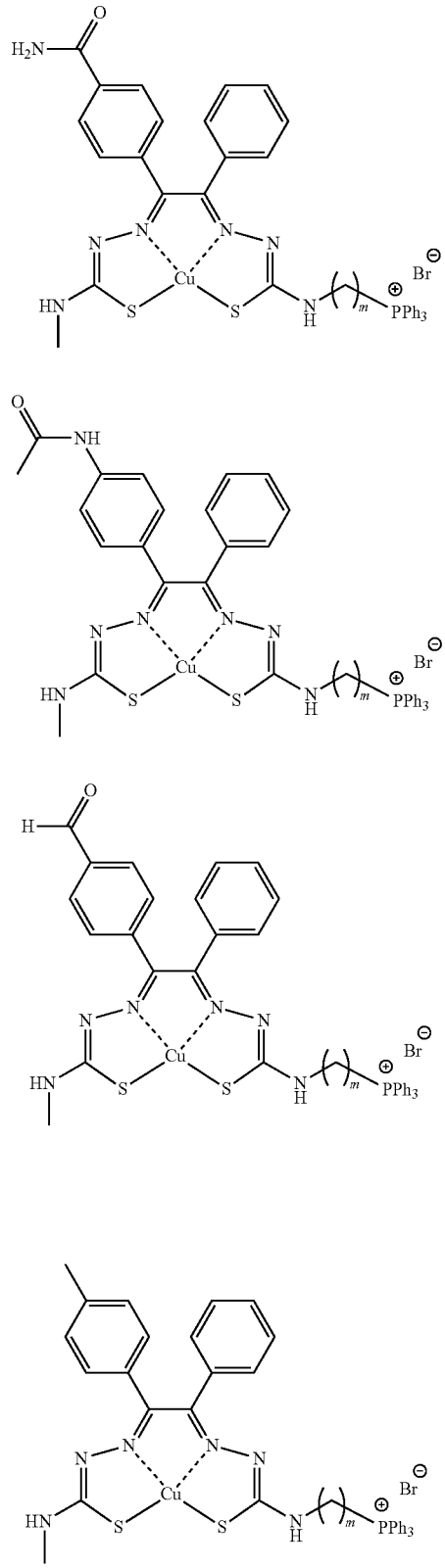
TABLE 4-continued
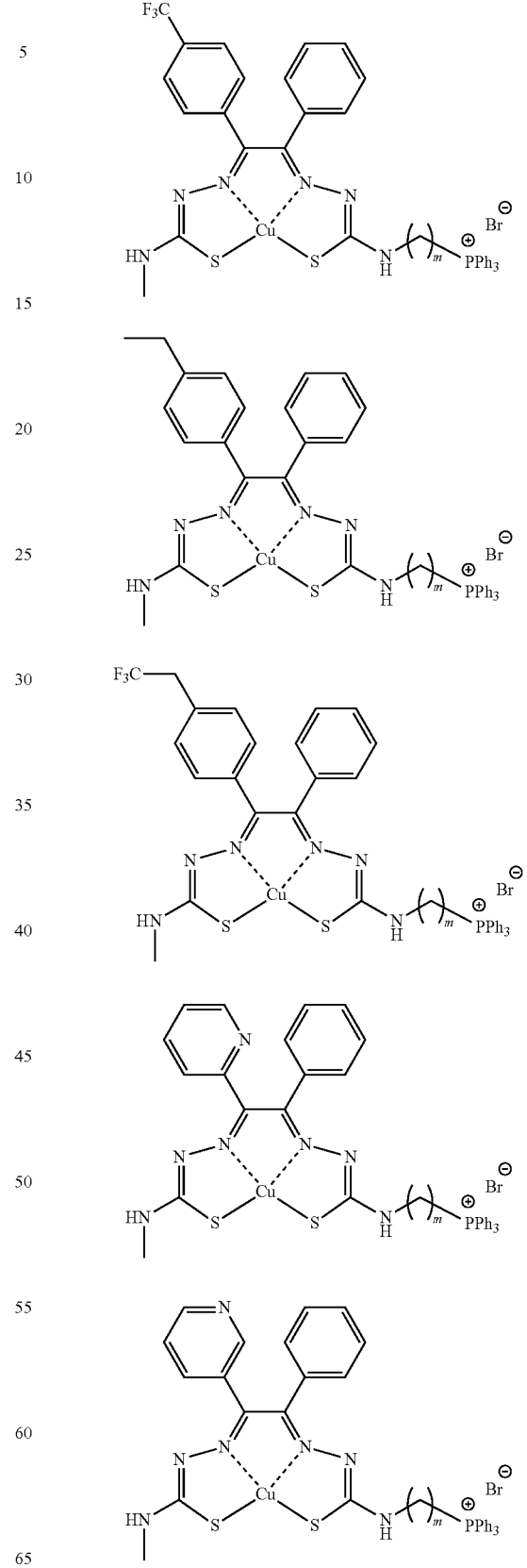

TABLE 4-continued
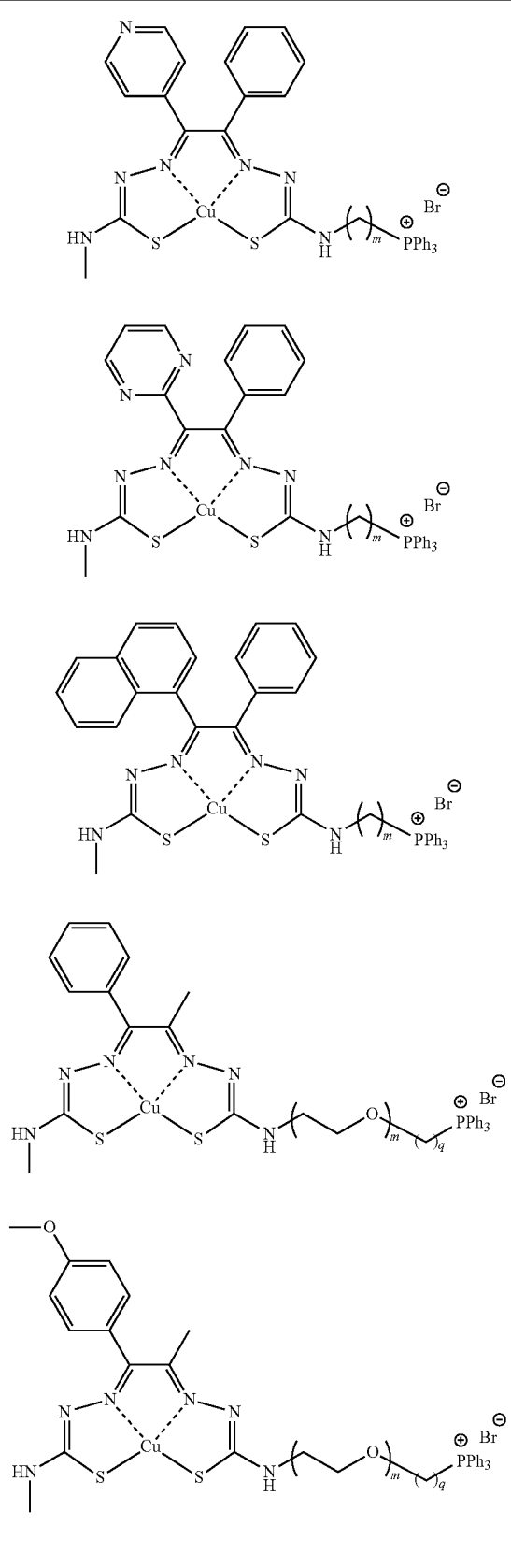
TABLE 4-continued
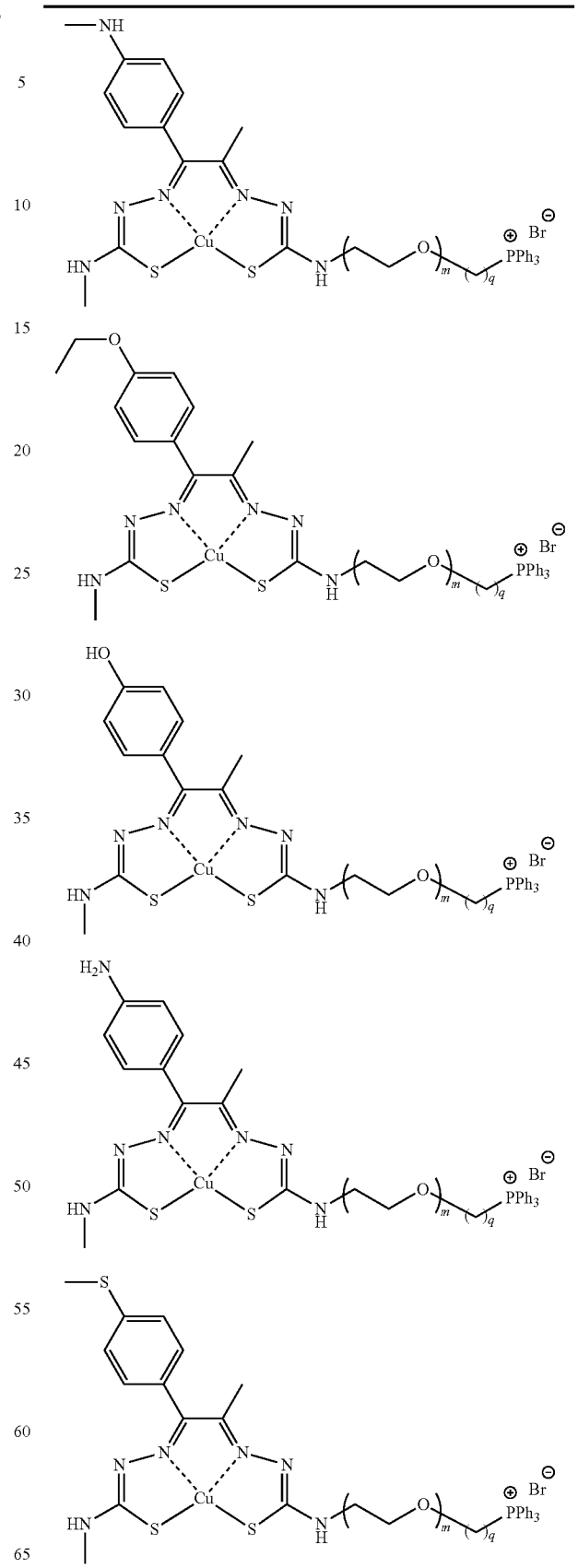

TABLE 4-continued
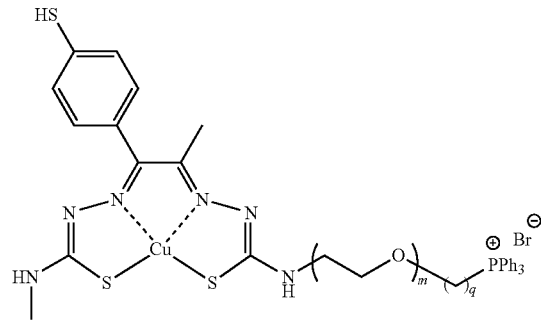
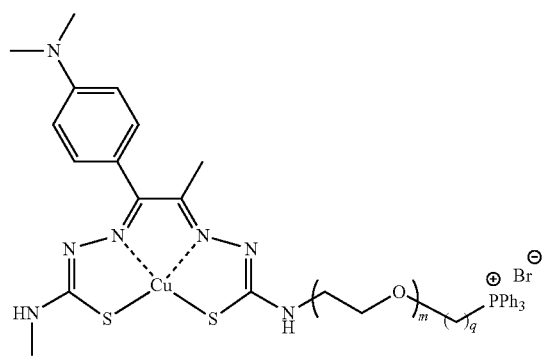
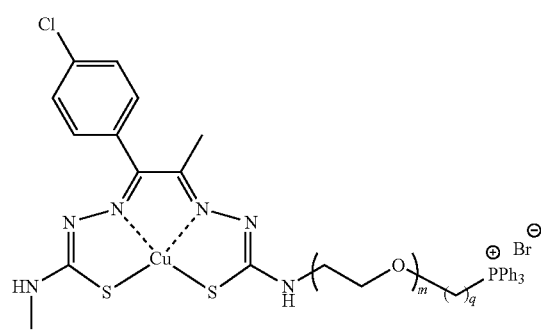
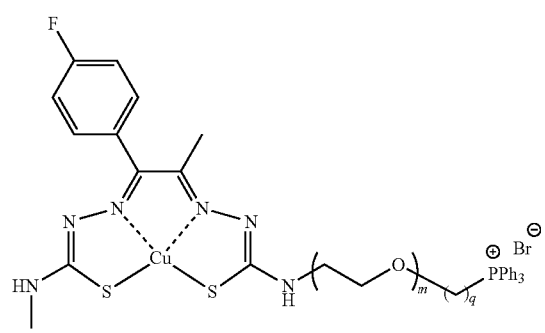
TABLE 4-continued
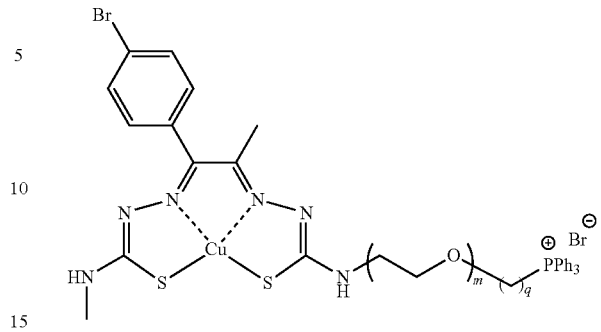
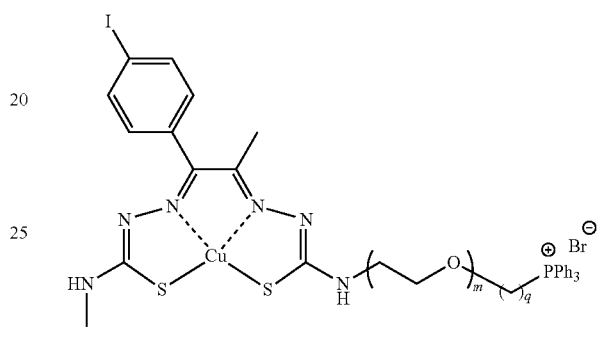
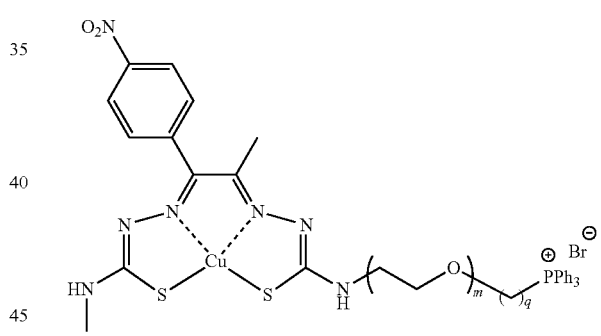
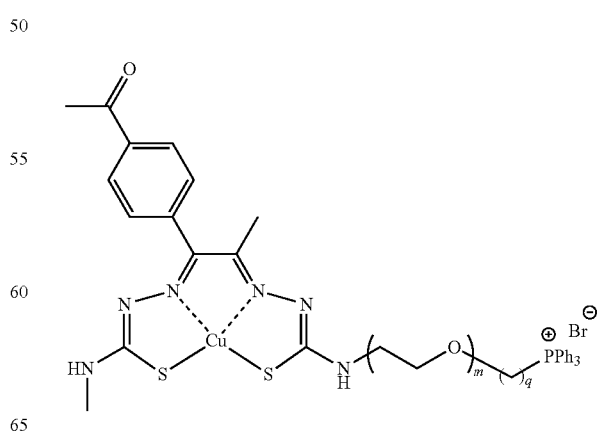

TABLE 4-continued
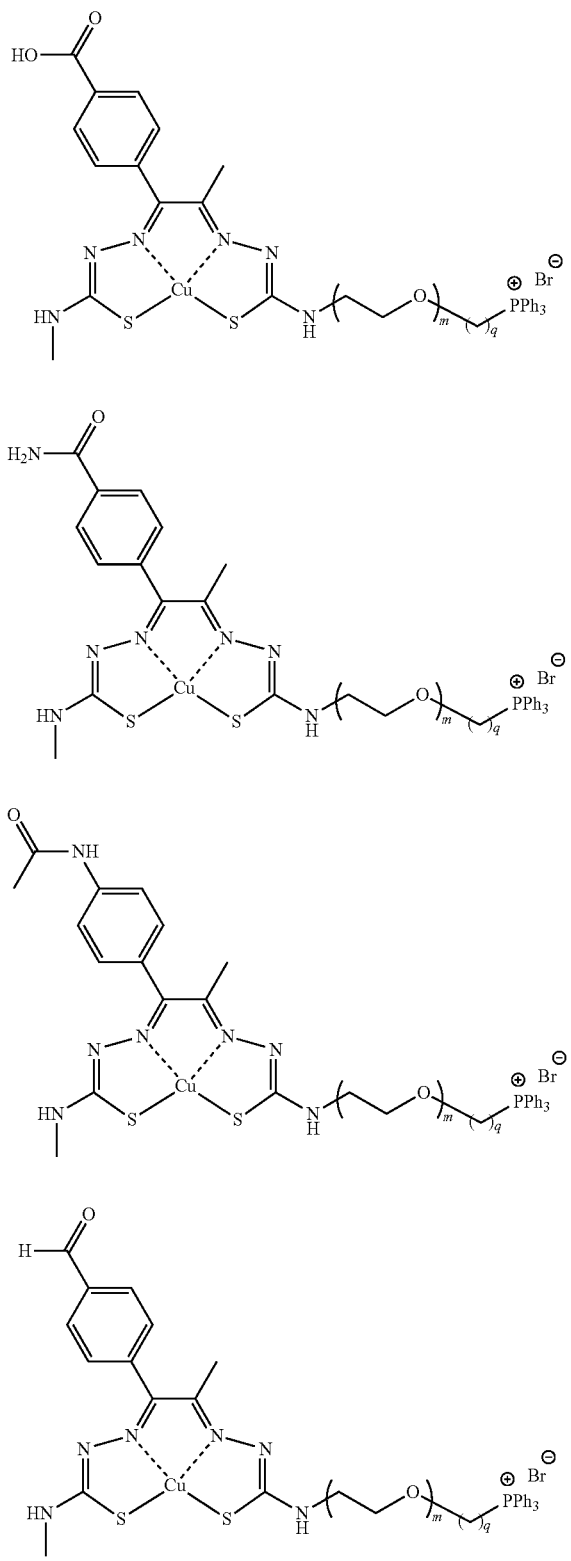
TABLE 4-continued
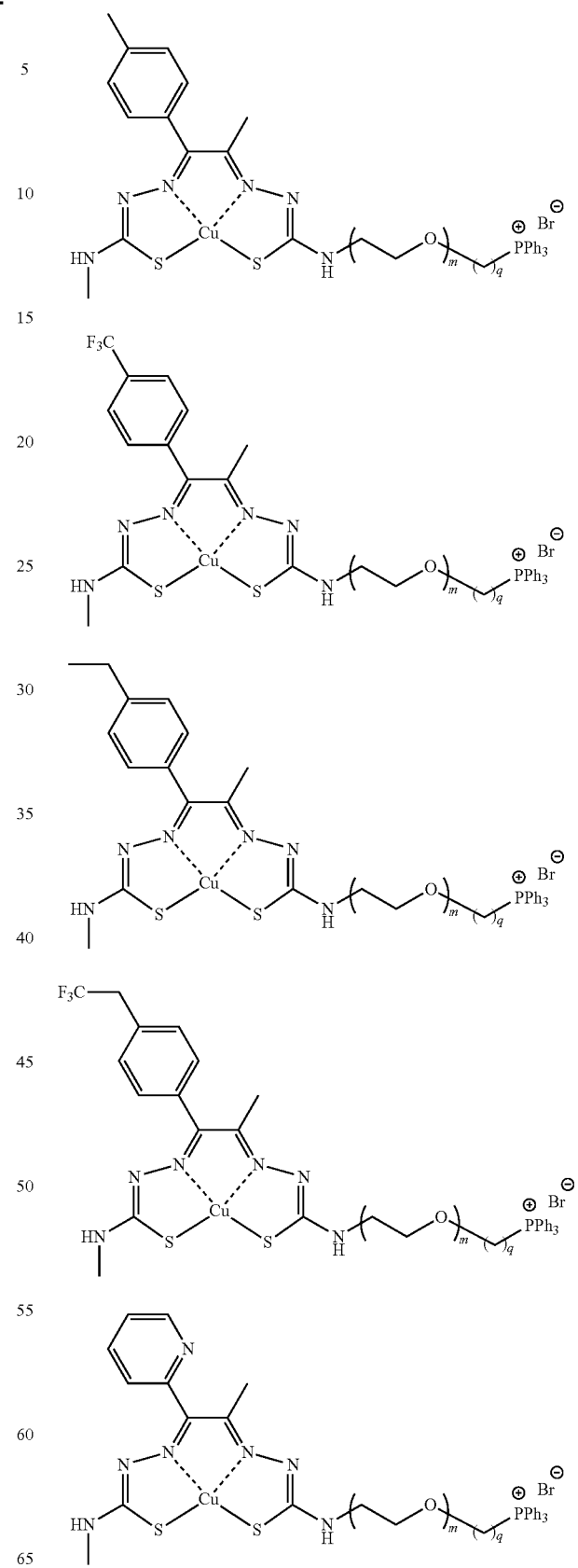

TABLE 4-continued
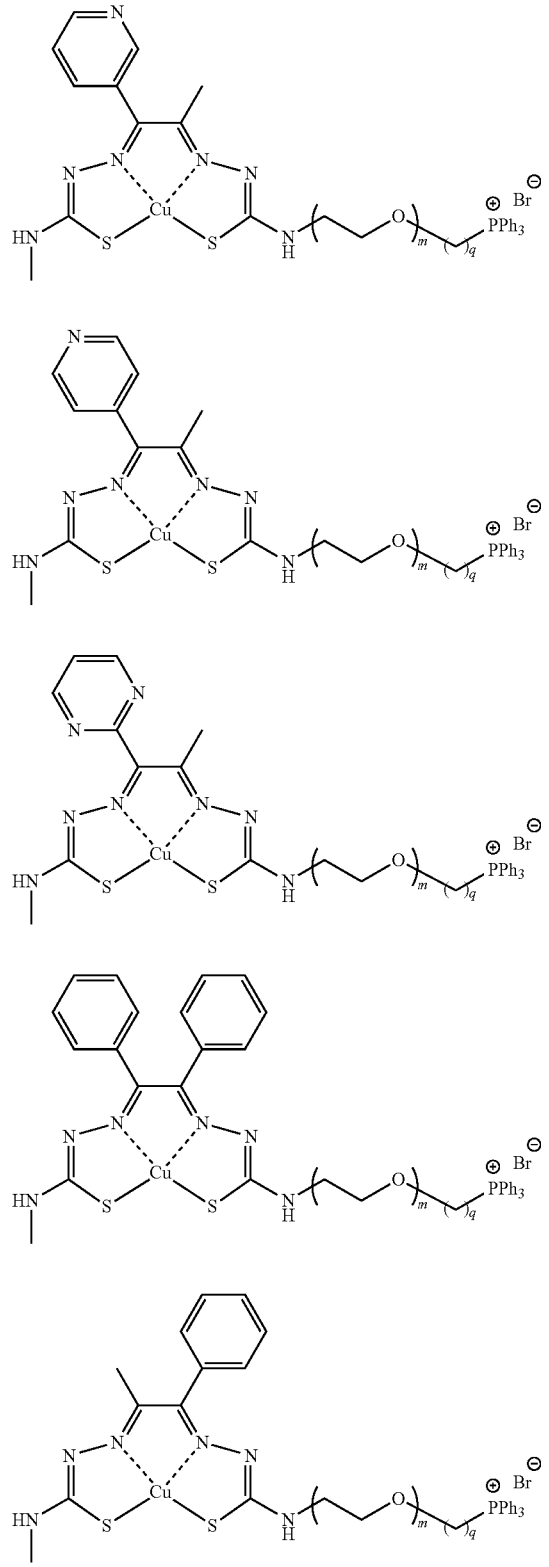
TABLE 4-continued
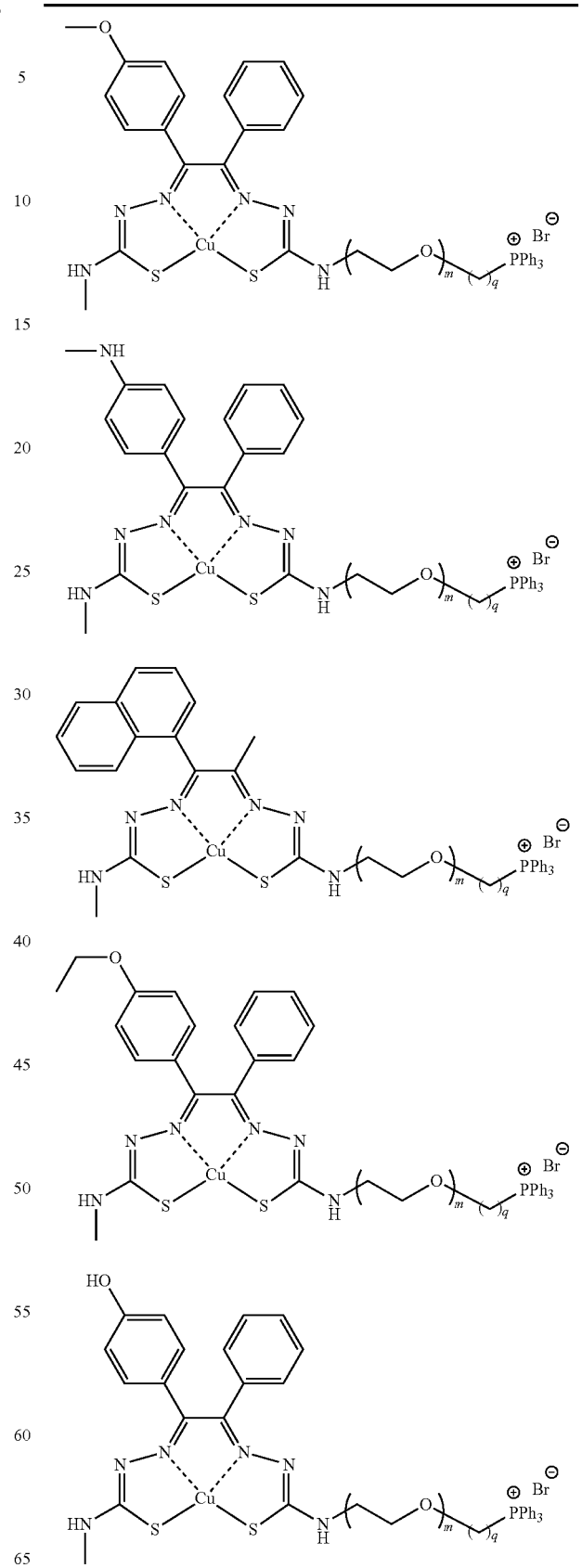

TABLE 4-continued
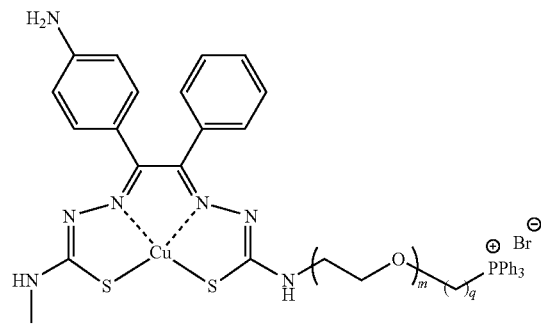
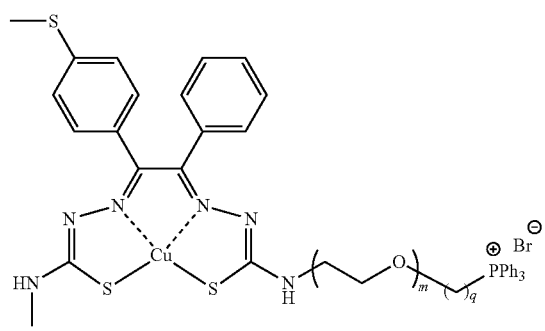
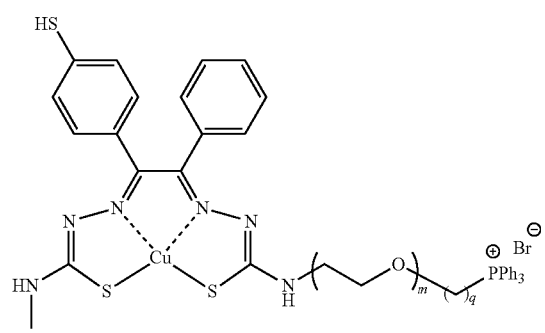
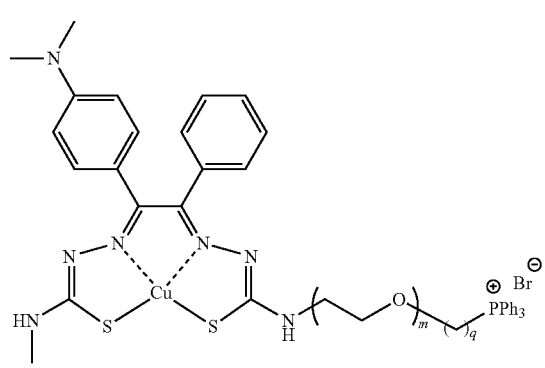
TABLE 4-continued
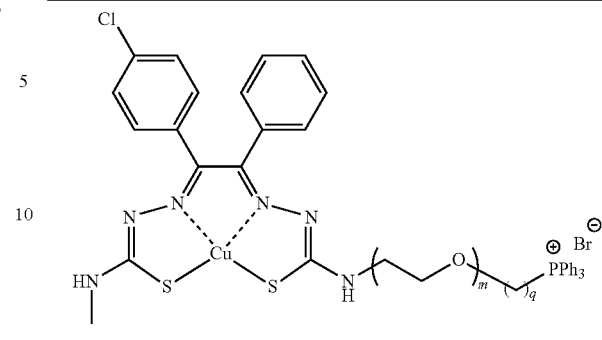
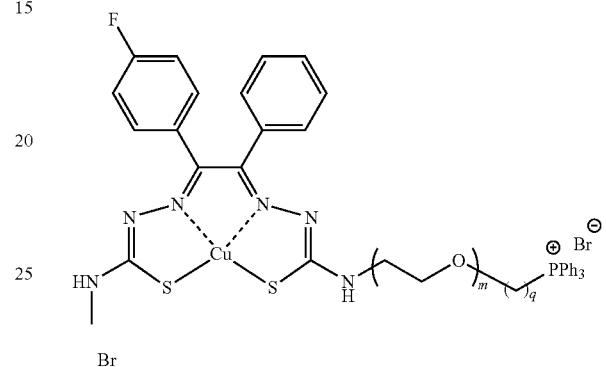
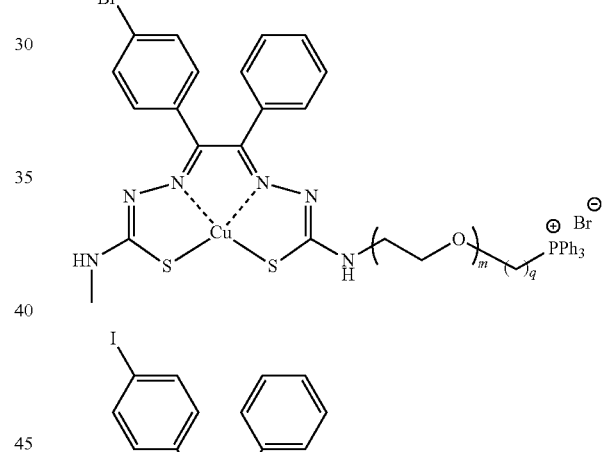
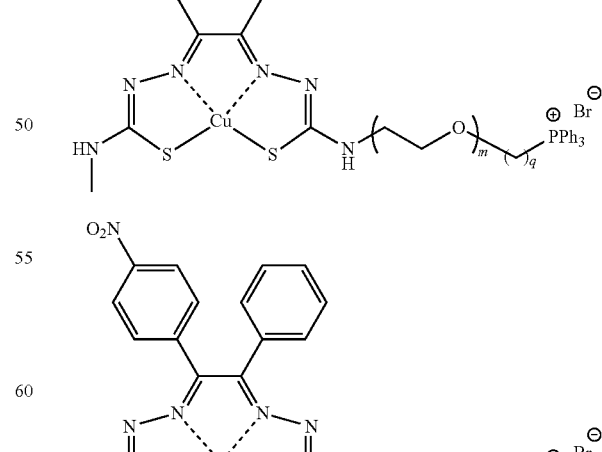

TABLE 4-continued
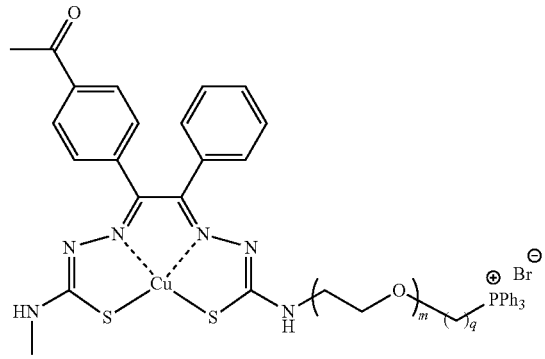
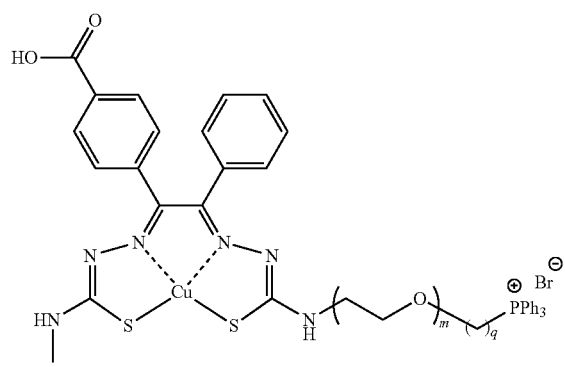
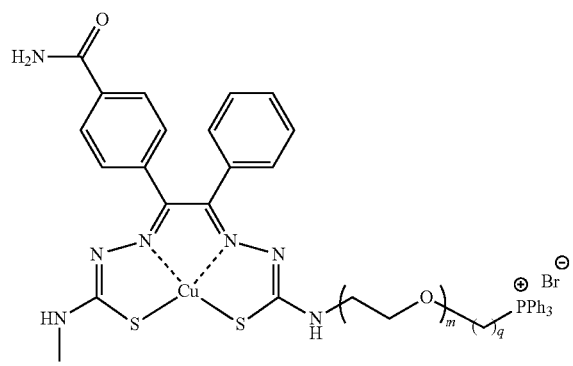
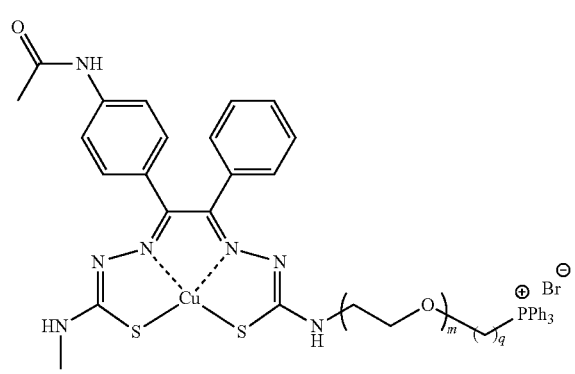
TABLE 4-continued
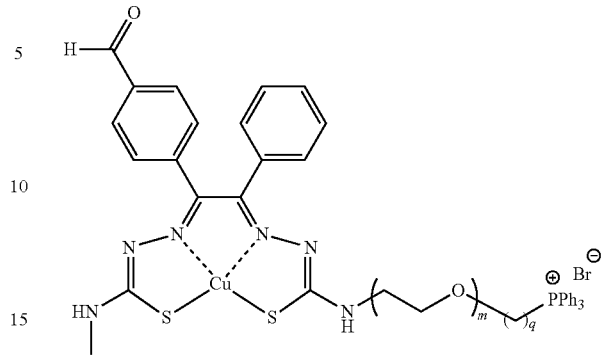
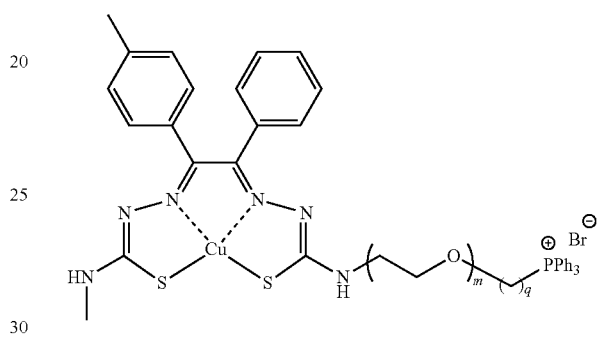
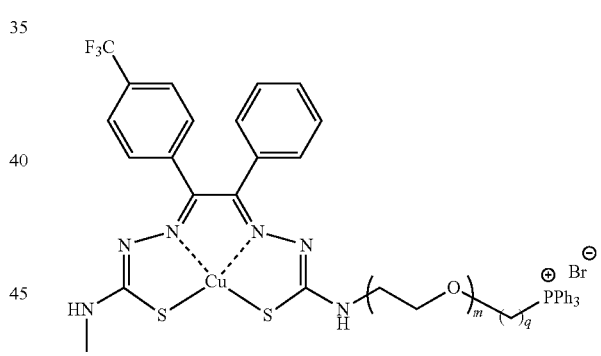
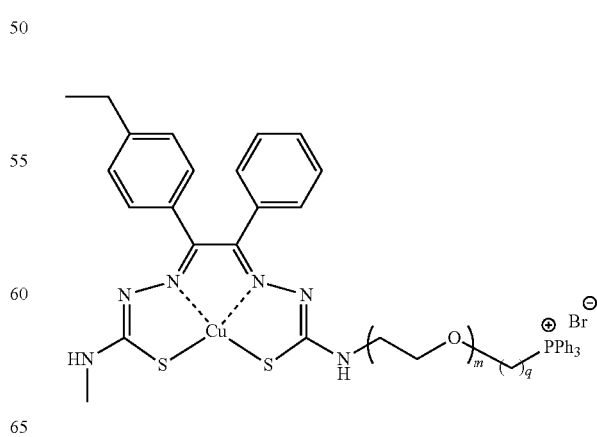

TABLE 4-continued
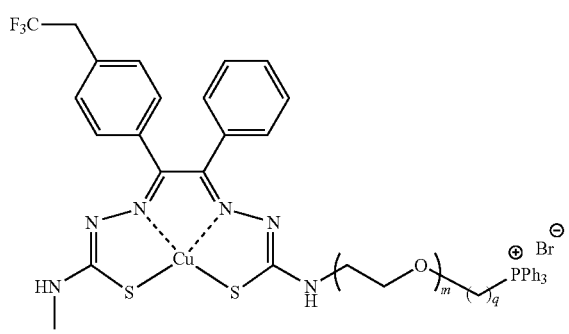
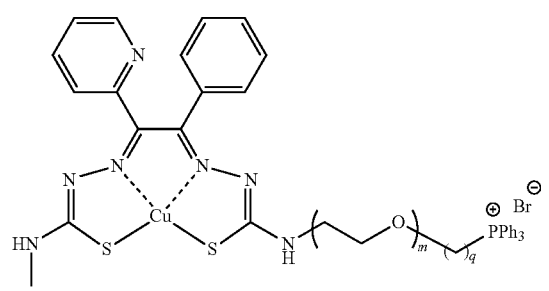
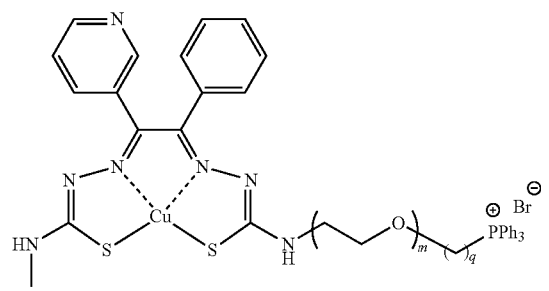
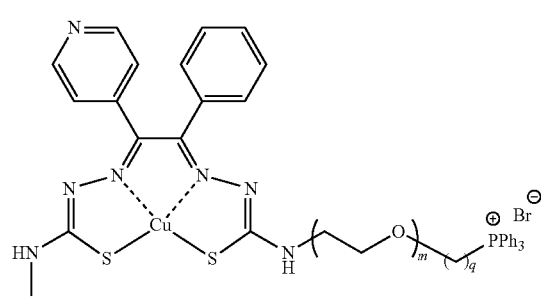
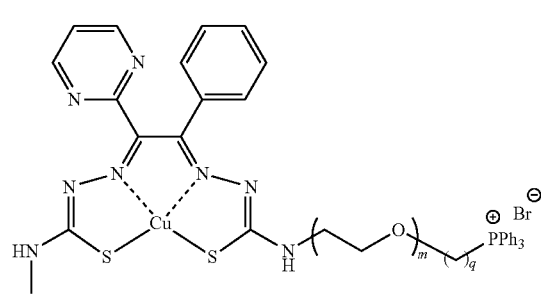
TABLE 4-continued
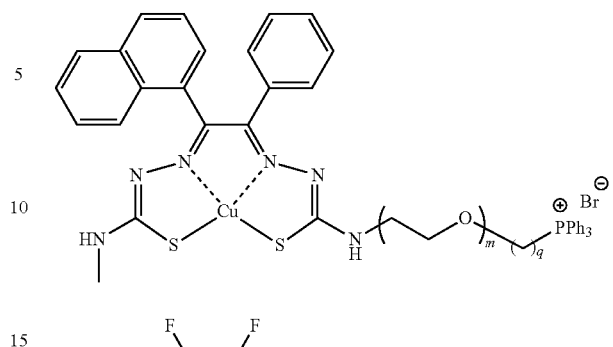
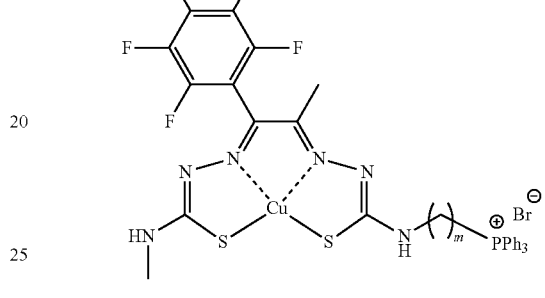
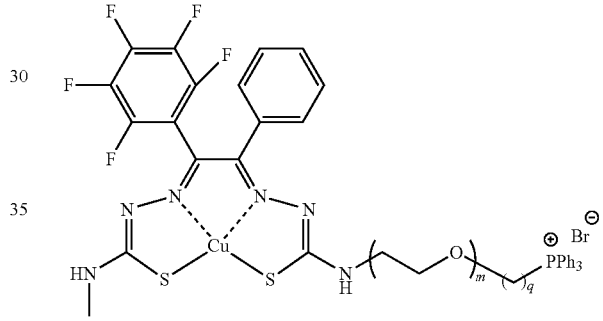
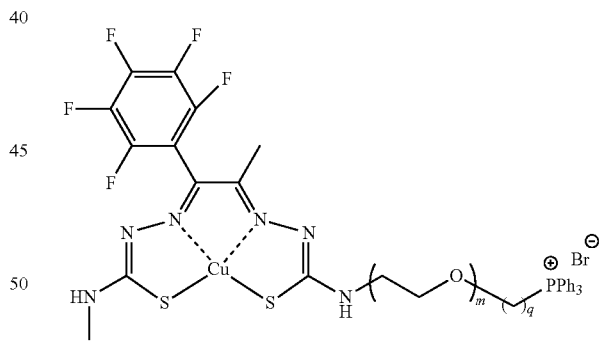
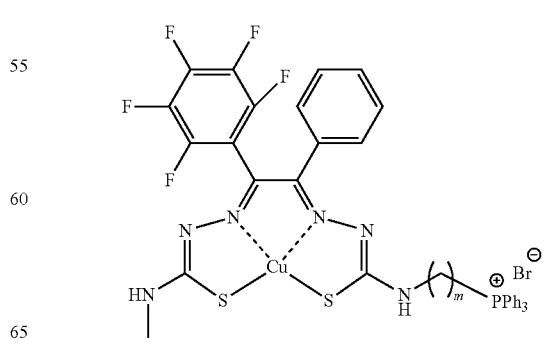

TABLE 4-continued

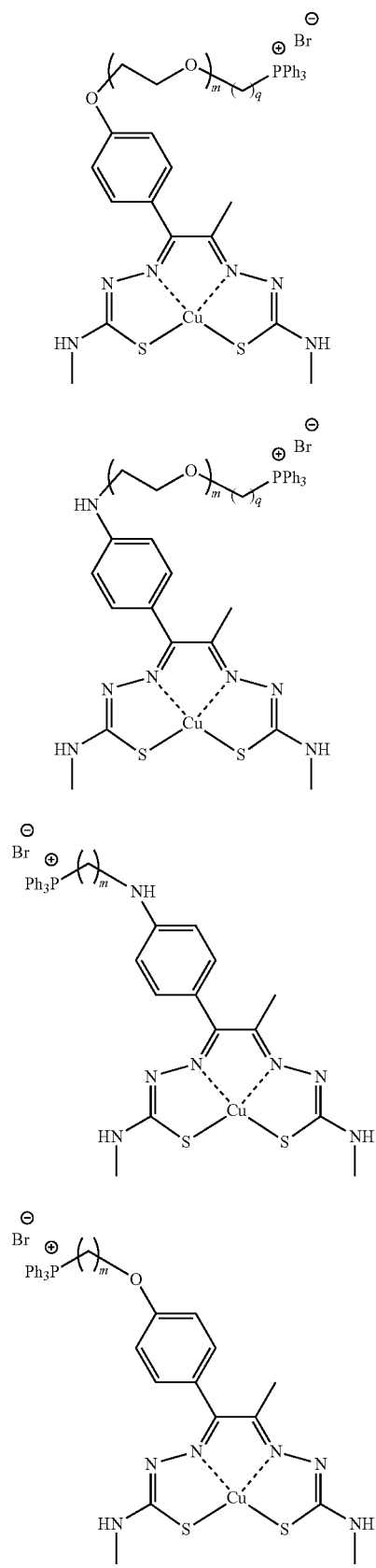

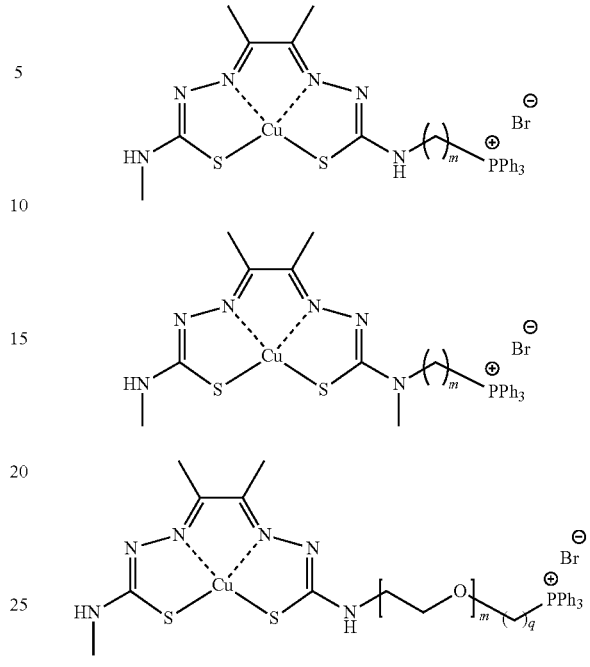

A bromide counterion is included for the compound embodiments above. A person of ordinary skill in the art will understand that other counterions may be used to form therapeutically active compounds with the scope of the present disclosure. In some embodiments, compound embodiments wherein the TPP group instead is a quaternary amine also are included in the present disclosure. With reference to the compound embodiments illustrated above, m can be as described for the formulas above and q can be an integer selected from 0 to 30, such as 1 to 20, or 1 to 10, or 1 to 5. In some embodiments, q can be 0, 1, 2, 3, 4, 5, 6, 7, 8, 9, or 10.

In an independent embodiment, the compound is not or is other than

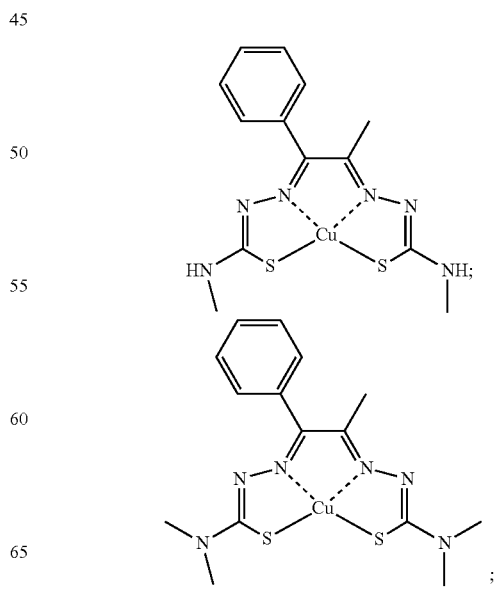

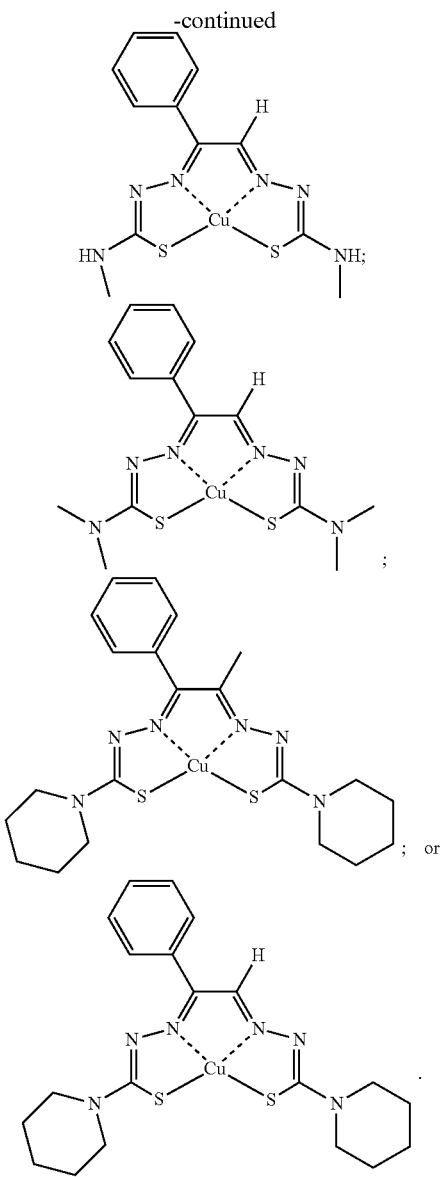

In yet another independent embodiment, if $R^1$ is methyl and $R^2$ is methyl or hydrogen, then at least one of $R^2$, $R^3$, or $R^4$ comprises a linker-X group as described herein.

IV. Method of Use

The compound embodiments described herein are therapeutics useful for treating neurological diseases (e.g., motor neuron diseases), other copper deficiency-related diseases, and/or mitochondrial deficiencies (e.g., cytochrome c oxidase deficiency). Examples of neurological diseases and motor neuron diseases that can be treated using the compound embodiments and methods described herein include, but are not limited to, ALS, Parkinson's disease, Lou Gehrig's disease, primary lateral sclerosis, Kennedy's syndrome, frontal temporal dementia associated with ALS, spinal muscular atrophy, Menke's disease, Alzheimer's disease, Huntington's disease, multiple sclerosis, neuropathies, Prion disease, and any other neurological disease associated with copper deficiency. In additional embodiments, the compound embodiments disclosed herein can be used to treat canine copper deficiency-related diseases, such as canine degenerative myelopathy, ALS-like canine diseases, and the like. In exemplary embodiments, the compound embodiments are used to treat ALS, Parkinson's disease, Menkes disease, Lou Gehrig's disease, Kennedy's syndrome, frontal temporal dementia associated with ALS, spinal muscular atrophy, primary lateral sclerosis, and canine degenerative myelopathy.

In some embodiments, the method can comprise administering an effective (or a therapeutically effective) amount of one or more of the disclosed compound embodiments to a subject or a sample (e.g., a biological sample, such as a blood, tissue, or cell sample). In some embodiments, the method can further comprise monitoring the subject for changes in neurological function (e.g., monitoring the subject for evidence of motor neuron degeneration, muscular atrophy, and the like). In some embodiments, the compound can be administered using a pharmaceutical formulation of the compound, which can comprise the compound and a pharmaceutical dosage form. Any suitable pharmaceutical dosage form, such as those described below, can be used. In particular disclosed embodiments, the pharmaceutical dosage form is a transdermal patch, a tablet, a capsule, a lotion, or an injectable solution. In yet additional particular embodiments, the compound can be taken orally as a solid dispersant or it can be administered using percutaneous endoscopic gastrostomy for subjects that cannot be fed orally.

In some embodiments, the compound embodiments described herein stabilize the Cu,Zn SOD protein in ALS-affected tissues at rates and levels not achieved by other metal complexes known in the art, such as CuATSM. The compound embodiments described herein deliver metals (e.g., copper) into the CNS more rapidly than conventional agents and effectively stabilize SOD, thereby preventing the toxicity from mutations of this protein typically present in subjects disposed to developing ALS or other neurological diseases. Each subunit of SOD contains both copper and zinc, which have important catalytic and structural roles in stabilizing the SOD protein. Copper is used for enzyme activity and zinc can determine the folding of SOD. Intracellular copper also is bound primarily in cytochrome c oxidase. As a consequence, SOD often accumulates as a zinc-containing, copper-deficient form waiting to interact with its CCS. The intracellular delivery of copper to these two enzymes is provided by a complex network of copper transporters and chaperones, and the net distribution is driven by the relative affinity gradients for copper. SOD and CCS have the highest affinity for copper in the CNS. Because zinc strongly stabilizes unfolded SOD protein, the immature SOD accumulates in the spinal cord awaiting copper from CCS to complete Cu,Zn SOD formation. Copper transport into other organs is much faster than into the spinal cord and brain and thus the accumulation of copper-deficient SOD is typically higher in the CNS. In some embodiments, the method can comprise administering a compound embodiment to a subject that carries one or more mutations to a superoxide dismutase gene. In particular disclosed embodiments, the mutation is not or is other than a mutation at a G85, H46, or H48 residue of the superoxide dismutase gene. Such mutations affect the copper binding site and thus negate the protective effects of SOD.

Mouse and rat models of ALS produced by the overexpression of mutant SOD correlate to the human disease with higher fidelity than rodent models based on other more recently discovered ALS-associated mutations. Mutant SODs confer a toxic gain of function that leads to motor neuron degeneration in a variety of subjects, such as humans, dogs, mice, rats, zebrafish, and *Drosophila*. The toxic gain-of-function involves partially unfolded intermediates of SOD that lack the two metal cofactors that stabilize SOD. The high-expressing SOD$^{G93A}$ mouse model, in particular, has become the model most widely used by experts in evaluating treatments for neurodegenerative diseases. The symptoms of ALS become clear in these mice around 100 days as the mice lose weight and their hind limbs atrophy before reaching a terminal paralysis at 130 days. As such, this model is well-accepted as a model that is reasonably correlated with outcomes for treating neurological diseases, such as ALS and other motor neuron diseases, in human subjects.

While it is known in the art that a common feature to ALS-causing mutations is to disrupt copper and zinc binding to the SOD protein, there is an unmet need in the field of ALS treatment for an effective therapy in subjects. Few treatments in the art have been able to extend life by more than 10-15% in the high-expressing SOD$^{G93A}$ mice and no pharmaceutical agent has been successfully translated into human treatments. While there is growing evidence that CuATSM is effective in treating ALS in human subjects, this particular compound has other drawbacks associated with its structure as discussed above. The compound embodiments described herein, however, are able to exhibit superior activity to CuATSM and the CuGTSM and CuPTSM derivatives as the compound embodiments described herein transfer metals (e.g., copper) at rates that are not achieved by CuATSM, CuGTSM, or CuPTSM and further do not include the challenges faced with these complexes (e.g., solubility issues, pharmaceutical formulation issues, and synthesis issues).

The low reduction potential or, phrased differently, the high copper affinity of the ATSM ligand for cupric ion (in the 2+ ionization state) prevents copper release in most tissues, but allows selective release of copper in hypoxic tissues or in cells with damaged mitochondrial electron transport chains; however, even slight modifications of the CuATSM compound (e.g., removing one or both methyl groups from the carbon atoms of the diimine functional groups) results in rapid copper release that can result in toxicity in SOD ALS models. As such, while CuATSM exhibits high copper affinity, it is an inefficient delivery vehicle to bypass the distribution system naturally limiting copper transport into the CNS. Continued treatment thus is necessary to provide sufficient copper for CCS to complete the maturation of Cu,Zn SOD. But, such continued treatment also has the potential to cause toxicity due to greater copper intake. Furthermore, given the negative reduction potential of CuATSM, it is very difficult to reduce, which is reflected in the slow efficacy in replenishing SOD and COX extending over weeks. As a consequence, the majority of CuATSM (e.g., >95%) is eliminated in urine with copper still bound. In contrast, reduction potentials of compound embodiments disclosed herein allow the compounds to be reduced easier than CuATSM, but still exhibit superior efficacy in treating SODxCCS mice and also avoid potentially toxic release of copper intracellularly. See, for example, FIG. 3, which illustrates reduction (left) versus oxidation standard potentials (right) for ligand components (as determined in anhydrous DMSO). Also, compound embodiments described herein are able to exhibit activity that surpasses that of CuATSM and other ALS treatments. For example, in some embodiments, compound embodiments disclosed herein were able to keep mice alive for at least 10 or more months, as compared to 4 to 5 months achieved using conventional treatments. Disclosed compound embodiments also are able to deliver four or more times the amount of copper that CuATSM can deliver over a two week period (e.g., see FIG. 4).

Certain compound embodiments described herein also can be used for radioimaging. For example, compound embodiments comprising radioactive metal isotopes can be used as imaging agents. In some embodiments, such imaging agents can comprise a structure satisfying any one of the formulas described herein and wherein the complexed metal "M" is selected from a radioactive isotope of copper, iron, palladium, cadmium, or manganese. In some embodiments, compound embodiments comprising radioactive metals can be used in combination with positron emission tomography ("PET") to image a subject. In exemplary embodiments, the metal is radioactive copper, typically selected from $^{60}Cu^{2+}$, $^{61}Cu^{2+}$, $^{62}Cu^{2+}$, or $^{64}Cu^{2+}$, or any combination thereof. In some embodiments, the method can comprise administering the imaging agent to a subject or a sample and, in some additional embodiments, the method can further comprise exposing the subject or the sample to a PET scan.

In particular disclosed embodiments, the compound embodiments disclosed herein can be administered to a subject, such as a human or non-human animal. In some embodiments, the compound embodiments can be formulated as a pharmaceutical formulation. Pharmaceutical formulations contemplated by the present disclosure can include, but are not limited to, pharmaceutical formulations comprising at least one compound embodiment disclosed herein, and a pharmaceutically-acceptable excipient selected from, for example, an adjuvant, a carrier, a stabilizer, or combinations thereof. The pharmaceutical formulations also can include additional components, such as diluents, fillers, binding agents, moisturizing agents, preservatives, acids, and the like, and any and all combinations thereof. The compound embodiments described herein may be used alone, in combination with one or more additional compounds, or as an adjunct to, or in combination with, an established therapy. In some embodiments, the compound embodiments may be used in combination with other therapeutic agents useful for the disorder or condition being treated. Exemplary other therapeutic agents that can be used for treating the diseases/conditions described herein include, but are not limited to, edaravone and riluzole. These compounds may be administered simultaneously, sequentially in any order, by the same route of administration, or by a different route.

Pharmaceutical formulations comprising the compound embodiments disclosed herein can be administered as pharmaceutically acceptable formulations in the form of solids, liquids, and/or lotions. Suitable solid forms of administration include, but are not limited to, tablets, capsules, powders, solid dispersions, and the like. In particular disclosed embodiments, compound embodiments described herein are better suited for formulation by solid dispersant methods as compared to CuATSM. Compound embodiments disclosed herein have lower melting points than CuATSM (e.g., 50° C. to 80° C. lower, such as 50° C. to 70° C. lower, or 50° C. to 60° C. lower). Certain disclosed compound embodiments melt in the range of 140° C. to 180° C., such as 145° C. to 170° C., or 150° C. to 160° C. As such, the compound embodiments described herein can be formulated as solid dispersants and/or other solid dosage forms and thus can be administered orally, whereas CuATSM is not suitable for solid dispersant formulations or other solid dosage forms. In particular disclosed embodiments, the compounds described herein can be formulated in an oral dosage form wherein less than 25%, such as less than 20%, or less than 15%, or less than 10%, or less than 5% of a total amount of the compound crystalizes when combined with the pharmaceutical dosage form. Furthermore, CuATSM is not suitable for pill/tablet/capsule dosage forms as it gradually crystalizes out of matrices to form insoluble crystals. As indicated above, this can result in large amounts of CuATSM passing into the bowels and thus potentially cause gastrointestinal distress.

The compound embodiments disclosed herein also can be provided as liquid or lotion formulations in view of their propensity to resist crystallization. Suitable liquid or lotion forms include, but are not limited to, oil-in-water or water-in-oil emulsions, aqueous gel compositions, or liquids or lotions formulated for use as foams, films, sprays, ointments, pessary forms, suppository forms, creams, liposomes or in other forms embedded in a matrix for the slow or controlled release of the compound to the skin or surface onto which it has been applied or is in contact. In particular disclosed embodiments, such formulations can be included with a dermal patch to facilitate dosing of the compound.

Compositions comprising the compound embodiments or pharmaceutically acceptable components may be formulated so as to be suitable for a variety of modes of administration, including, but not limited to, topical, ocular, oral, buccal, systemic, nasal, injection (such as intravenous, intraperitoneal, subcutaneous, intramuscular, or intrathecal), transdermal (e.g., by mixing with a penetrating agent, such as DMSO), rectal, vaginal, etc., or a form suitable for administration by inhalation or insufflation.

For oral or buccal administration, the pharmaceutical formulations may take the form of lozenges, tablets or capsules prepared by conventional means with pharmaceutically acceptable excipients. The tablets or capsules may be coated by methods well known in the art with, for example, sugars, films, or enteric coatings.

Liquid preparations of the compound embodiments disclosed herein for oral administration may take the form of, for example, elixirs, solutions, syrups or suspensions, or they may be presented as a dry product for constitution with water or other suitable vehicle before use. Preparations for oral administration also may be suitably formulated to give controlled release of the compound.

For topical administration, the compound embodiments can be formulated as solutions, lotions, gels, ointments, creams, suspensions, etc. For transmucosal administration, penetrants appropriate to the barrier to be permeated can be used in the formulation.

Systemic formulations include those designed for administration by injection, e.g., subcutaneous, intravenous, intramuscular, intrathecal or intraperitoneal injection, as well as those designed for transdermal, transmucosal oral or pulmonary administration. Useful injectable preparations include sterile suspensions, solutions or emulsions of the compound in aqueous or oily vehicles. The pharmaceutical formulations may also contain formulating agents, such as suspending, stabilizing and/or dispersing agents.

For rectal and vaginal routes of administration, the compound embodiments or compositions thereof may be formulated as solutions (for retention enemas) suppositories or ointments containing conventional suppository bases, such as cocoa butter or other glycerides.

For nasal administration or administration by inhalation or insufflation, the compound embodiments and/or compositions thereof can be conveniently delivered in the form of an aerosol spray from pressurized packs or a nebulizer with the use of a suitable propellant. In the case of a pressurized aerosol, the dosage unit may be determined by providing a valve to deliver a metered amount. Capsules and cartridges for use in an inhaler or insufflator (for example capsules and cartridges comprised of gelatin) may be formulated containing a powder mix of the compound and a suitable powder base such as lactose or starch.

The dosage of compound embodiments as disclosed herein will depend on various factors, including the age, weight, general health, and severity of the condition of the subject being treated, as will be understood by a person of ordinary skill in the art with the benefit of the present disclosure. Dosage also may be tailored to the sex and/or species of the subject. Dosage, and frequency of administration of the compound embodiments will also depend on whether the compound embodiments are formulated for treatment of acute episodes of a condition or for the prophylactic treatment of a disorder. In some embodiments, a loading dosage can be used as an initial treatment for patients newly diagnosed or suspected of having a neurological disease. Loading dosages can be administered one, two, three, or more times per day. In some embodiments, loading dosages are administered up to four times per day for a period of time until sufficient amounts of copper have been delivered to the central nervous system/brain (e.g., such that amounts of copper ranging from 15 to 20 mg are continuously maintained in the central nervous system)s. In yet additional embodiments, a maintenance dosage or a prophylactic dosage can be administered, such as one time per day. The maintenance dosage typically provides enough copper needed by the CNS on a daily basis.

Effective dosages can be estimated initially from in vitro assays. For example, an initial dosage for use in subjects can be formulated to achieve a circulating blood or serum concentration of active compound that is at or above an $IC_{50}$ or $EC_{50}$ of the particular compound as measured in an in vitro assay. Dosages can be calculated to achieve such circulating blood or serum concentrations taking into account the bioavailability of the particular compound.

Dosage amounts, such as therapeutically effective amounts, of the disclosed compound embodiments or pharmaceutical formulations thereof will typically be in the range of from greater than 0 mg/kg/day (such as 0.0001 mg/kg/day, 0.001 mg/kg/day, or 0.01 mg/kg/day) to 100 mg/kg/day. In some embodiments, the dosage (or therapeutically effective amount) may range from 0.0025 mg/kg to 30 mg/kg or 0.0025 mg/kg to 1 mg/kg, administered at least once per day (such as from 0.01 mg/kg to 0.5 mg/kg or from 0.05 mg/kg to 0.15 mg/kg). The total daily dosage can range from 0.1 mg/kg to 5 mg/kg or to 20 mg/kg per day (such as from 0.5 mg/kg to 10 mg/kg per day or from 0.7 mg/kg per day to 2.5 mg/kg/day). In some embodiments, the dosage can be a loading dosage, which can include administering a compound (or pharmaceutical formulation thereof) in an amount ranging from 10 mg/kg/day to 100 mg/kg/day. In yet additional embodiments, the dosage can be a maintenance dosage, which can include administering a compound (or pharmaceutical formulation thereof) in an amount ranging from 1 mg/kg/day to 50 mg/kg/day. In yet additional embodiments, the dosage can be a prophylactic dosage, which can include administering a compound (or pharmaceutical formulation thereof) in an amount ranging from 0.1 mg/kg/day to 30 mg/kg/day.

In yet additional embodiments, such in particular embodiments for dosing human and/or canine subjects, dosage amounts, such as therapeutically effective amounts, of the disclosed compound embodiments or pharmaceutical formulations thereof will typically be in the range of from greater than 0 mg/day (such as 0.0001 mg/day, 0.001 mg/day, or 0.01 mg/day) to 100 mg/day. In some embodiments, the dosage (or therapeutically effective amount) may range from 0.0025 mg/day to 30 mg/day or 0.0025 mg/day to 1 mg/day, administered at least once per day (such as from 0.01 mg/day to 0.5 mg/day or from 0.05 mg/day to 0.15 mg/day). The total daily dosage can range from 0.1 mg to 5 mg or to 20 mg per day (such as from 0.5 mg/day to 10 mg/day or from 0.7 mg/day to 2.5 mg/day). In some embodiments, the dosage can be a loading dosage, which can include administering a compound (or pharmaceutical formulation thereof) in an amount ranging from 10 mg/day to 100 mg/day. In yet additional embodiments, the dosage can be a maintenance dosage, which can include administering a compound (or pharmaceutical formulation thereof) in an amount ranging from 1 mg/day to 50 mg/day. In yet additional embodiments, the dosage can be a prophylactic dosage, which can include administering a compound (or pharmaceutical formulation thereof) in an amount ranging from 0.1 mg/day to 30 mg/day.

Compositions comprising one or more of the compound embodiments disclosed herein typically comprise from greater than 0 up to 99% of the compound by total weight percent. More typically, compositions comprising one or more of the compound embodiments disclosed herein comprise from 1 to 20 total weight percent of the compound, and from 80 to 99 weight percent of at least one pharmaceutically-acceptable component.

In some embodiments, CCSxSOD mouse data can reflect human ALS patient responses, because the balance of CCS to SOD is closer to humans than other SOD mouse models of ALS. In an exemplary embodiment, a dosage of approximately 10 mg/kg/day is used to treat mice. In this embodiment, the dosage is split into two treatments per day. To scale this dosage to humans, two factors are taken into account. The first is the factor of 12 recommended by the FDA for allometric scaling from mice to humans. The second is that the mutant SOD gene has approximately 30 copies compared to human ALS patents. Thus, the average dose is calculated as 5/360=0.014 mg/kg per dose (or approximately 1 mg) of the compound for a 70 kg adult human. Copper is about $\frac{1}{6}^{th}$ the weight of compounds described herein. Thus, two doses at 1 mg per day can provide approximately 0.3 mg of copper per day.

V. Methods of Making Compounds

Disclosed herein are embodiments of a method for making the compound embodiments described herein. In particular disclosed embodiments, the method can comprise using any one or more of the method embodiments described below. The methods can comprise making a ligand component and exposing the ligand component to a metal precursor composition to form a complex between the ligand and a metal provided by the metal precursor. A person of ordinary skill in the art with the benefit of the present disclosure will recognize that the methods described herein can be adapted to prepare compound embodiments contemplated herein that may not be expressly included in the schemes below. Compound embodiments described herein remain dissolved in refluxing solvents, which facilitates a one-pot synthesis including the addition of the complexing metal. In particular disclosed embodiments, yields of the methods described herein can be as high as 99%.

In some embodiments, a ligand component of the compound embodiments described herein can be made using a method as illustrated in Scheme 1. With reference to Scheme 1, a ligand precursor compound 100 (or a combination of ligand precursor compounds 100 and 100', such as where $R^3$ and $R^4$ are different groups) can be exposed to a diketone reactant 102 to form a diimine product 104. Suitable solvents include any organic solvent typically used in organic synthesis and temperatures above ambient temperature (such as reflux temperatures) can be used.

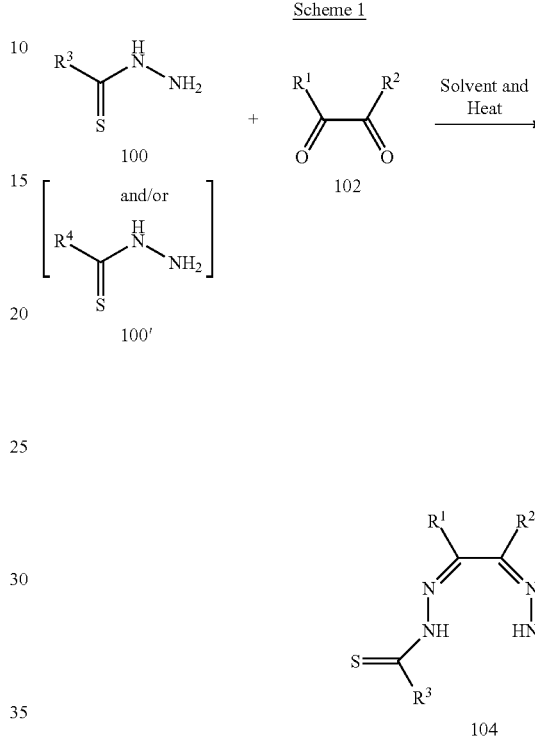

The method of Scheme 1 can be modified to make other analogs of the diimine product 104 by preparing diketone analogs of formula 204, such as by using a method as illustrated in Scheme 2. Any suitable solvent can be used and the catalyst can be selected from a metal-containing catalyst, such as a cobalt-containing catalyst (e.g., $CoCl_2$). A benzaldehyde compound 200 can be used to make the diketone compound 204; benzaldehyde analogs are commercially available (e.g., 4-(trifluoromethyl)benzaldehyde is available from Sigma Aldrich) and/or can be readily synthesized using methods known to those of ordinary skill in the art with the benefit of this disclosure. As illustrated in Scheme 3, the diketone analog compounds having formula 204 can be reacted with ligand precursor compound 100 (or a combination of ligand precursor compounds 100 and 100').

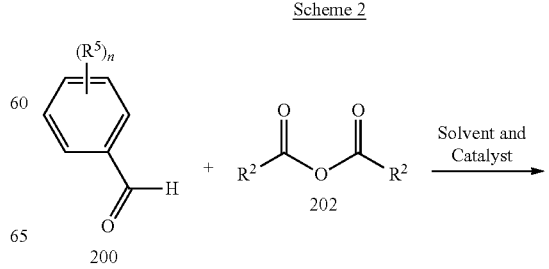

107
-continued

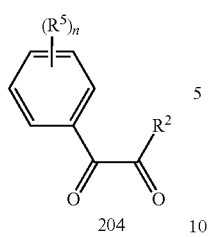
204

Scheme 3

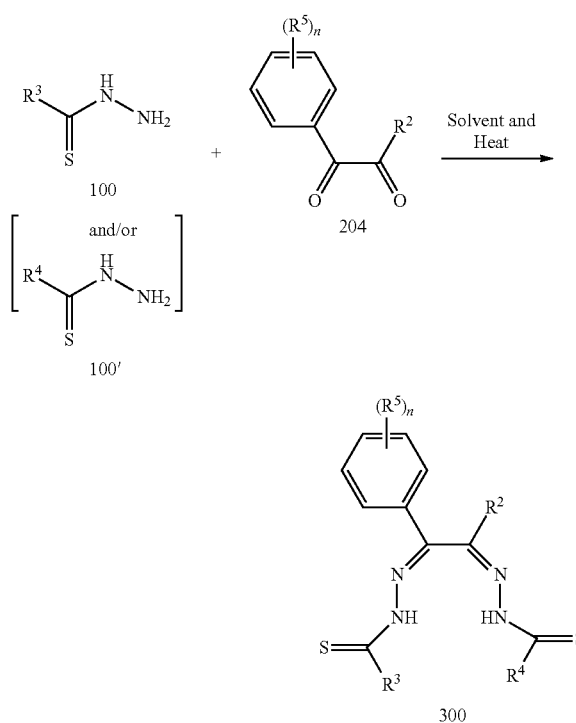

An exemplary method for making a particular species of the ligand component is illustrated in Scheme 4. Other analogs can be made by modifying the method of Scheme 4 to utilize analog compounds obtained using the methods of Schemes 2 and 3.

Scheme 4

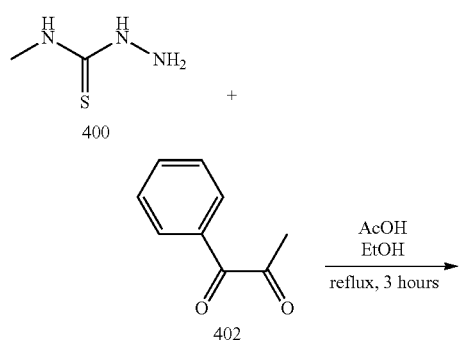

108
-continued

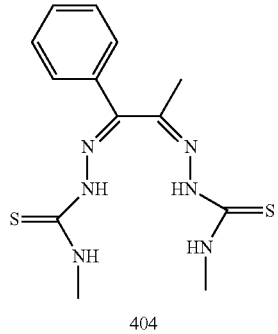
404

Diimine compounds having formula 300 (and/or diimine compound 104) made using the methods described above can be combined with a metal to provide the compound embodiments disclosed herein. In some embodiments, the diimine compounds can be exposed to a metal precursor composition. The metal component of the metal precursor will form a complex with the ligand component to provide compound 500 as illustrated in Scheme 5.

Scheme 5

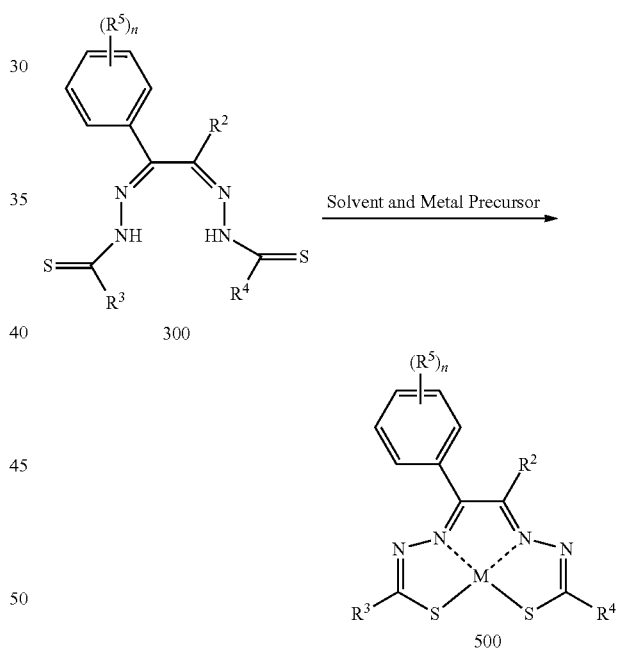
500

In additional embodiments, method embodiments for making compounds comprising a linker-X group can be used. Suitable methods for making such compounds are illustrated below in Schemes 6 and 7. A person of ordinary skill in the art with the benefit of this disclosure would recognize that the methods can be modified so that $R^3$ also can be a linker-X group and such modifications can be carried out using substitution reactions and/or functional group modifications recognized by those of ordinary skill in the art with the aid of the present disclosure. The precursor compounds 600 used to form ligand components comprising linker-X groups can be made using methods illustrated in Scheme 8.

Scheme 6
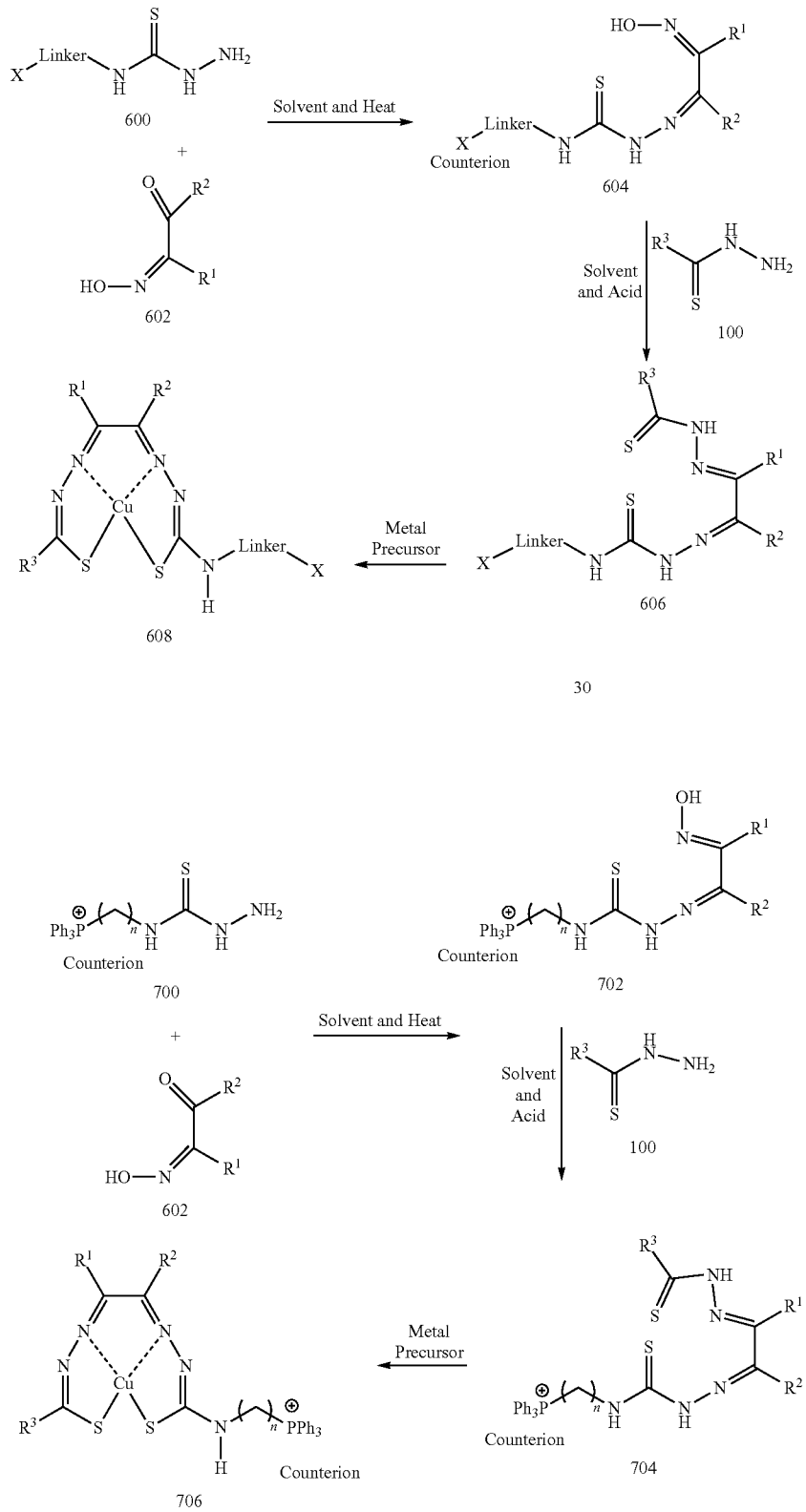

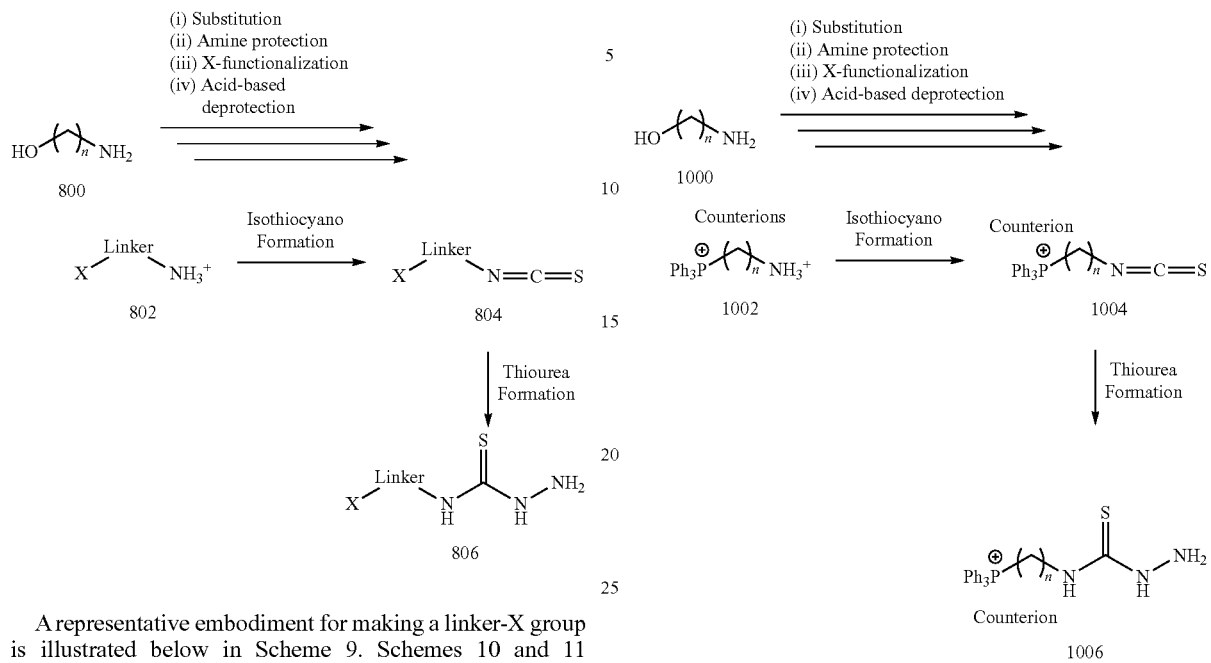
A representative embodiment for making a linker-X group is illustrated below in Scheme 9. Schemes 10 and 11 illustrate representative methods for coupling the linker-X group with a precursor and methods for forming ligand components comprising linker-X groups.
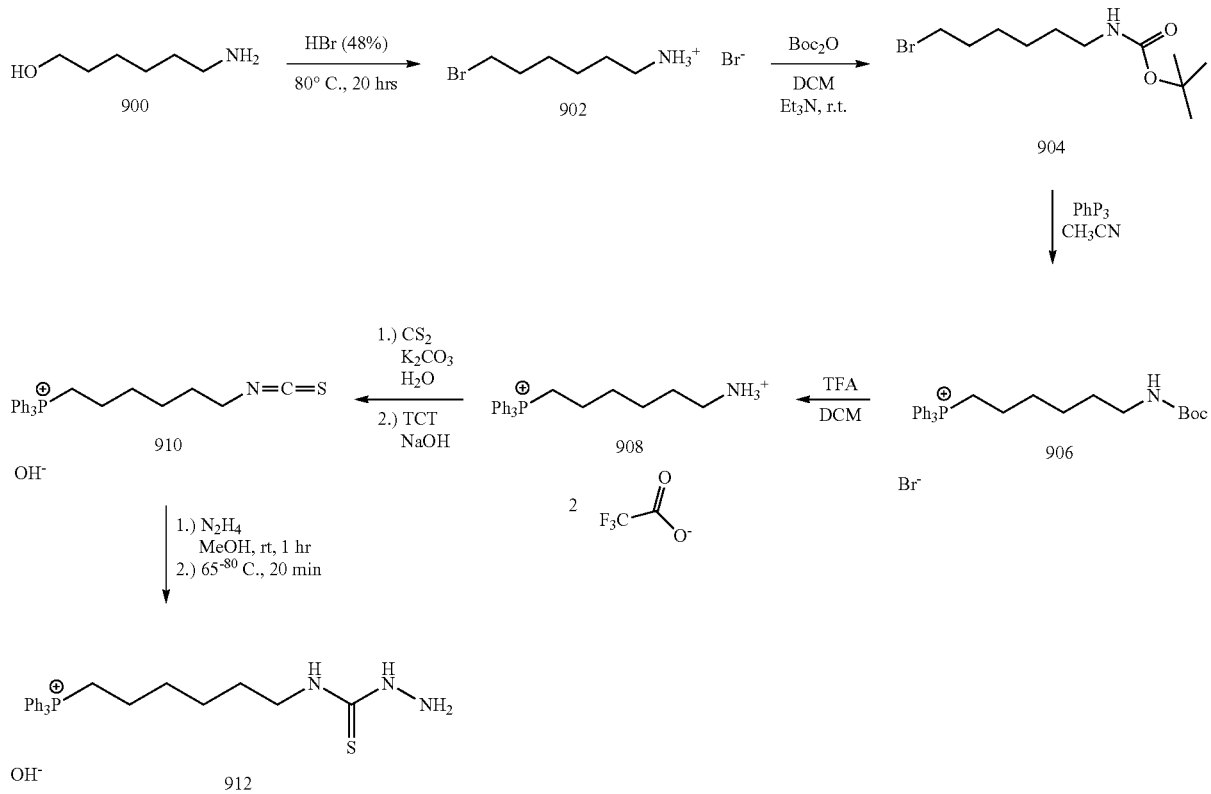

Scheme 11

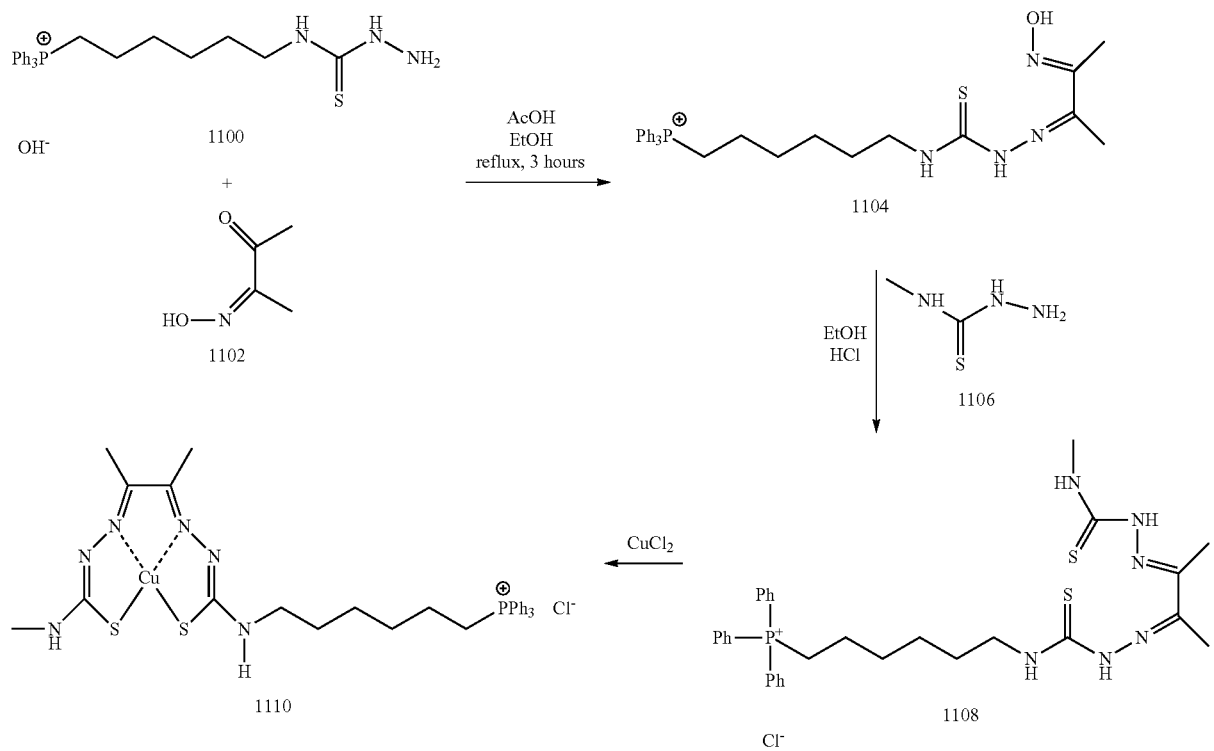

In some embodiments, the method described herein can be used to form a 1:1 complex between a metal and a corresponding ligand component. As such, the method embodiments described herein are particularly well-suited for large-scale synthesis. As such, the method can be used to make gram-scale, even kilogram-scale, amounts of the compound embodiments described herein. The method avoids forming higher order complexes (e.g., compounds comprising 2 or three metal atoms complexed to one or more ligand components) and thus avoids complex separation techniques needed to separate reaction products.

VI. Examples

General Method for Mass Spectrometric Assay

Tissue Preparation for SOD and Cytochrome c Oxidase assays—Whole brains and spinal cords were rapidly dissected from euthanized transgenic mice, immediately frozen in liquid nitrogen, and then stored at −80° C. until use. To prepare brain tissue for mass spectrometry or cytochrome c oxidase assay, frozen brains were first placed on a plate on top of a slab of dry ice so that the brittle frozen tissue could warm to a temperature that allowed sectioning with a razor blade (approx. −10° C.). Motor cortex and surrounding cerebrum was then sectioned to a thickness of approximately 1 mm with a razor blade. A 500 μm biopsy needle was used to isolate three ~250 μg punches from each mouse tissue, which provided technical replicates for mass spectrometry and cytochrome c oxidase examples. Tissue punches were weighed using a Cahn 25 Automatic Electrobalance (Cerritos, CA, USA) with a sensitivity of ±0.1 μg. Tissue punches were homogenized for 12 seconds using a VWR Handheld cordless motorized homogenizer to a concentration of 5 μg tissue/μl of homogenization buffer. Homogenization buffer (made fresh daily) was 10 mM ammonium acetate, pH 5.0-5.1. For SOD measurements, 300 nM bovine SOD (Sigma) was added as an internal standard. The ratio of human SOD to the bovine SOD internal standard was used to calculate the concentration of human SOD detected in mouse tissue. After homogenizing, samples were centrifuged for 2 minutes at 16000×g at 4° C. in an Eppendorf 5415 R centrifuge to pellet cell debris. Supernatant was transferred to a clean tube for mass spectrometry or cytochrome c oxidase assays. Repeatability with downstream assays was attained by homogenizing in a volume between 100 μl for each tissue punch in a 1.7 ml plastic centrifuge tube.

Mass Spectrometry—A pipette tip, such as a C4 ZipTip® (Millipore, Billerica, MA, USA) was used to bind and desalt human SOD from the mouse brain supernatant. The ZipTip® preparation consisted of wetting first with three volumes of 10 μl of acetonitrile followed by three rinses with 10 μl of water. Samples were bound to the wetted ZipTip® matrix by drawing 10 μl of sample supernatant across the ZipTip® matrix ten times, followed by rinsing with 10 μl of water eight times.

An LTQ-FT Ultra hybrid linear ion trap-Fourier transform ion cyclotron resonance mass spectrometer (Thermo, San Jose, Calif.) with a Finnigan Ion Max API source configured for electrospray ionization (ESI) in positive ion mode was used for all mass spectrometry experiments. All SOD quantitation was performed using the linear ion trap with scan range of 800 to 2000 m/z, which allowed for detection of SOD multiple charge states +9 through +13. The solvent used for mass spectrometry was 30:70 acetonitrile:water with 100 μM formic acid. Solvent was run through the prepared ZipTip®, through a 0.22 micron filter and directly into the electrospray needle.

To assay presence of the C57-146 disulfide bridge normally found in mature SOD, S-methyl methanethiosulfonate (MMTS) was added to homogenates before performing mass spectrometry. MMTS reacts with free sulfhydryls to form one mass-spectrometry-detectable methyl-disulfide on each accessible sulfhydryl. SOD-WT (wild-type) has four cysteine residues: Cys 6, pointing toward the inside of the beta barrel of SOD, is normally inaccessible to solvent; C57 and C146 form the intra-monomer disulfide bridge in mature SOD, and so will not react if the bridge is formed; and C111 is normally available to react. Therefore, the extra mass of one $SCH_3$ group indicated that the C57-146 disulfide bridge was present, while three $SCH_3$ masses indicated that the disulfide bridge was reduced.

Data were quantified in a custom Matlab program. Human SOD apo, 1 mtl, and 2 mtl peak intensities were summed over all charge states and converted to concentrations using bovine SOD as an internal standard. Mature SOD is defined as the superoxide dismutase protein containing both copper and zinc plus having the intramolecular disulfide bond oxidized. Immature SOD is defined as superoxide dismutase protein missing either or both copper and zinc, or having the intramolecular disulfide bond reduced.

Cytochrome c oxidase assay—The assay buffer included 30 uM reduced cytochrome c in 50 mM potassium phosphate buffer pH 7.0 containing 20 µM EDTA and 24 units/ml catalase. The final dilution of reduced cytochrome c stock should yield an absorbance at 550 nm of 0.7. To initiate the assay, 2 µl of CNS tissue homogenate was added to 1 ml of assay buffer at 25 C and the reduction of cytochrome c was followed by the decrease at 550 nm over time. To minimize interference from turbidity, the absorbance at 550 nm minus the absorbance at 580 nm was monitored. The change in absorbance was measured for one minute. Then, 2 µl of 100 mM sodium cyanide and the absorbance change was monitored for another 20 seconds. Cyanide inhibits cytochrome c oxidase activity and completely inhibits cytochrome c reduction. Enzyme activity was expressed in units per mg wet tissue weight, according to the following convention: one unit will oxidize 1.0 µmole of ferrocytochrome c per minute @ 25 C, pH 7.0. The values reported here match literature values.

Example 1

Figure 5:
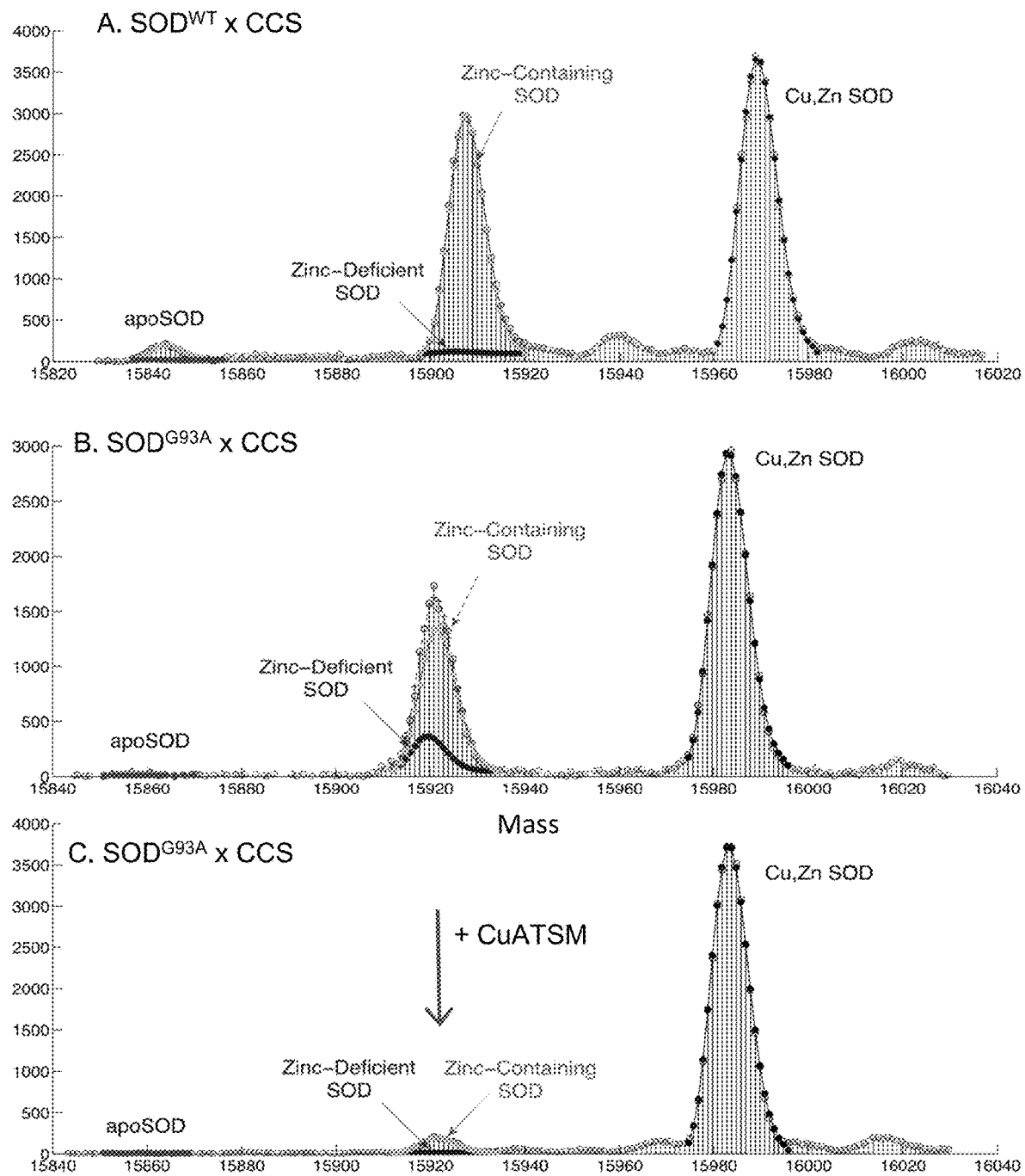
FIG. 5 is a combined mass spectrum showing mass spectra of $SOD^{WT}$ (top spectrum) and $SOD^{G93A}$ (middle and bottom spectra) from ventral spinal cord samples, before and after exposing the samples to CuATSM (top and middle spectra versus bottom spectrum).

The above described high-resolution mass spectrometric method can be used to quantify copper and zinc binding to the SOD protein directly in ventral spinal cord of ALS-affected tissues. These assays reveal that in the spinal cord of mutant SOD mice nearly half of the SOD protein was Cu,Zn SOD, while the other half of SOD protein predominately contained zinc but not copper and that effective copper delivery also may require coexpression of CCS (see FIG. 5). Without wishing to be bound to a particular theory, it currently is believed that these results suggest that copper loading into SOD in the CNS of $SOD^{G93A}$ mice reached a rate-limiting process that was too slow to keep up with SOD synthesis, potentially due to the limited amount of endogenous mouse CCS relative to human SOD protein. In particular disclosed embodiments, this assay can be used to corroborate that compound embodiments disclosed herein are able to serve as effective therapeutics in neurological disorder treatment.

In some embodiments, $CCS \times SOD^{wt}$ mice can provide a rapid assay to determine how well compound embodiments described herein can replenish cytochrome c oxidase and SOD in the CNS. In some embodiments, mice pups start treatment at 4 days and are followed for 6-21 days before sacrifice and the two enzymes are assayed in CNS tissues. Copper incorporation is followed in SOD by mass spectrometry using the mass spectrometry assay discussed above.

Example 2

Figure 4:
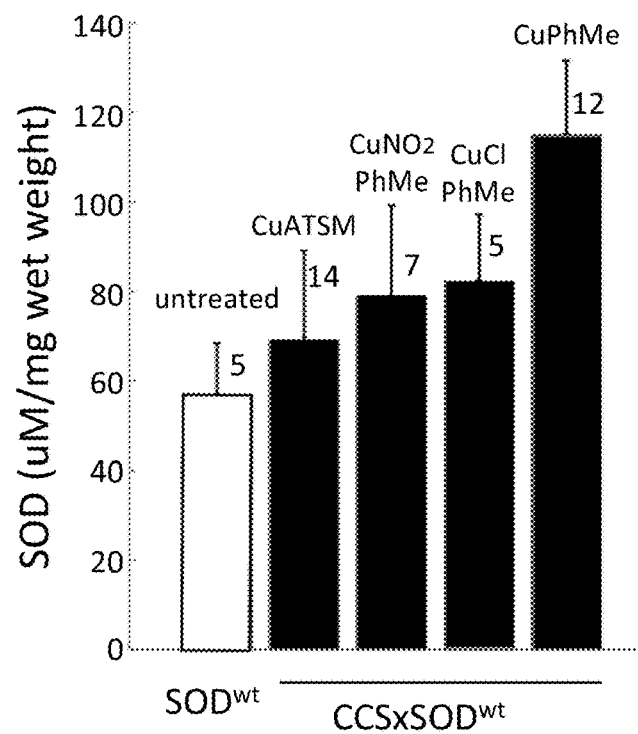
FIG. 4 is a graph showing results obtained from exposing mice to CuATSM and different compound embodiments described herein, confirming that disclosed compound embodiments effectively increase mature Cu,Zn SOD formation; sample sizes for the number of mice in each group are shown by the numbers provide above each bar in the graph.
Figure 6:
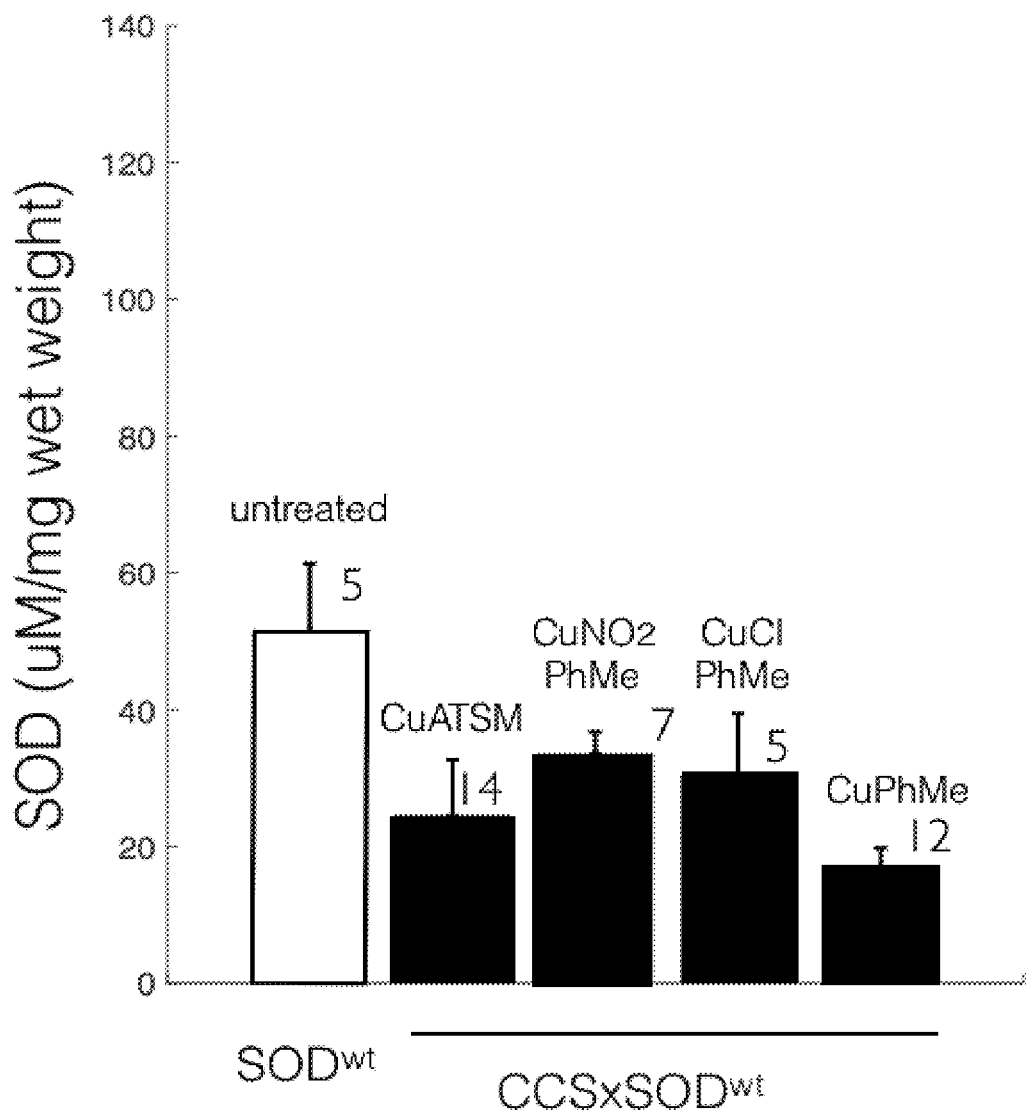
FIG. 6 is a graph showing results obtained from exposing mice to CuATSM and different compound embodiments described herein, confirming that disclosed compound embodiments effectively in decrease the amount of immature forms of SOD; sample sizes for the number of mice in each group are shown by the numbers provide above each bar in the graph.

This example establishes that the compound embodiments disclosed herein are able to deliver copper to enable the maturation of copper-deficient SOD more efficiently in $CSS \times SOD^{WT}$ transgenic mice than CuATSM (FIGS. 4 and 6). In this example, CuATSM only increased mature SOD by 13 uM compared to untreated $SOD^{WT}$ mice, whereas particular compound embodiments described herein were able to exhibit higher increases, with CuPhMeTSM increasing SOD by 60 uM. The amount of immature SOD was also decreased most by CuPhMeTSM. Without being bound by a particular theory, it is currently believed that the immature SOD is most likely to be involved in generating the toxic form of SOD responsible for the death of motor neurons in vivo.

Example 3

Figure 7A:
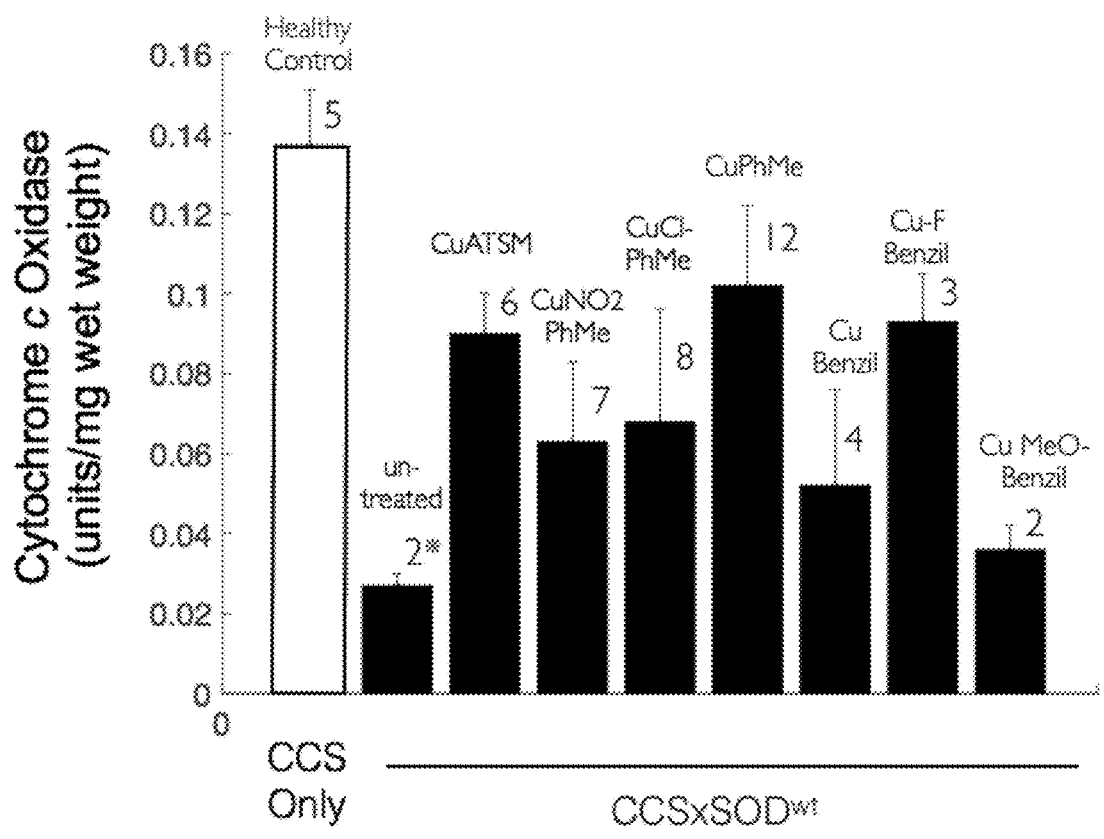
FIGS. 7A and 7B are graphs showing results obtained from exposing mice to CuATSM and different compound embodiments described herein, confirming that the disclosed compound embodiments effectively increase COX activity in brain (FIG. 7A) and spinal cord (FIG. 7B); sample sizes for the number of mice in each group are shown by the numbers provide above each bar in the graph.
Figure 7B:
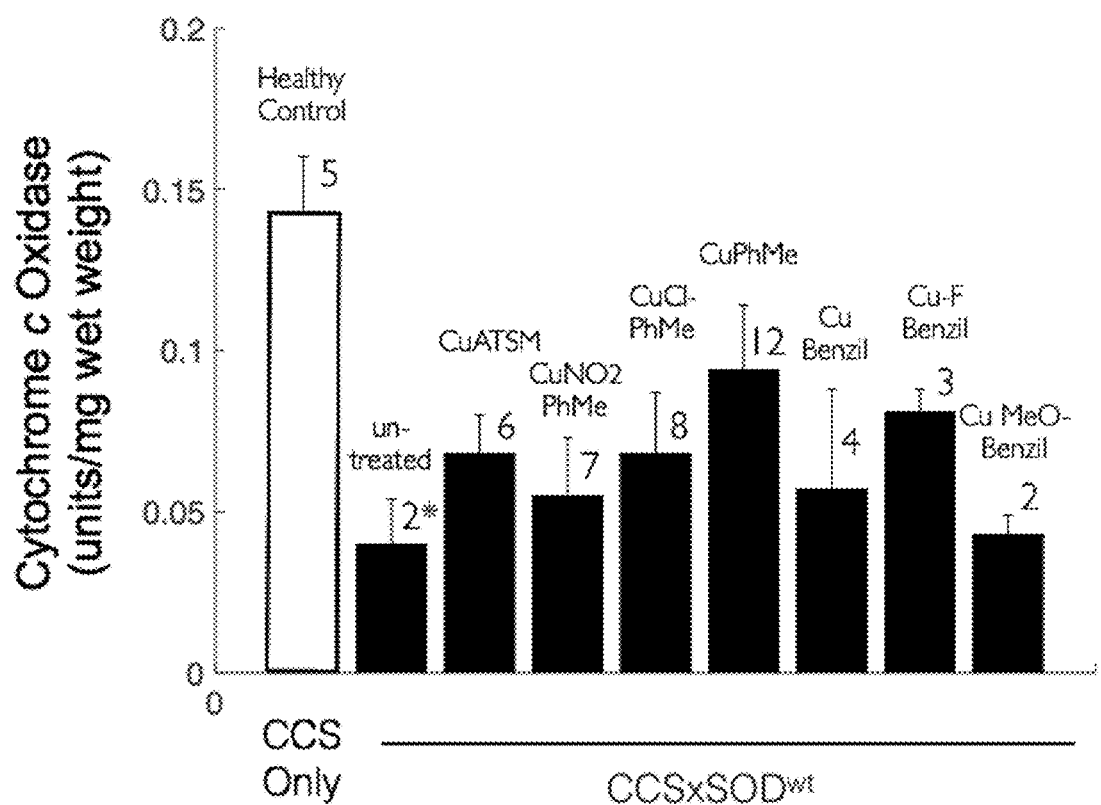

This example illustrates that compound embodiments disclosed herein also exhibit superior activity over CuATSM in terms of increasing COX activity in the brain (FIG. 7A) and spinal cord (FIG. 7B). In this example, an increase in COX activity to nearly twice the extent of CuATSM (FIGS. 7A and 7B) was observed for the CuPhMeTSM compound. The compound was administered dermally with DMSO in an amount of 50 mg/kg/day once daily starting at four days-of-age and measurements were taken at day 21. While the nitro analog was not as effective as the CuPhMeTSM embodiment in this particular example, other analogs exhibited increases, such as halogenated analogs. FIGS. 7A and 7B illustrates results from this example, which evaluated the efficacy of compound embodiments disclosed herein in increasing COX activity. Samples sizes for the number of mice in each group are shown by the numbers. The dashed line shows the level of COX activity of untreated mice. The COX activity of untreated SOD×CCS mice was consistently 0.04 units/mg at all ages and two mice survived to 21 days. With reference to FIGS. 6A and 6B, CuPhMe=copper phenylmethylTSM; $CuNO_2PhMe$=copper 4-nitrophenylmethylTSM; CuCl-PhMe=copper 4-chlorophenylmethylTSM; CuBenzil=copper diphenylTSM; Cu-MeO Benzil=copper di-4-methoxyphenylTSM.

Example 4

Figure 10:
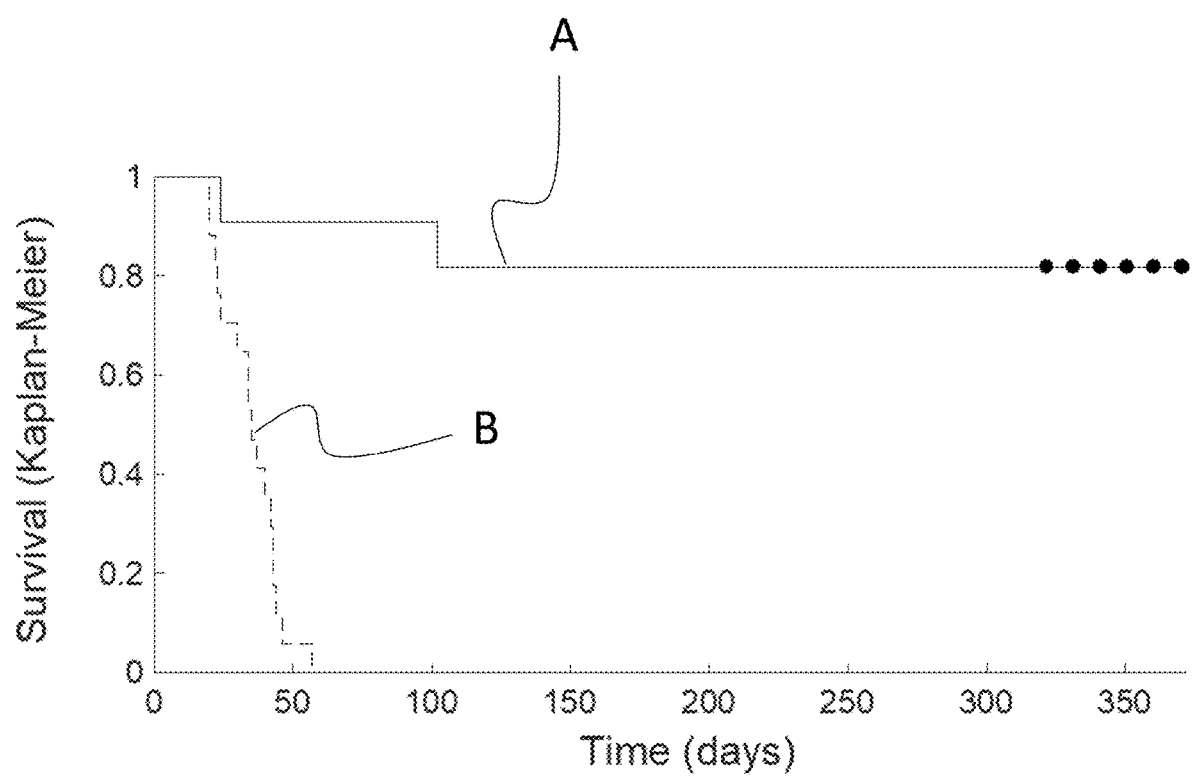
FIG. 10 is a graph illustrating the survival rates of low expressing G93A SOD mice crossed to CCS overexpressing mice after treating the mice with CuPhMeTSM (50 mg/kg/day) after four days of age; the graph illustrates that a majority of the mice (specifically, nine out of 11 mice) were still alive after receiving treatment with the CuPhMeTSM (line labeled "A"), whereas untreated mice (line labeled "B") exhibited much lower survival rates (confidence levels are shown as dashed lines, with lines "C" and "D" corresponding to the treated mice and lines "E" and "F" corresponding to the untreated mice).

In this example, G93A SOD×CCS mice were treated with 50 mg/kg/day of CuPhMeTSM transdermally starting at 4 days of age. The compound was able to keep six G93A SOD×CCS mice alive for 300 days (n=6). Results are illustrated in FIG. 10. There has been no toxicity apparent to date from the treatment.

Example 5

Figure 2:
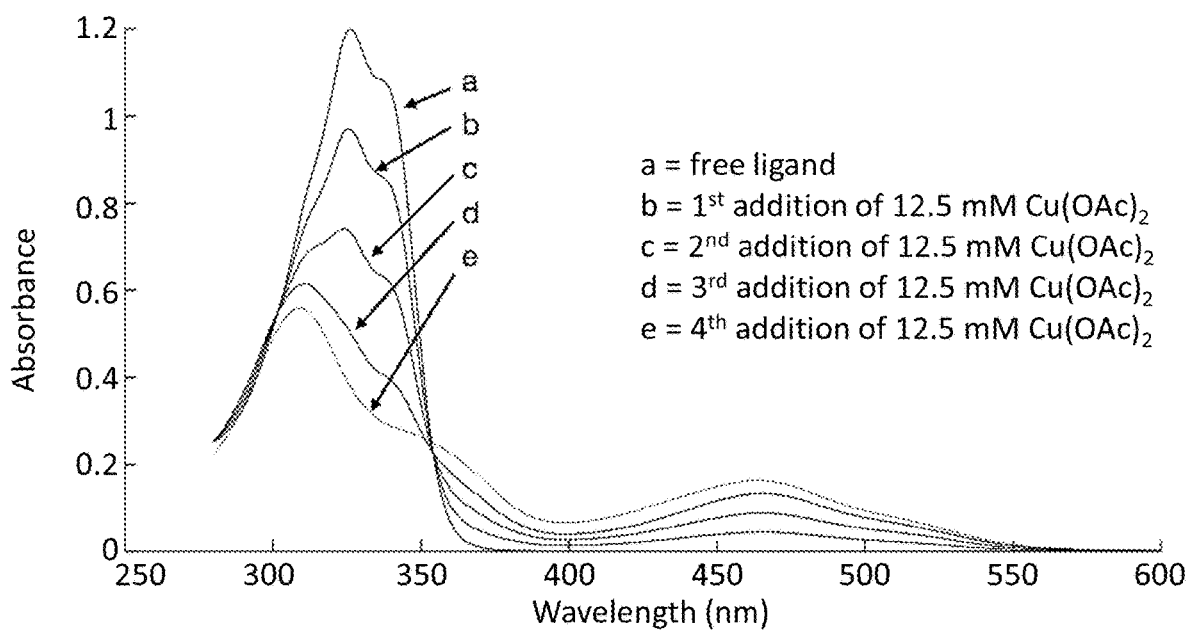
FIG. 2 illustrates titration curves obtained from a titration wherein copper is added to the free ATSM ligand component.
Figure 8:
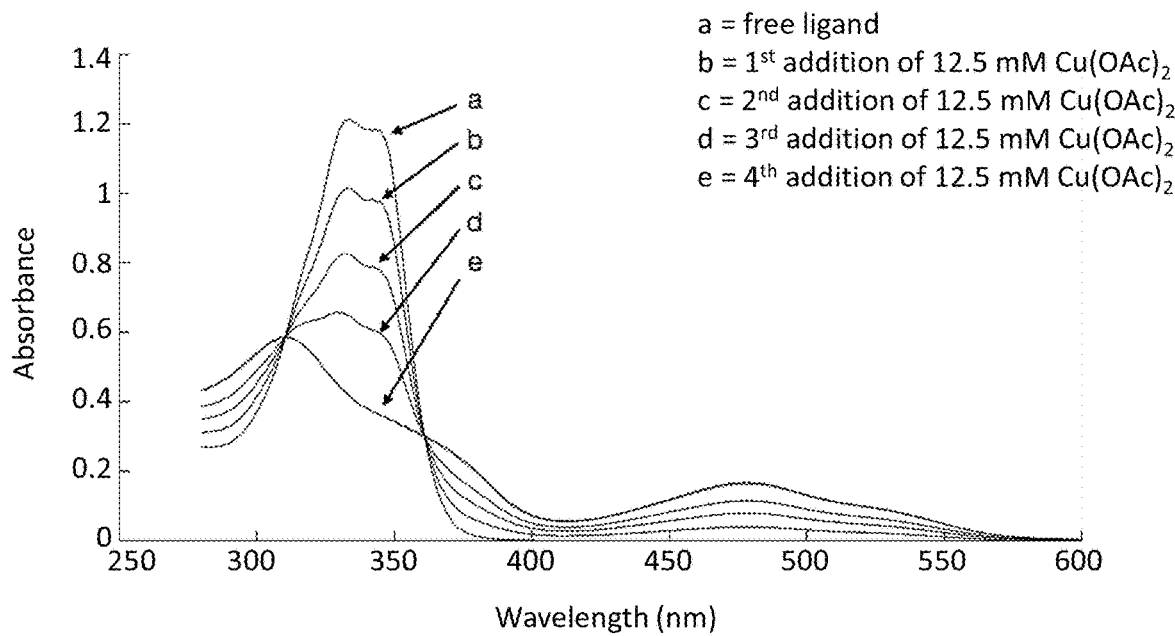
FIG. 8 illustrates titration curves obtained from a titration wherein copper is added to the free PhMeTSM ligand component.
Figure 9:
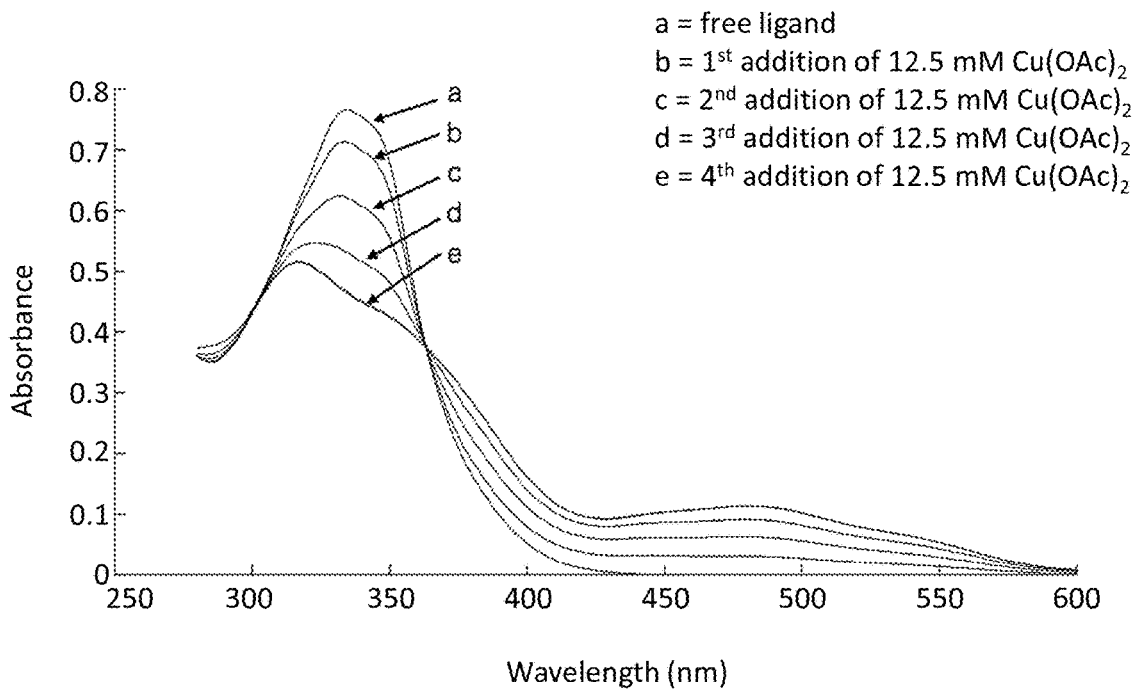
FIG. 9 illustrates titration curves obtained from a titration wherein copper is added to the free $NO_2$PhMeTSM ligand component.

In this example, titration curves obtained from copper additions to ligand embodiments described herein are compared. FIG. 2 shows a titration with copper being added to the ligand ATSM. However, as copper additions approach 1:1, the isosbestic points deviate, showing the formation of unwanted nonstoichiometric behavior. The PhMeTSM ligand yields clean isosbestic points and forms a 1:1 complex and the $NO_2PhMeTSM$ ligand also exhibits similar reactivity. For example, compare FIG. 2 (which shows copper titration curves of the ATSM ligand) with FIGS. 8 and 9 (which show copper titration curves of the PhMeTSM and $NO_2PhMeTSM$ ligand). As can be seen in FIG. 2, with successive additions of copper (each addition was 25% of the ATSM ligand concentration), the absorbance increased with a distinct isosbestic point at 354 nm apparent; however, as the copper concentration approached 1:1, the isosbestic behavior was lost due to the formation of a third type of complex involving several copper atoms and at least two ATSM ligands. In contrast, with successive additions of copper (each addition was 25% of the ligand concentration), the absorbance increased with distinct isosbestic points at 311 and 362 nm for PhMeATSM and 302 and 363 nm for $NO_2$-PhMeATSM (FIGS. 8 and 9). At a copper concentration of 1:1 with both the PhMeATSM and the $NO_2$-PhMeATSM, the isosbestic behavior was preserved unlike ATSM. These data confirm that CuPhMeTSM and other analogs described herein exhibit chemical stability suitable for large scale syntheses, thus lending to its utility and applicability in industry and the pharmaceutical field.

Figure 3:
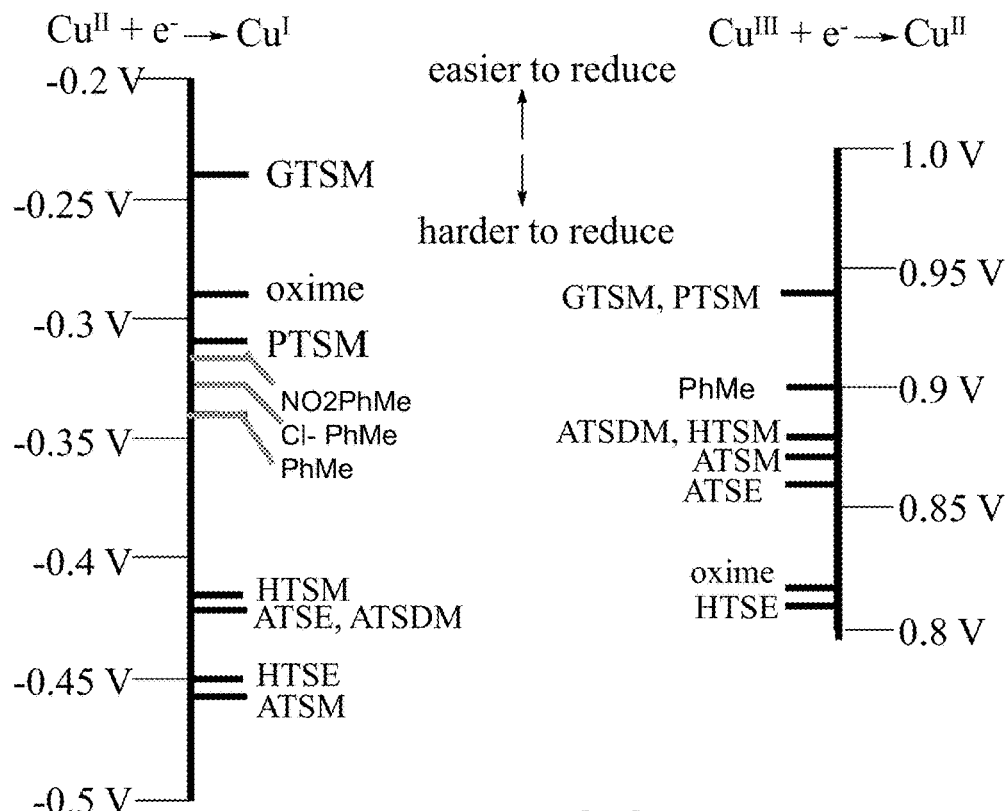
FIG. 3 illustrates reduction standard potentials (left side) versus oxidation standard potentials (right side) for ligand components.
Figure 11:
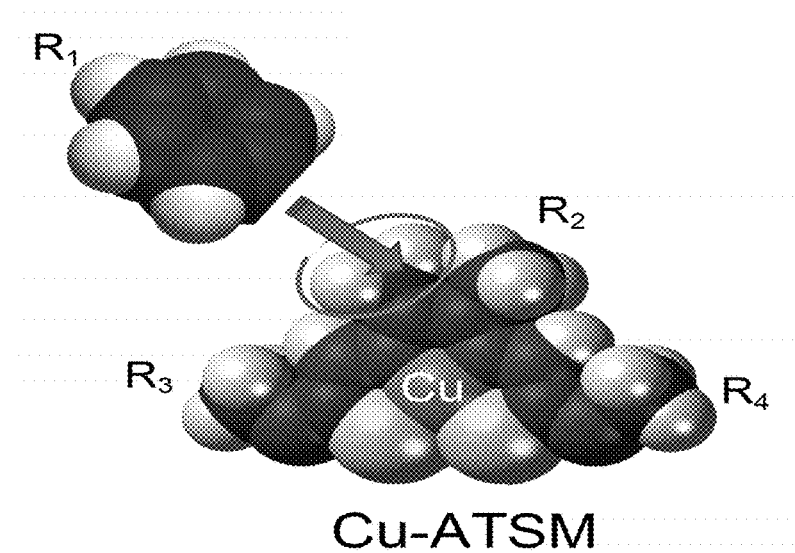
FIG. 11 illustrates a space-filling model of a compound embodiment described herein.

CuPhMeTSM and other compound embodiments described herein have reduction potential intermediates that makes copper release via reduction more easily achieved with physiologically plausible reductants, as illustrated in FIG. 3. The steric strain (see FIG. 11) created by the phenyl group of particular compound embodiments described herein can stabilize $Cu^{1+}$ to make the reduction potential more positive. The oxidation wave of CuATSM shows that oxidized approximately by 40 mV more easily than CuPhMeTSM.

Example 6

Synthesis of CuPhMeTSM—In a 50 ml round bottom flask, 20 ml of anhydrous ethanol was heated to 75° C. with an oil bath and continuous stirring. 15 mmol of solid 4-methylsemithiocarbazide was dissolved completely, followed by 7.5 mmol of 1,2-phenylpropane dione (1 ml). Five drops of concentrated sulfuric acid were added to initiate the reaction and it was allowed to stir for an additional 30 minutes. The reaction was cooled to room temperature and then refrigerated overnight. The filtrate was cooled and washed with cold water and dried under high vacuum. The PhMeTSM ligand was isolated in >70% yield.

The ligand was redissolved in hot methanol and treated with 1:1 molar ratio of copper chloride dissolved in methanol. The CuPhMeTSM forms a solid red precipitate that was washed with cold water to remove excess copper and then dried under vacuum.

Example 7

6-bromohexylammonium bromide

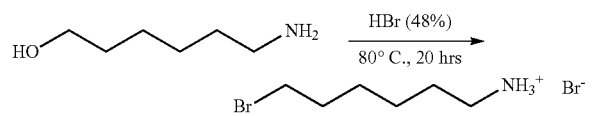

To a solution of 48% HBr (5.10 mL) at 0° C. was added 6-aminohexanol (0.5090 g, 4.27 mmol) slowly in portions. Once the 6-aminohexanol dissolved the reaction was warmed to room temperature, fitted with a reflux condenser, and heated to 80° C. The consumption of the starting alcohol was monitored by TLC (1:1 EtOAc:MeOH) using a ninhydrin stain. The reaction was complete after 20 hours and the solution was concentrated in vacuo yielding a tan solid. This was recrystallized from toluene/ethanol (50:1) to afford a white solid.

Data: $R_f$ 0.33 (1:1 EtOAc:MeOH) $^1$HNMR (400 MHz, $D_2O$) δ 3.46-3.41 (2H, t, J=7), 2.96-2.89 (2H, t, J=8), 1.84-1.75 (2H, m), 1.64-1.55 (2H, m), 1.43-1.30 (4H, m).

6-(Boc-amino)hexyl bromide

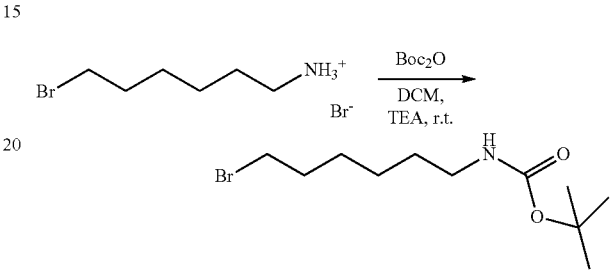

6-bromohexylammonium bromide (0.100 g, 0.383 mmol) was dissolved in 5.00 mL of anhydrous DCM. Triethylamine (0.11 mL, 0.804 mmol) was added dropwise to the stirring solution followed by Boc anhydride (0.092 g, 1.10 mmol). The reaction was stirred at room temperature and monitored by TLC using a ninhydrin stain. After 20 hours it was determined that all of the starting amine was consumed. The reaction was concentrated in vacuo to afford a white solid. This was dissolved in $H_2O$ and extracted 3× with 10.00 mL EtOAC. The organic layer was dried over $Na_2SO_4$, filtered, and concentrated in vacuo to afford a brown oil as the desired product.

Data: $R_f$=0.57 (1:1 EtOAc:MeOH) Ninhydrin stain. $^1$HNMR (400 MHz, DMSO) δ 7.94-7.86 (3H, m) 7.86-7.65 (12H, m), 6.80-6.70 (1H, t), 3.64-3.50 (2H, m), 2.91-2.80 (2H, q), 1.59-1.40 (4H, m), 1.38-1.30 (9H, s), 1.30-1.19 (4H, m).

6-(Boc-amino)hexyltriphenylphosphonium bromide

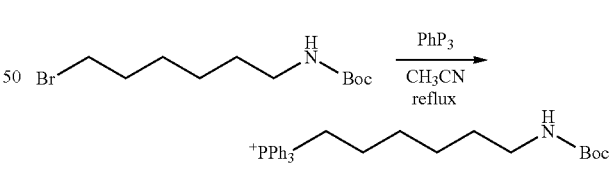

The 6-bromo-boc-hexylamine (1.240 g, 4.42 mmol) was dissolved in 3.00 mL $CH_3CN$. Triphenylphosphine (1.43 g, 5.45 mmol) was added to the stirring solution. A condenser was attached and the stirring reaction was brought to a gentle reflux. The reaction was monitored by TLC using a ninhydrin stain and after 16 hours it was determined that all of the starting amine was consumed. The solution was concentrated in vacuo to afford a crude oil. A column chromatography gradient, EtOAc to EtOAc/MeOH (4:1), afforded the desired product in the second fraction after the elution of unreacted triphenylphosphine.

Data: $R_f$=0.10 (1:1 EtOAc:Hex). ¹HNMR (400 MHz, DMSO) δ 7.90-7.75 (m, 15H), 6.74 (t, 1H, J=5.3), 3.35 (m, 2H), 2.85 (m, 2H), 1.57-1.42 (m, 4H), 1.39-1.33 (s, 9H), 1.33-1.20 (m, 4H).

6-(triphenylphosphonium)-hexylammonium di-trifluoroacetate

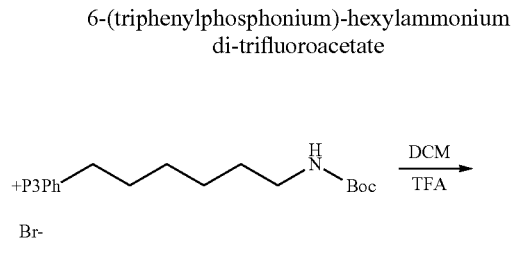

Hartwig, S.; et. Al.; Polym. Chem., 2010, 1, 69-71

The boc-amine was dissolved in 5.00 mL anhydrous dichloromethane and cooled to 0° C. in a 25 mL round bottom flask. Equal volume of trifluoroacetic acid (5.00 mL) was added. The reaction was warmed to room temp and monitored by TLC until complete. The reaction was concentrated to afford the ammonium-trifluoroacetate salt.

Data: $R_f$=0.42 (2:1 EtOAc:MeOH 1% AcOH) ¹HNMR (400 MHz, DMSO) δ 10.132 (brs, 3H), 8.062-7.691 (m, 15H), 3.578 (m, 2H), 2.749 (m, 2H), 1.598-1.437 (m, 6H), 1.332 (m, 2H).

6-(triphenylphosphonium)-isothiocyanate hydroxide

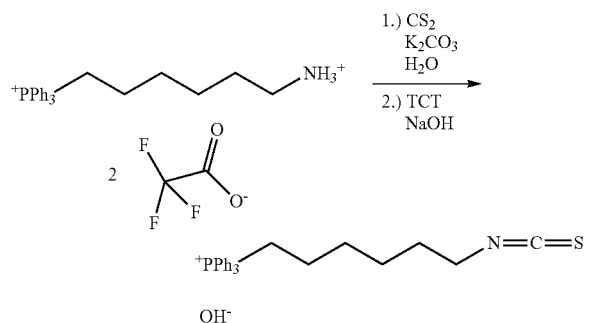

The ammonium-trifluoroacetate salt was dissolved in 5.00 mL of DI H₂O followed by the K₂CO₃ for pH=11. Carbon disulfide was added dropwise and the reaction was stirred at room temp and monitored by TLC. After 3 hours no starting material was observed and the reaction was cooled to 0° C. Trichlorotriazine in 3.00 mL of DCM was added dropwise and the solution was vigorously stirred for 30 min until conversion was observed by TLC. The solution was then treated with 6M NaOH to pH=12. The reaction was transferred to a seperatory funnel and extracted 3x with DCM. The organic layer was dried over Na₂SO₄, filtered, and concentrated in vacuo to afford a viscous yellow oil.

Data: $R_f$=0.75 (2:1 EtOAc:MeOH) ¹HNMR (400 MHz, DMSO) 7.85-7.69 (3H, m), 7.85-7.69 (12H, m), 3.66-3.49 (4H, m), δ 1.70-1.30 (8H, m).

6-[(hydrazinylthioxomethyl)amino]-hexyltriphenylphosphonium hydroxide

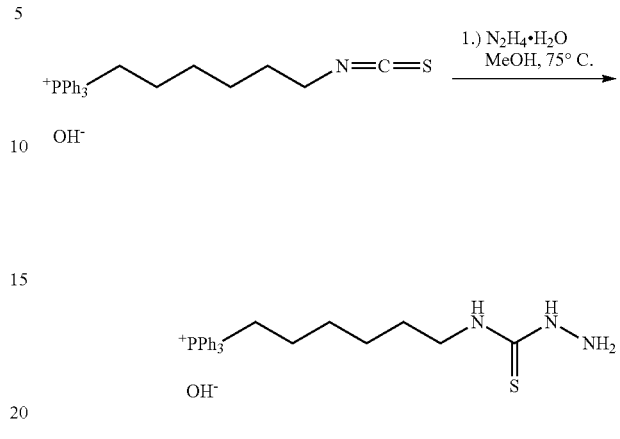

The hydrazine hydrate (1.0 eq.) was added to 10.00 mL of MeOH in a 100 mL round bottom flask and heated to 75° C. The isothiocyanate (0.265 g, 0.628 mmol, 1.0 eq.) was dissolved in 10.00 mL of MeOH and added dropwise over 1 hour. The reaction was stirred for an additional 30 min and then concentrated in vacuo. This was further purified by column chromatography (100% ethyl acetate->20% MeOH/EtOAc) to afford a white solid (0.251 g, 97% yield).

Data: $R_f$=0.30 (1:1 EtOAC: MeOH) ¹HNMR (400 MHz, DMSO) δ 8.59 (1H, s), 7.99-7.65 (15H, m), 4.49 (2H, brs), 3.66-3.55 (2H, m), 3.44-3.45 (2H, m), 3.16 (1H, s), 1.60-1.36 (6H, m), 1.32-1.26 (2H, m).

Mono-Substituted ATSM-Diacetyl

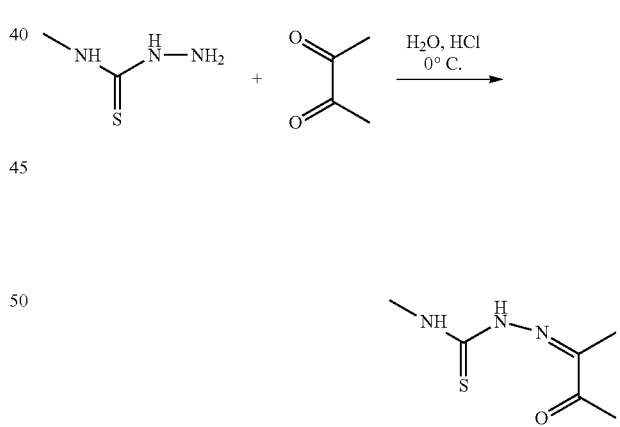

The diacetyl (1.00 mL, 11.38 mmol) was added to 20.00 mL of DI H₂O and acidified with five drops of concentrated HCl. The solution was cooled to 0° C. and then the 4-methylthiosemicarbazide (1.08 g, 10.27 mmol) was added in portions over 1.5 hours. The mixture was then stirred for an additional 30 minutes. The white precipitate that formed was filtered and washed with cold DI H2O, and further dried in vacuo to afford a white solid (1.22 g, 68% yield).

Data: ¹HNMR (400 MHz, DMSO) δ 10.59 (1H, s), 8.65 (1H, m), 3.06 (3H, d, J=4.6), 2.42 (3H, s), 1.97 (3H, s).

Asymmetric TPP-Diacetyl

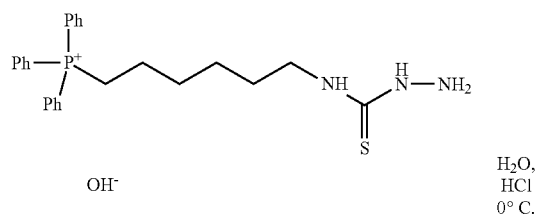

The diacetyl (0.32 mL, 3.60 mmol) was added to 20.00 mL of DI H₂O and acidified with five drops of concentrated HCl. The solution was cooled to 0° C. and then the TPP-hexylthiosemicarbazide (1.49 g, 3.27 mmol) was added in portions over 1.5 hours. The mixture was then stirred for an additional 30 minutes. The white precipitate that formed was filtered and washed with cold DI H2O, and further dried in vacuo.

Data: $^1$HNMR (400 MHz, DMSO) δ 10.58 (1H, s), 8.63-8.59 (1H, t, J=6.0), 7.95-7.68 (15H, m), 3.68-3.51 (4H, m), 2.39 (3H, s), 1.96 (3H, s), 1.57-1.47 (6H, m), 1.38-1.31 (2H, m).

Asymmetric TPP/ATSM

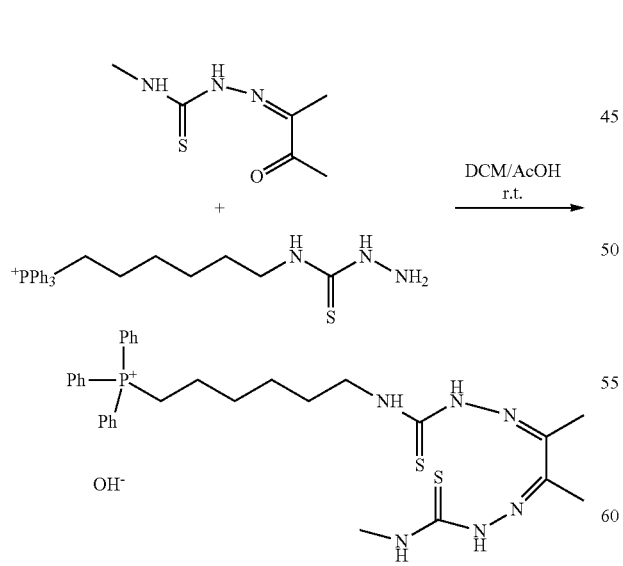

The mono-substituted diacetyl compound (0.7225 g, 4.17 mmol) was added to 50.00 mL anhydrous DCM, followed by the TPP-hexylthiosemicarbazide (0.172 g, 3.79 mmol). Five drops of glacial acetic acid was added to the mixture and the reaction was stirred for 4 hours at room temperature until a yellow precipitate formed. This was filtered, and purified by flash column chromatography. A gradient from 100% EtOAc to 30% MeOH/EtOAc afforded the desired product in the 30% MeOH eluent. Unreacted starting material was obtained in 10% MeOH. The fraction was concentrated in vacuo to afford a yellow solid (2.13 g, 85% yield).

Data: $^1$HNMR (400 MHz, DMSO) δ 10.17 (1H, s), 10.13 (1H, s), 8.43-8.35 (2H, m), 7.94-7.24 (15H, m), 3.63-3.49 (4H, m), 3.04 (3H, d, J=4.6), 2.21 (3H, s), 2.18 (3H, s), 1.60-1.47 (6H, m), 1.37-1.27 (2H, m).

TPP-Containing Copper-Ligand Complexes

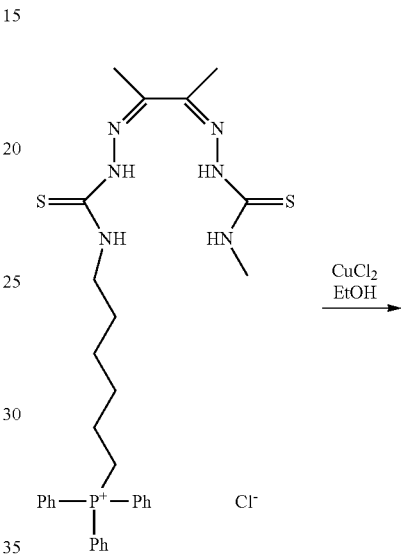

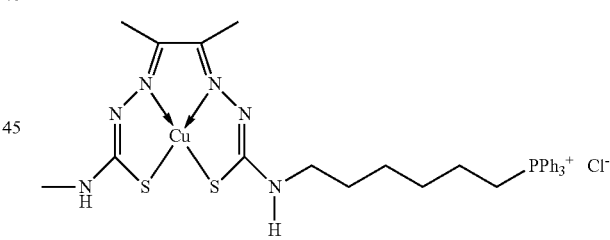

Asymmetric TPP-ATSM

To an oven dried 250 mL round bottom flask was added 4-methyl-3-thiosemicarbazide (1.0 equiv.). 50.00 mL of anhydrous EtOH was added and the mixture was heated to 65° C. while stirring until completely dissolved. The appropriate TPP-compound (1.0 equiv.) was added drop wise to the stirring solution, followed by 5 drops of conc. H₂SO₄. Within 5 minutes, a precipitate forms. This is stirred overnight. The mixture is then filtered and washed with deionized water, MeOH, and EtOH.

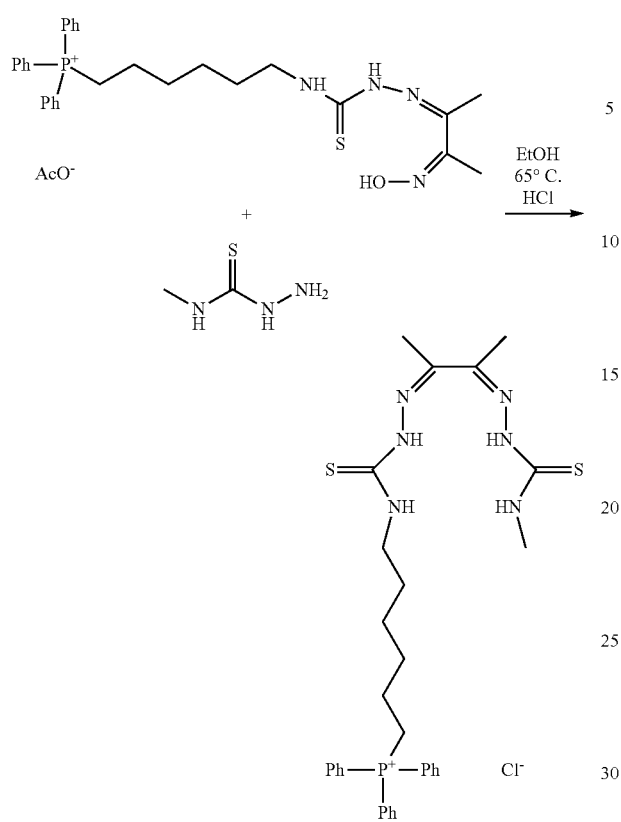

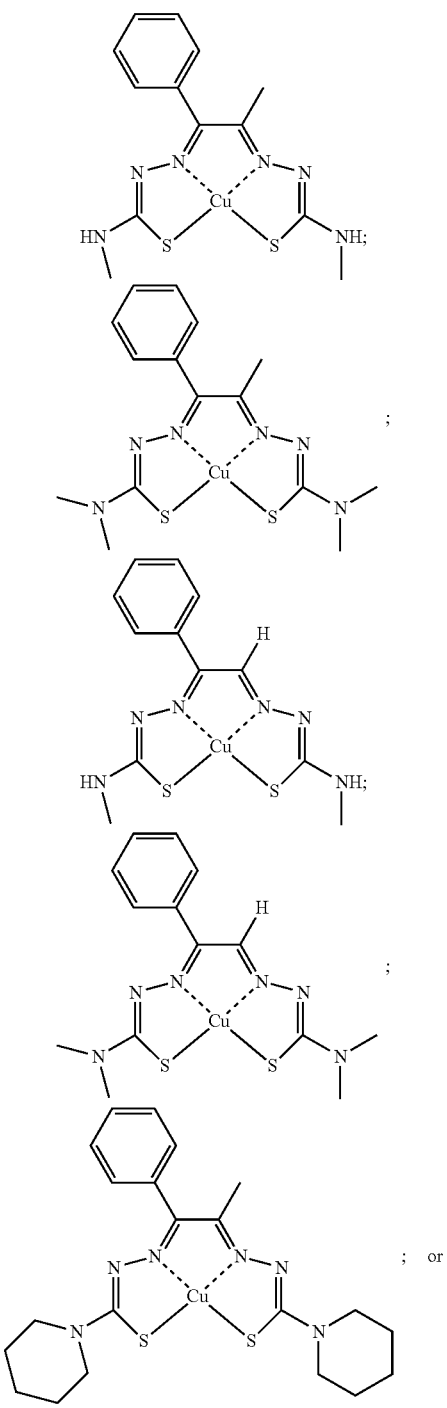

provided that
(i) if $R^1$ is methyl and $R^2$ is methyl or hydrogen, then at least one of $R^2$, $R^3$, or $R^4$ comprises a linker-X group, wherein the linker is selected from a carbonyl-containing group, an alkylene oxide, an aliphatic group, an imidoester; or the linker is generated from a maleimide, a haloacetyl, or a pyridyl disulfide; and wherein X is a moiety that includes functional groups suitable to facilitate delivery of the compound to a target, and wherein the linker-X group is not or is other than $(CH_2)_2N(CH_3)_3$; and
(ii) the compound is not or is other than

VII. Overview of Several Embodiments

Disclosed herein are embodiments of a compound, having a structure satisfying Formula I as described herein and wherein the following variable recitations apply:

M is a divalent metal or a radioactive isotope thereof;

$R^1$ is an aliphatic group or an aromatic group that is attached directly or indirectly through a linker group to $C^a$, wherein the linker group is selected from an aliphatic linker, a heteroaliphatic linker, a heteroatom, an aromatic group, or any combination thereof;

$R^2$ is selected from hydrogen, aliphatic, heteroaliphatic, or an aromatic group that is attached directly or indirectly through a linker group to Cb, wherein the linker group is selected from an aliphatic linker, a heteroaliphatic linker, a heteroatom, an aromatic group, or any combination thereof; or $R^1$ and $R^2$ are bound together form a fused ring system comprising two to seven fused rings;

each of $R^3$ and $R^4$ independently is selected from —$NH_2$, —NHR, —NRR', —OR, —SR, or —$C(R)_{1-2}R'$ wherein R and R' independently are selected from aliphatic, aryl, heteroaliphatic, aliphatic-aryl, heteroaryl, aliphatic-heteroaryl, heteroaliphatic-aryl, or heteroaliphatic-heteroaryl or wherein R and R' are, with the nitrogen or carbon atom to which they are bound, form a heterocyclic or a heteroaryl group, or a cyclic aliphatic group, respectively; or wherein, when $R^3$ and/or $R^4$ are —$C(R)_1R'$, then one of the R or R' groups forms a double bond with the carbon atom and further is joined with the remaining R or R' group to form an aryl group; and

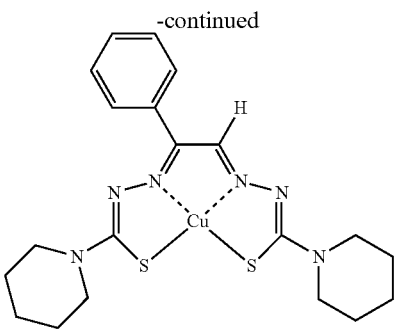

In some embodiments, the compound has a structure satisfying one or more of Formulas IIA-IIR as described herein and wherein, with respect to the appropriate formula, each $R^5$ and $R^6$ independently is selected from aliphatic; aryl; heteroaliphatic; aliphatic-aryl; heteroaryl; aliphatic-heteroaryl; heteroaliphatic-aryl; heteroaliphatic-heteroaryl; hydroxyl; —NH$_2$; nitro; thiol; halogen; phosphate; phosphoryl; sulfino; sulfo; azide; or —O(O)R$^c$X, —C[(R$^c$)$_2$]$_m$X, —[(CH$_2$)$_2$O]$_m$X, —O(CH$_2$)$_m$X, —[O(CH$_2$)$_2$]$_m$X, —NR$^c$(CH$_2$)$_m$X, —SR$^c$X, —CH$_2$C(O)NHR$^c$X, —[(CH$_2$)$_2$NR$^c$]$_m$X, —NR$^c$(CH$_2$)$_2$]$_m$X, —C(=NH$_2^+$)NR$^c$X, or

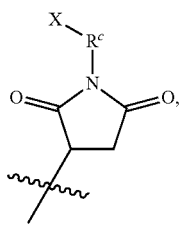

wherein each $R^c$ independently is selected from aliphatic, aryl, heteroaliphatic, aliphatic-aryl, heteroaryl, aliphatic-heteroaryl, heteroaliphatic-aryl, or heteroaliphatic-heteroaryl; each X independently is selected from —P$^+$(R$^d$)$_3$ or —N$^+$(R$^d$)$_3$, wherein each R$^d$ independently can be selected from hydrogen, aliphatic, aryl, heteroaliphatic, aliphatic-aryl, heteroaryl, aliphatic-heteroaryl, heteroaliphatic-aryl, or heteroaliphatic-heteroaryl, and each m independently is an integer selected from 1 to 30; and n is an integer selected from 1 to 5.

In any or all of the above embodiments, the compound has a structure satisfying one or more of Formulas IIIA-IIIY' and wherein, with respect to the appropriate formula, each Y independently is selected from O, S, or NR wherein R is selected from hydrogen, aliphatic, aryl, heteroaliphatic, aliphatic-aryl, heteroaryl, aliphatic-heteroaryl, heteroaliphatic-aryl, heteroaliphatic-heteroaryl, or any combination thereof; each X independently is a targeting moiety; each m is an integer selected from 1 to 30; each q is an integer selected from 0 to 30; and n is an integer selected from 1 to 5.

In any or all of the above embodiments, M is Cu, Co, Ni, or a radioactive isotope thereof, such as Cu$^{2+}$, $^{60}$Cu$^{2+}$, $^{61}$Cu$^{2+}$, $^{62}$Cu$^{2+}$, $^{63}$Cu$^{2+}$, $^{64}$Cu$^{2+}$, or $^{65}$Cu$^{2+}$.

In any or all of the above embodiments, M is Cu$^{2+}$, $^{60}$Cu$^{2+}$, $^{61}$Cu$^{2+}$, $^{62}$Cu$^{2+}$, $^{63}$Cu$^{2+}$, $^{64}$Cu$^{2+}$, or $^{65}$Cu$^{2+}$.

In any or all of the above embodiments, $R^1$ is selected from phenyl, pyridyl, naphthyl, anthracenyl, quinolinyl, quinazolinyl, quinoxalinyl, benzoquinolinyl, benzoquinoxalinyl, benzoquinazolinyl, phenyl-(R$^5$)$_n$, pyridyl-(R$^5$)$_n$, naphthyl-(R$^5$)$_n$, anthracenyl-(R$^5$)$_n$, quinolinyl-(R$^5$)$_n$, quinazolinyl-(R$^5$)$_n$, quinoxalinyl-(R$^5$)$_n$, benzoquinolinyl-(R$^5$)$_n$, benzoquinoxalinyl-(R$^5$)$_n$, or benzoquinazolinyl-(R$^5$)$_n$, wherein each $R^5$ independently is selected from aliphatic; aryl; haloaliphatic; heteroaliphatic; aliphatic-aryl; heteroaryl; aliphatic-heteroaryl; heteroaliphatic-aryl; heteroaliphatic-heteroaryl; hydroxyl; —NH$_2$; —P$^+$(R$^d$)$_3$ or —N$^+$(R$^d$)$_3$ (wherein each R$^d$ independently can be selected from hydrogen, aliphatic, aryl, heteroaliphatic, aliphatic-aryl, heteroaryl, aliphatic-heteroaryl, heteroaliphatic-aryl, or heteroaliphatic-heteroaryl); nitro; thiol; halogen; phosphate; phosphoryl; sulfino; sulfo; azide; a linker-X group; or any combination of such groups; and n is an integer selected from 1 to 10.

In any or all of the above embodiments, n is 1 and $R^5$ is selected from —C(O)R$^c$X, —C[(R$^c$)$_2$]$_m$X, —[(CH$_2$)$_2$O]$_m$X, —O(CH$_2$)$_m$X, —[O(CH$_2$)$_2$]$_m$X, —NR$^c$(CH$_2$)$_m$X, —[(CH$_2$)$_2$NR$^c$]$_m$X, —[NR$^c$(CH$_2$)$_2$]$_m$X, —C(=NH$_2^+$)NR$^c$X, —CH$_2$C(O)NHR$^c$X, —SR$^c$X, or

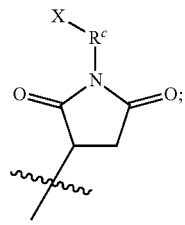

wherein each $R^c$ independently is selected from aliphatic, aryl, heteroaliphatic, aliphatic-aryl, heteroaryl, aliphatic-heteroaryl, heteroaliphatic-aryl, or heteroaliphatic-heteroaryl; each X independently is selected from —P$^+$(R$^d$)$_3$ or —N$^+$(R$^d$)$_3$, wherein each R$^d$ independently is selected from hydrogen, aliphatic, aryl, heteroaliphatic, aliphatic-aryl, heteroaryl, aliphatic-heteroaryl, heteroaliphatic-aryl, or heteroaliphatic-heteroaryl; and each m independently is an integer selected from 1 to 30.

In any or all of the above embodiments, each $R^5$ independently is selected from alkyl, alkyenyl, alkynyl, amine, carboxylic acid, ester, alkoxy, amide, cyano, ether, silyl ether, phosphine, thioether, disulfide, isothiocyanate, isocyanate, carbonate, ketone, sulfinyl, sulfonyl, carbonothioyl, isonitrile, or any combination of such groups; and n is 1.

In any or all of the above embodiments, $R^1$ is selected from phenyl; —PhC[(R$^c$)$_2$]$_m$PPh$_3$; —Ph[(CH$_2$)$_2$O]$_m$PPh$_3$; —Ph[O(CH$_2$)$_2$]$_m$PPh$_3$; —PhOH; -PhOPPh$_3$; —PhNRPPh$_3$; —Ph[(CH$_2$)$_2$NR]$_m$PPh$_3$, or —Ph[NR(CH$_2$)$_2$]$_m$PPh$_3$, wherein R is hydrogen, aliphatic, aryl, heteroaliphatic, aliphatic-aryl, heteroaryl, aliphatic-heteroaryl, heteroaliphatic-aryl, or heteroaliphatic-heteroaryl; -PhC-aliphatic; -PhN(R)aliphatic wherein R is hydrogen, aliphatic, aryl, heteroaliphatic, aliphatic-aryl, heteroaryl, aliphatic-heteroaryl, heteroaliphatic-aryl, or heteroaliphatic-heteroaryl); or —Ph(Z)$_{1-5}$ wherein Z is Cl, F, Br, or I, NO$_2$, CF$_3$, C(CF$_3$)$_3$; and m is an integer selected from 1 to 30.

In any or all of the above embodiments, $R^1$ is selected from phenyl, —PhOH, —PhOMe, —PhCl, —PhNO$_2$, —PhCF$_3$, —PhC(CF$_3$)$_3$, —PhF$_5$, or —PhNMe$_2$, optionally wherein $R^2$ is selected from alkyl or phenyl.

In any or all of the above embodiments, $R^2$ is selected from alkyl or phenyl.

In any or all of the above embodiments, each of $R^2$, $R^3$, and $R^4$ independently comprises a linker-X group, wherein the linker is selected from a carbonyl-containing group, an alkylene oxide, an aliphatic group, an imidoester; or the linker is generated from a maleimide, a haloacetyl, or a pyridyl disulfide; and wherein X is a moiety that includes functional groups suitable to facilitate delivery of the compound to a target.

In any or all of the above embodiments, the linker-X group is selected from —C(O)R$^c$X, —C[(R$^c$)$_2$]$_m$X, —[(CH$_2$)$_2$O]$_m$X, —O(CH$_2$)$_m$X, —[O(CH$_2$)$_2$]$_m$X, —NR$^c$(CH$_2$)$_m$X, —[(CH$_2$)$_2$NR$^c$]$_m$X, —[NR$^c$(CH$_2$)$_2$]$_m$X, —C(=NH$_2$$^+$)NR$^c$X, —CH$_2$C(O)NHR$^c$X, —SR$^c$X, or

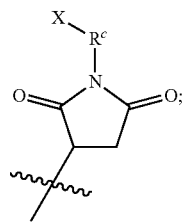

wherein each R$^c$ independently is selected from aliphatic, aryl, heteroaliphatic, aliphatic-aryl, heteroaryl, aliphatic-heteroaryl, heteroaliphatic-aryl, or heteroaliphatic-heteroaryl; each X independently is selected from —P$^+$(R$^d$)$_3$ or —N$^+$(R$^d$)$_3$, wherein each R$^d$ independently is selected from hydrogen, aliphatic, aryl, heteroaliphatic, aliphatic-aryl, heteroaryl, aliphatic-heteroaryl, heteroaliphatic-aryl, or heteroaliphatic-heteroaryl; and each m independently is an integer selected from 1 to 30.

In any or all of the above embodiments, the linker-X group is selected from —C(O)(CH$_2$)$_{1-30}$P$^+$Ph$_3$·Br$^-$, —C(=NH$_2$$^+$)N(CH$_2$)$_{1-30}$P$^+$Ph$_3$·Br$^-$, —CH$_2$C(O)NH(CH$_2$)$_{1-30}$P$^+$Ph$_3$·Br$^-$, —S(CH$_2$)$_{1-30}$P$^+$Ph$_3$·Br$^-$, —(CH$_2$)$_{1-30}$P$^+$Ph$_3$·Br$^-$, —O(CH$_2$)$_{1-30}$P$^+$Ph$_3$·Br$^-$, —NH(CH$_2$)$_{1-30}$P$^+$Ph$_3$·Br$^-$, —C(O)[O(CH$_2$)$_2$]$_{1-30}$P$^+$Ph$_3$·Br$^-$, —C(=NH$_2$$^+$)NCH$_2$[O(CH$_2$)$_2$]$_{1-30}$P$^+$Ph$_3$·Br$^-$, —CH$_2$C(O)NH[O(CH$_2$)$_2$]$_{1-30}$P$^+$Ph$_3$·Br$^-$, —[O(CH$_2$)$_2$]$_{1-30}$P$^+$Ph$_3$·Br$^-$, —C(O)(CH$_2$)$_{1-30}$N$^+$Me$_3$·Br$^-$, —C(=NH$_2$$^+$)N(CH$_2$)$_{1-30}$N$^+$Me$_3$·Br$^-$, —CH$_2$C(O)NH(CH$_2$)$_{1-30}$N$^+$Me$_3$·Br$^-$, —S(CH$_2$)$_{1-30}$N$^+$Me$_3$·Br$^-$, —(CH$_2$)$_{1-30}$N$^+$Me$_3$·Br$^-$, —O(CH$_2$)$_{1-30}$N$^+$Me$_3$·Br$^-$, —NH(CH$_2$)$_{1-30}$N$^+$Me$_3$·Br$^-$, —C(O)[O(CH$_2$)$_2$]$_{1-30}$N$^+$Me$_3$·Br$^-$, —C(=NH$_2$$^+$)NCH$_2$[O(CH$_2$)$_2$]$_{1-30}$N$^+$Me$_3$·Br$^-$, —CH$_2$C(O)NH[O(CH$_2$)$_2$]$_{1-30}$N$^+$Me$_3$·Br$^-$, —S[O(CH$_2$)$_2$]$_{1-30}$N$^+$Me$_3$·Br$^-$,

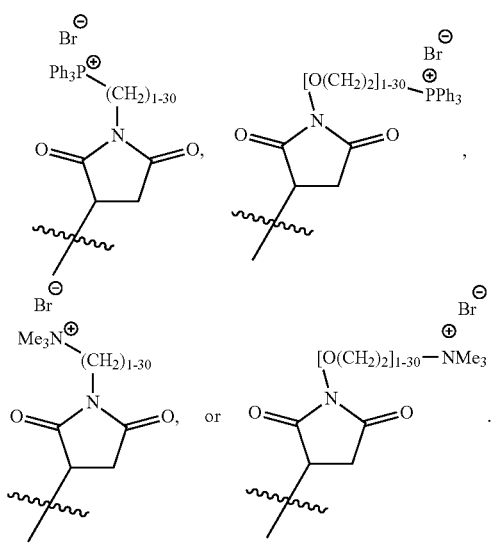

In any or all of the above embodiments, each of R$^3$ and R$^4$ independently is selected from —N(H)linker-X, —N[(CH$_2$)$_n$CH$_3$]linker-X, or —N[(CH$_2$)$_n$CF$_3$]linker-X, wherein the linker is selected from a carbonyl-containing group, an alkylene oxide, an aliphatic group, an imidoester; or the linker is generated from a maleimide, a haloacetyl, or a pyridyl disulfide; and wherein X is a targeting moiety.

In any or all of the above embodiments, each of R$^3$ and R$^4$ independently is selected from —NH$_2$, —N(H)(CH$_2$)$_n$CH$_3$, —N(H)(CH$_2$)$_n$CF$_3$, —N[(CH$_2$)$_n$CH$_3$]$_2$, or —N[(CH$_2$)$_n$CF$_3$]$_2$, wherein each n independently is an integer selected from 0 to 10.

In any or all of the above embodiments, each of R$^3$ and R$^4$ is —N(H)(CH$_2$)$_2$CF$_3$, optionally wherein R$^3$ and R$^4$ is —N[(CH$_2$)$_2$CH$_3$]$_2$ and/or each of R$^1$ and R$^2$ is phenyl.

In any or all of the above embodiments, each of R$^3$ and R$^4$ is —N[(CH$_2$)$_2$CH$_3$]$_2$.

In any or all of the above embodiments, each of R$^1$ and R$^2$ is phenyl.

In any or all of the above embodiments, the compound is selected from any of the species disclosed herein, such as any one of the compounds of Table 3 and/or Table 4.

Also disclosed herein are embodiments of a pharmaceutical formulation or a dosage form, comprising a compound as disclosed herein; and a delivery component, optionally selected from a transdermal patch, a tablet, a capsule, a lotion, or an injectable solution, wherein less than 15% of a total amount of the compound crystalizes when combined the delivery component.

In some embodiments, the delivery component is a transdermal patch, a tablet, a capsule, a lotion, or an injectable solution.

In any or all of the above embodiments, the pharmaceutical formulation or dosage form further comprises an adjuvant, a therapeutic agent, a pharmaceutically acceptable excipient, or any combination thereof.

Also disclosed herein are embodiments of a method, comprising administering to a subject or a sample a therapeutic amount of a compound disclosed herein and/or a compound for use in a method of treating a subject, wherein the compound is a compound according to any or all of the above embodiments, or a pharmaceutical composition thereof.

In some embodiments, at least one additional therapeutic agent is administered sequentially or simultaneously with the compound.

In any or all of the above embodiments, the at least one additional therapeutic agent is edaravone or riluzole.

In any or all of the above embodiments, the subject is a human or a canine.

In any or all of the above embodiments, the compound is administered prophylactically.

In any or all of the above embodiments, the therapeutic amount ranges from greater than 0 mg/day to 100 mg/day.

In any or all of the above embodiments, the subject carries one or more mutations to a superoxide dismutase gene. In some embodiments, the mutation is not or is other than a mutation at a G85, H46, or H48 residue of the superoxide dismutase gene.

In any or all of the above embodiments, the subject is a canine and the canine belongs to a breed susceptible to canine degenerative myelopathy.

In any or all of the above embodiments, the subject has or is at risk of developing a neurological disease selected from ALS, Parkinson's disease, Menkes disease, Lou Gehrig's disease, primary lateral sclerosis, Kennedy's syndrome, frontal temporal dementia associated with ALS, spinal muscular atrophy, and canine degenerative myelopathy; a copper deficiency-based disease; or mitochondrial deficiency Also disclosed herein are embodiments of a method for treating a motor neuron disease, comprising administering to a subject a therapeutic amount of a compound selected from one or more of the compounds below; or a compound for use in a method for treating a motor neuron disease, wherein the compound is selected from one or more of the compounds below:

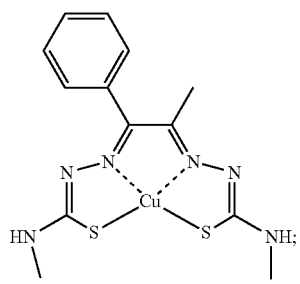

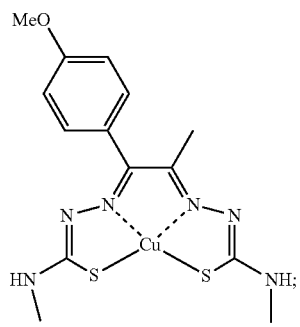

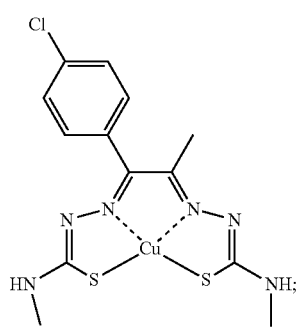

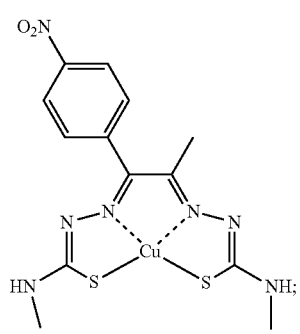

-continued

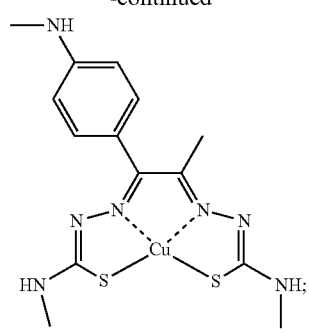

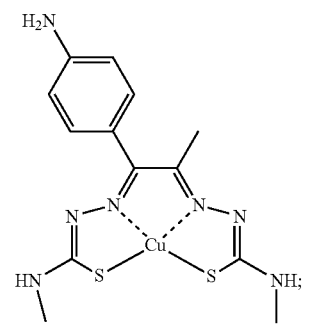

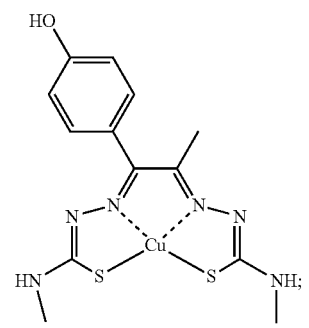

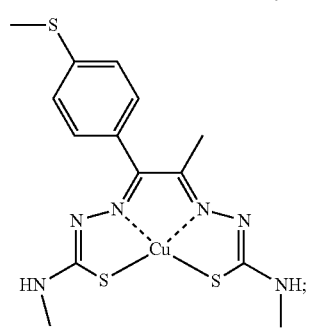

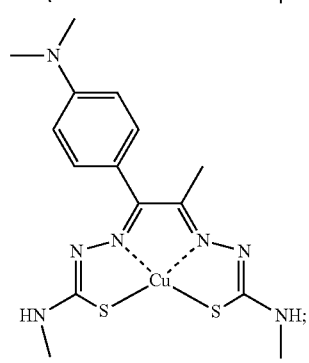

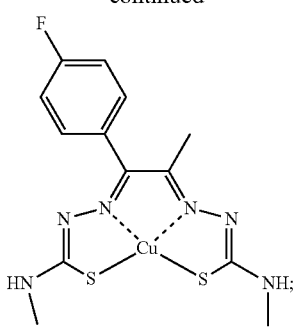

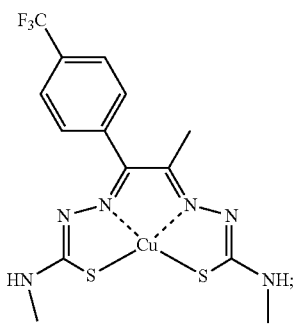

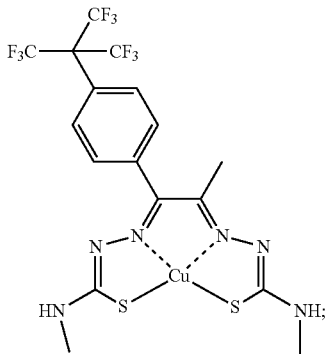

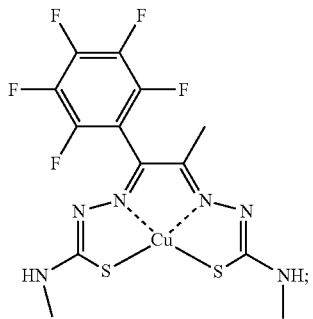

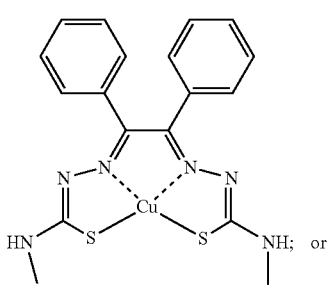 or

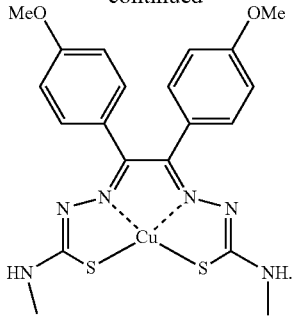

In some embodiments, the therapeutic amount ranges from, or the compound is administered in an amount ranging from, greater than 0 mg/day to 100 mg/day.

In any or all of the above embodiments, the therapeutic amount is a loading dosage ranging from, or the compound is administered in an amount ranging from, 10 mg/day to 100 mg/day.

In any or all of the above embodiments, the method further comprises administering a maintenance dosage of the compound ranging from, or the compound is administered in an amount ranging from, 1 mg/day to 50 mg/day.

In any or all of the above embodiments, the motor neuron disease is selected from ALS, Lou Gehrig's disease, primary lateral sclerosis, Kennedy's syndrome, frontal temporal dementia associated with ALS, spinal muscular atrophy, or any combination thereof.

Also disclosed herein are embodiments of a compound for use in a method for treating a neurological disease, a copper deficiency-based disease, or mitochondrial deficiency, wherein the compound has a structure satisfying Formula I and wherein the variables of Formula I are as described herein.

In some embodiments, the neurological disease is a motor neuron disease.

In any or all of the above embodiments, the neurological disease is selected from ALS, Parkinson's disease, Menkes disease, Lou Gehrig's disease, primary lateral sclerosis, Kennedy's syndrome, frontal temporal dementia associated with ALS, spinal muscular atrophy, and canine degenerative myelopathy.

In any or all of the above embodiments, the method comprises administering a therapeutic amount of the compound to a subject suffering from or predisposed to suffer from the neurological disease. In some embodiments, the subject carries one or more mutations to a superoxide dismutase gene.

In any or all of the above embodiments, the therapeutic amount is a prophylactic dosage ranging from 0.1 mg/day to 30 mg/day.

In any or all of the above embodiments, the prophylactic dosage is administered to a subject that carries one or more mutations to a superoxide dismutase gene. In some embodiments, the mutation is not or is other than a mutation at a G85, H46, or H48 residue of the superoxide dismutase gene.

In any or all of the above embodiments, the prophylactic dosage is administered to a canine that belongs to a breed susceptible to canine degenerative myelopathy.

Also disclosed herein are embodiments of a method, comprising administering a compound disclosed herein, wherein M is $^{60}Cu^{2+}$, $^{61}Cu^{2+}$, $^{62}Cu^{2+}$, $^{63}Cu^{2+}$, $^{64}Cu^{2+}$, or $^{65}Cu^{2+}$, to a subject or a sample and/or a composition comprising any or all of the above compound embodiments for use in a method of diagnosing a subject having or at risk of developing a motor neuron disease, wherein M is $^{60}Cu^{2+}$, $^{61}Cu^{2+}$, $^{62}Cu^{2+}$, $^{63}Cu^{2+}$, $^{64}Cu^{2+}$, or $^{65}Cu^{2+}$.

In some embodiments, the method further comprises imaging the subject or the sample using positron emission tomography to determine the presence of a motor neuron disease.

In any or all of the above embodiments, the method comprises imaging the subject or the sample using positron emission tomography to determine the presence of Parkinson's disease, multiple sclerosis, and Alzheimer's disease.

In any or all of the above embodiments, the method comprises imaging the subject or a sample obtained from a subject using positron emission tomography to determine if the subject has or is at risk of developing a motor neuron disease In view of the many possible embodiments to which the principles of the present disclosure may be applied, it should be recognized that the illustrated embodiments are only preferred examples and should not be taken as limiting the scope of the present disclosure. Rather, the scope is defined by the following claims. We therefore claim as our invention all that comes within the scope and spirit of these claims.

We claim:

1. A method of treating a motor neuron disease and/or a neurological disease, comprising administering (i) a compound having a structure according to Formula A or (ii) a dosage form containing the compound to a subject in need thereof,

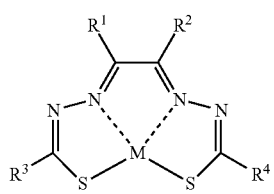

Formula A wherein
M is copper or a radioactive isotope thereof;
$R^1$ is aryl-$(R^5)_n$ or heteroaryl-$(R^5)_n$;
$R^2$ is selected from aryl, aryl-$(R^6)_n$, or $CH_3$;
each of $R^5$ and $R^6$ independently is selected from alkoxy, amine, hydroxyl, nitro, halogen, $C(CF_3)_3$, or $CF_3$;
n is an integer ranging from 1 to 10; and
each of $R^3$ and $R^4$ independently is selected from —N(H)$(CH_2)_{n'}CH_3$, —N(H)$(CH_2)_{n'}CF_3$, —N $[(CH_2)_{n'}CH_3]_2$, or —N$[(CH_2)_{n'}CF_3]_2$, wherein each n' independently is an integer selected from 0 to 9,
wherein the motor neuron disease and/or a neurological disease is amyotrophic lateral sclerosis (ALS), Parkinson's disease, Menkes disease, Lou Gehrig's disease, primary lateral sclerosis, Kennedy's syndrome, frontal temporal dementia associated with ALS, spinal muscular atrophy, or canine degenerative myelopathy.

2. The method of claim 1, further comprising administering edaravone or riluzole sequentially or simultaneously with the compound or the dosage form.

3. The method of claim 1, wherein the subject is a human that carries one or more mutations to a superoxide dismutase gene and the mutation is not or is other than a mutation at a G85, H46, or H48 residue of the superoxide dismutase gene; or wherein the subject is a canine and the canine belongs to a breed susceptible to canine degenerative myelopathy.

4. The method of claim 1, wherein the compound is administered in a loading dosage ranging from 10 mg/day to 100 mg/day.

5. The method of claim 1, wherein the compound is administered in a maintenance dosage ranging from 1 mg/day to 50 mg/day.

6. The method of claim 1, wherein the compound has a structure satisfying one or more of Formulas IIA-IIR:

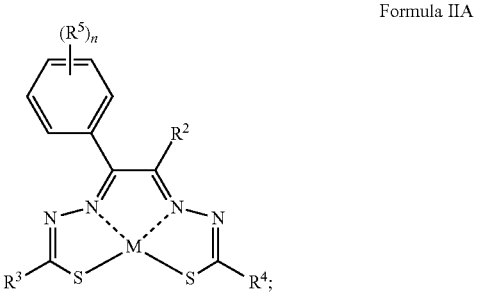

Formula IIA

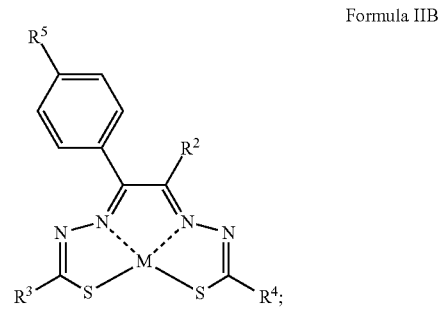

Formula IIB

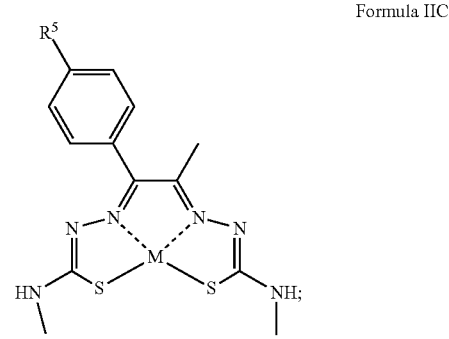

Formula IIC

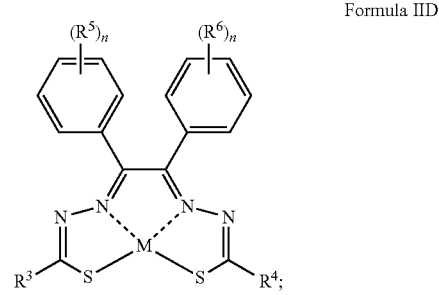

Formula IID

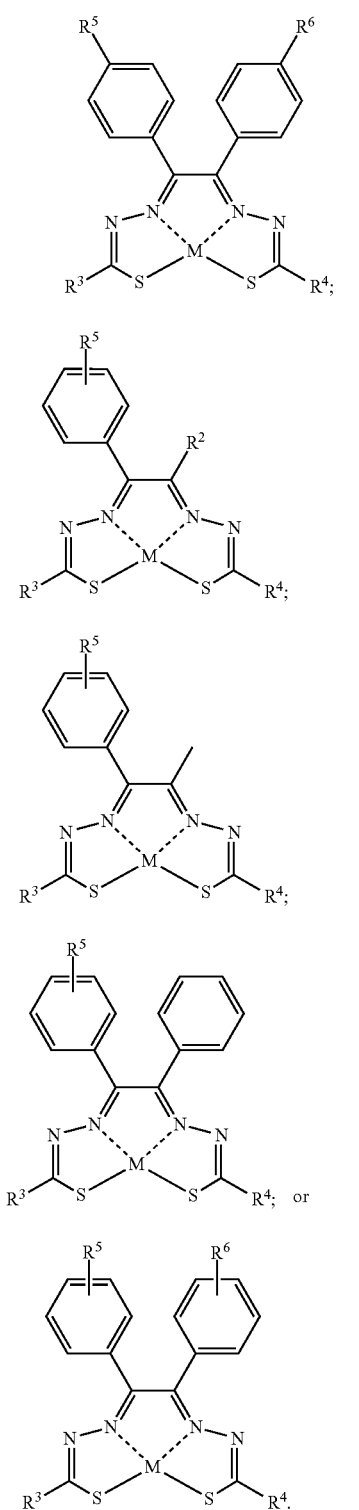
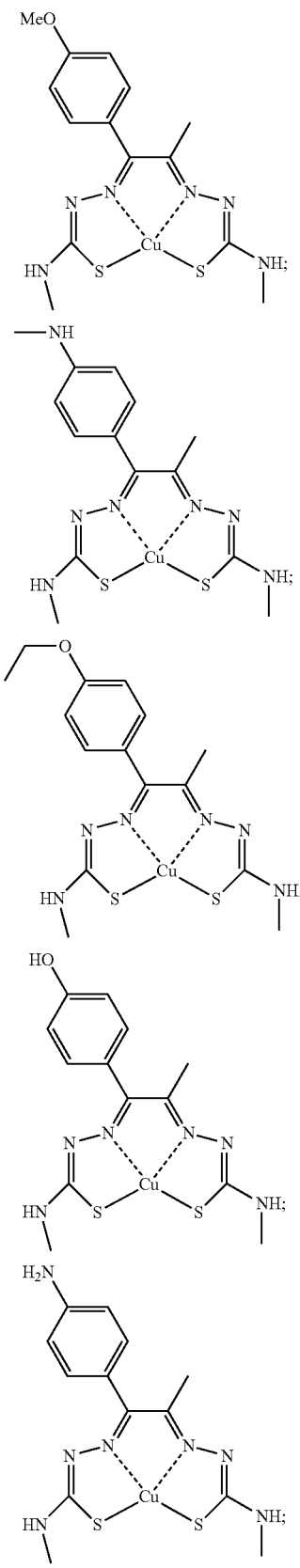
7. The method of claim 1, wherein M is Cu, $Cu^{2+}$, $^{60}Cu^{2+}$, $^{61}Cu^{2+}$, $^{62}Cu^{2+}$, $^{63}Cu^{2+}$, $^{64}Cu^{2+}$, or $^{65}Cu^{2+}$.
8. The method of claim 1, wherein each of $R^3$ and $R^4$ is —N(H)(CH$_2$)$_2$CF$_3$ or —N[(CH$_2$)$_2$CH$_3$]$_2$.
9. The method of claim 1, wherein the compound is selected from 137
-continued
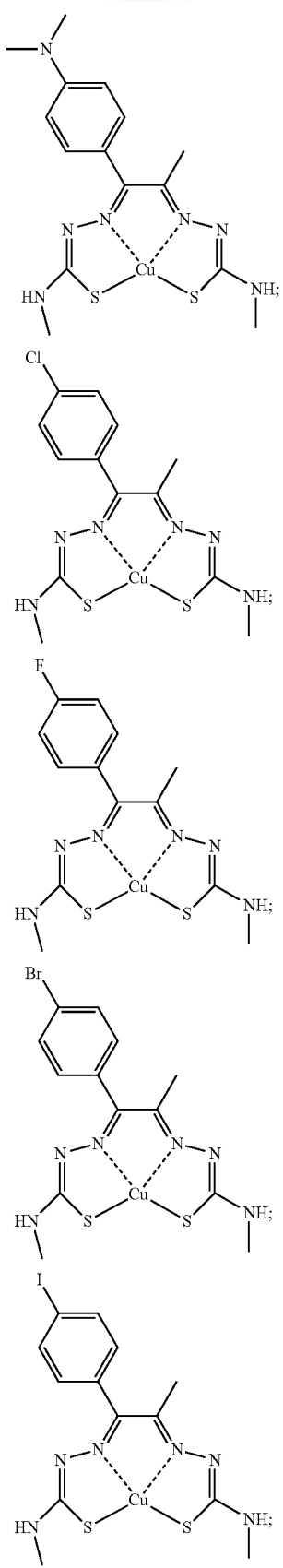
138
-continued
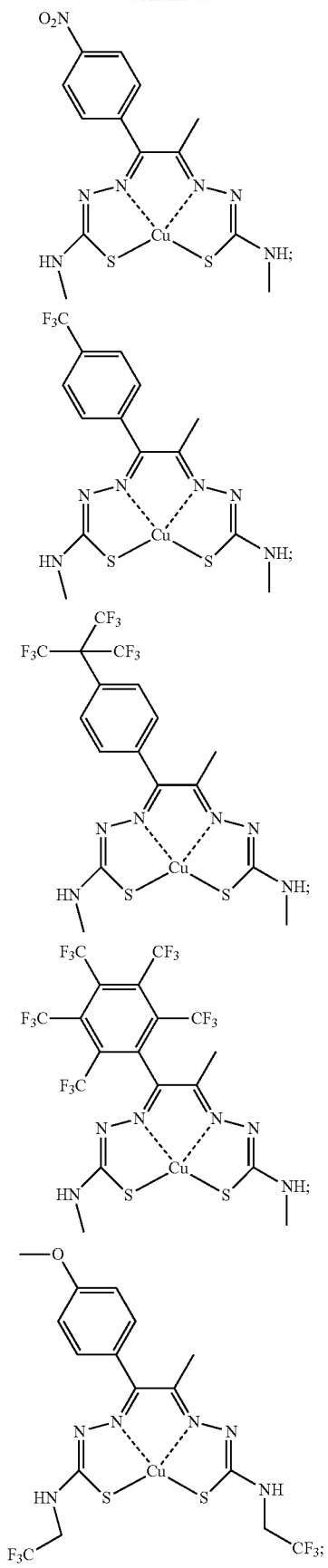

-continued
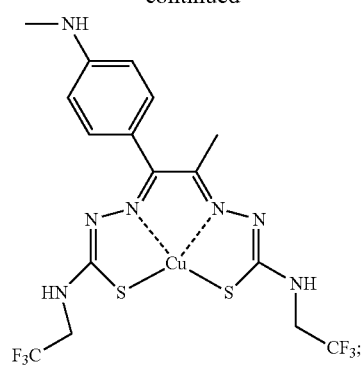
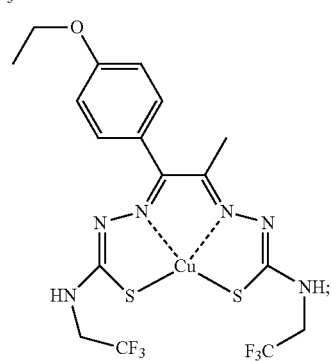
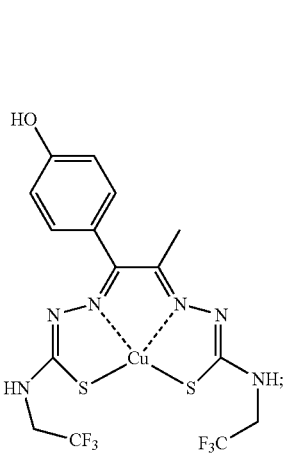
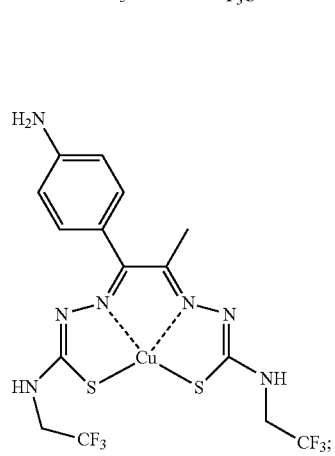
-continued
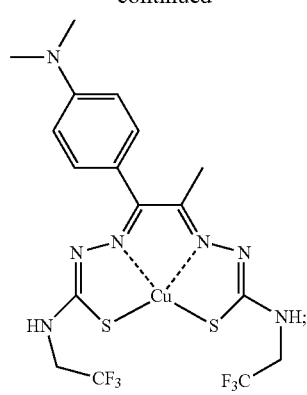
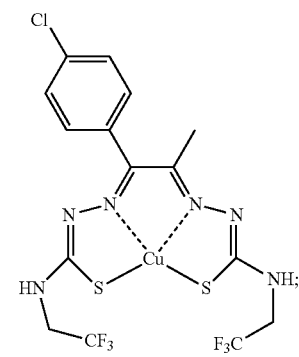
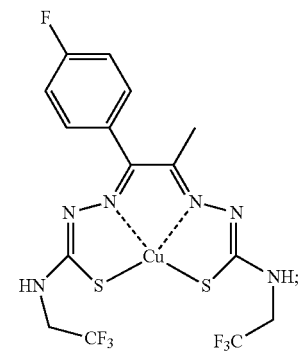
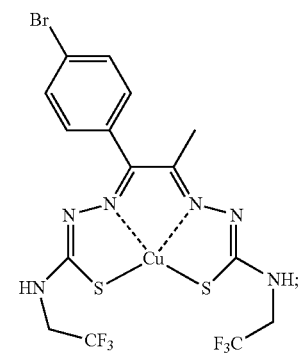

141
-continued
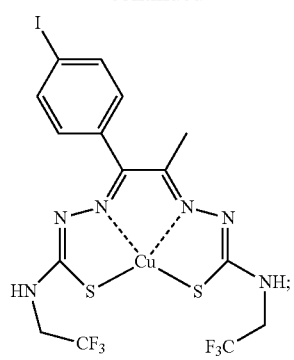
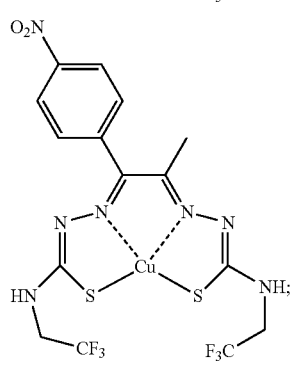
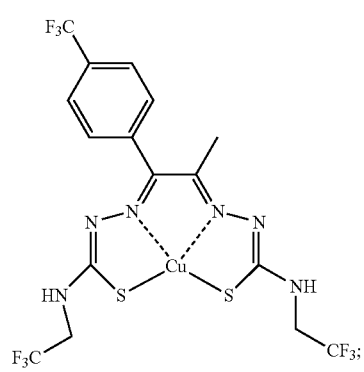
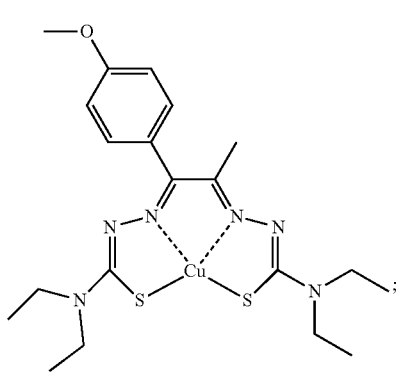
142
-continued
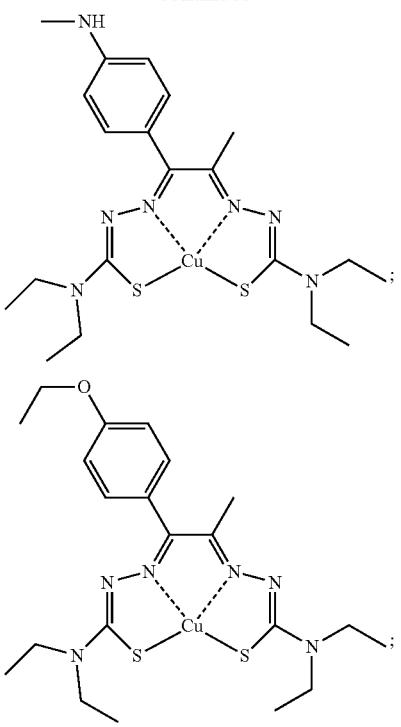
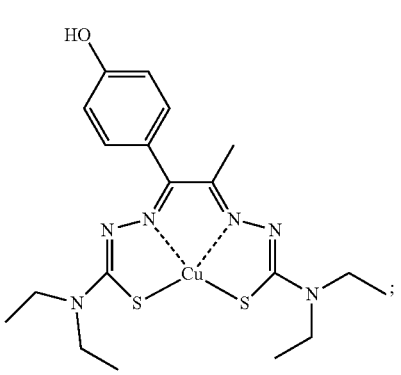
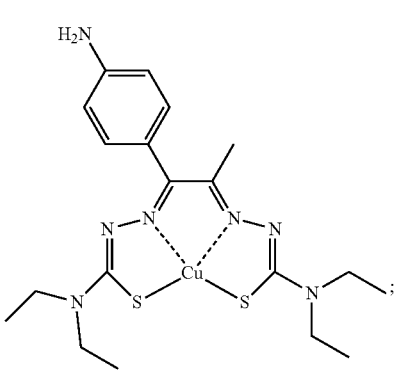

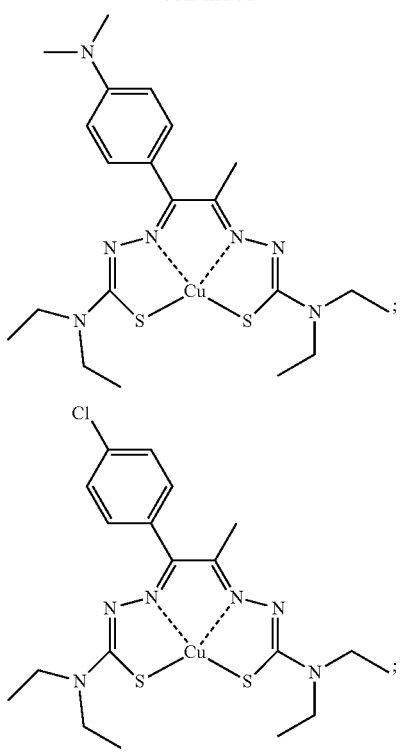
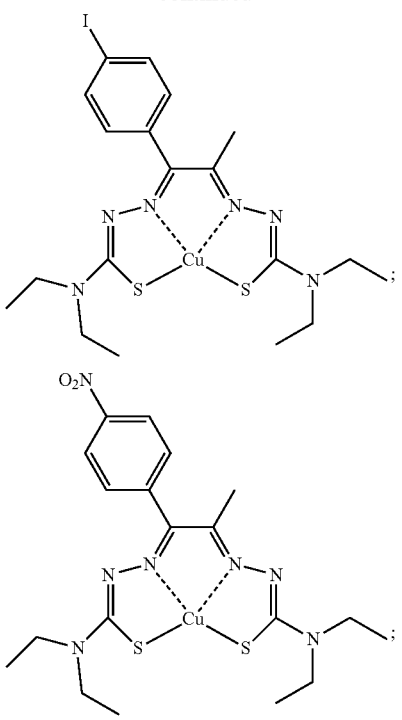
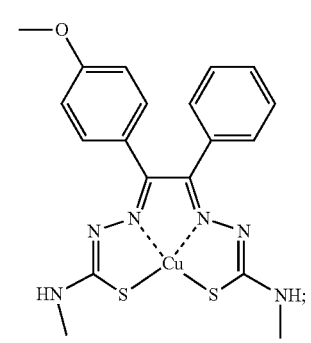

-continued
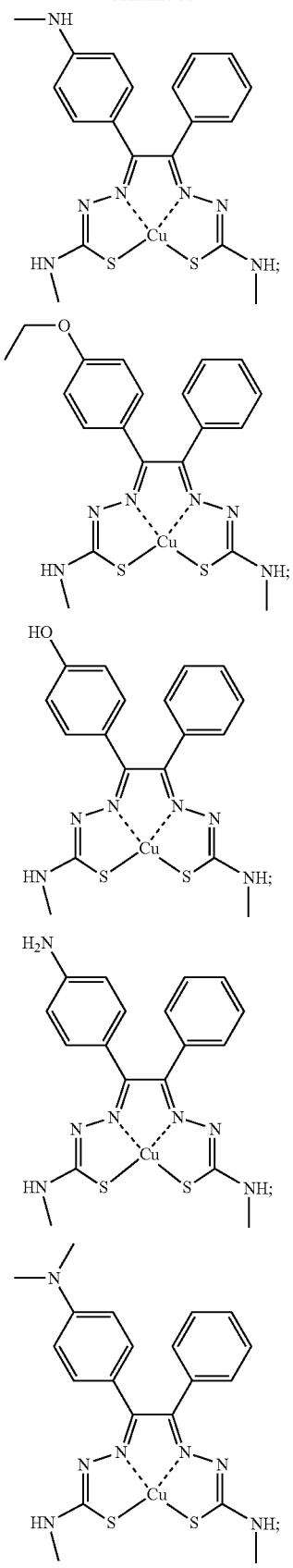
-continued
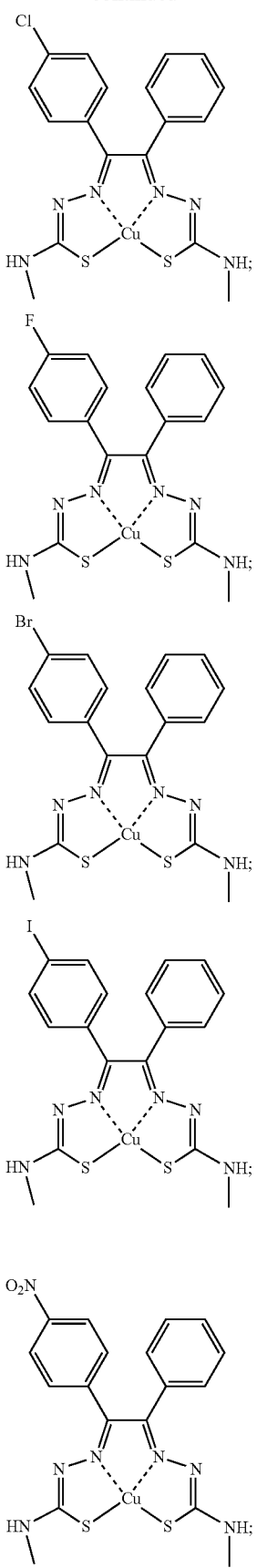

147
-continued
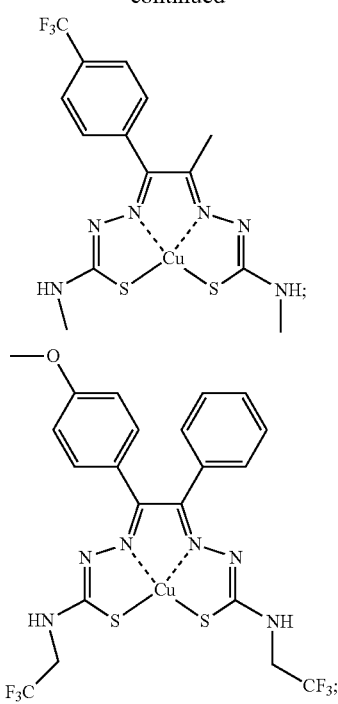
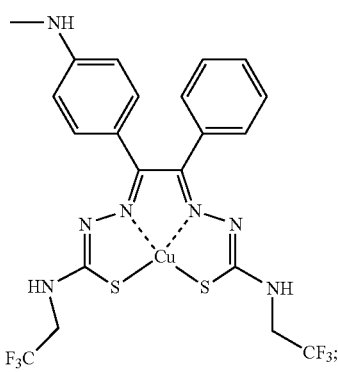
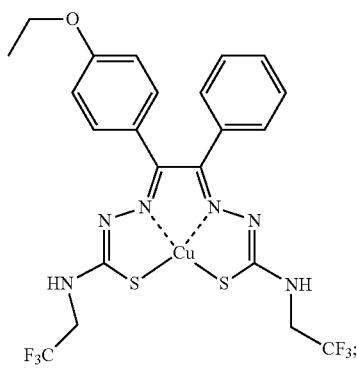
148
-continued
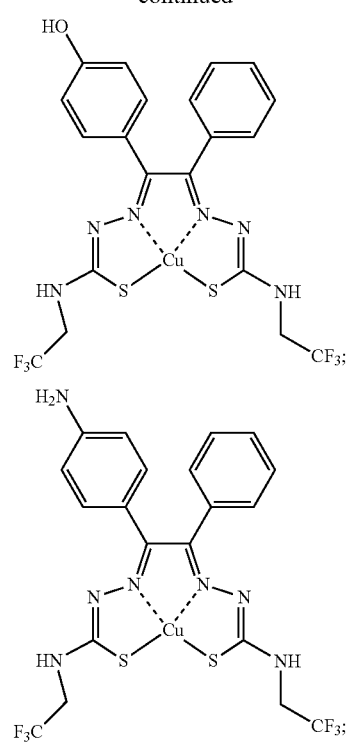
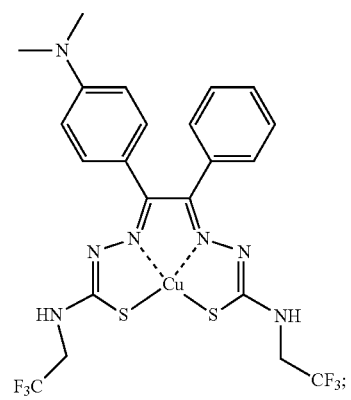
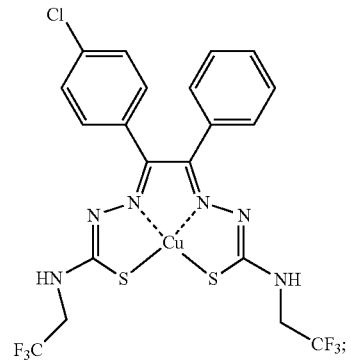

| 149 -continued | 150 -continued |
|---|---|
| 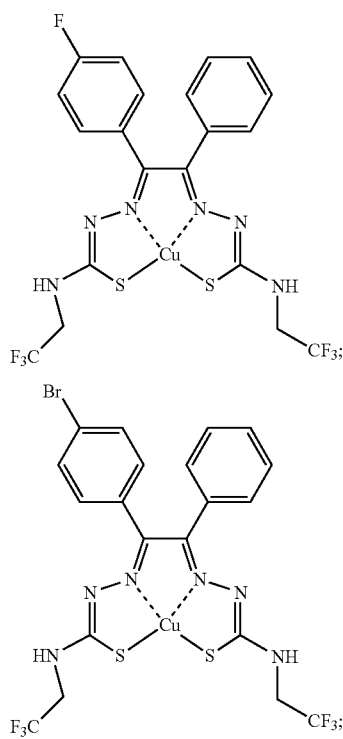 | 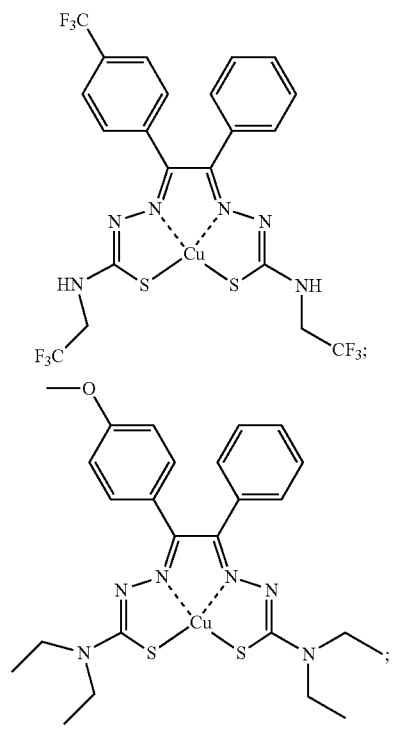 |
| 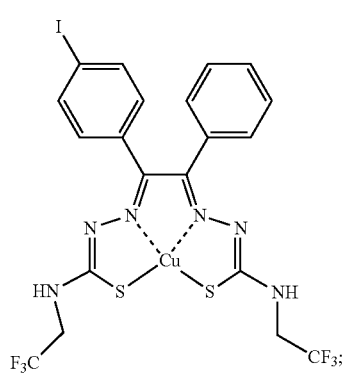 | 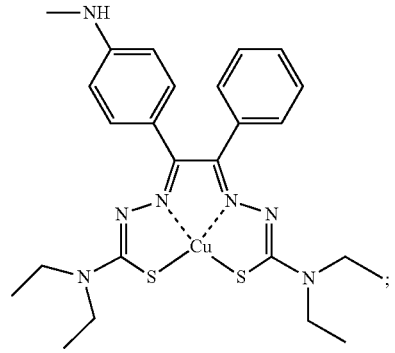 |
| 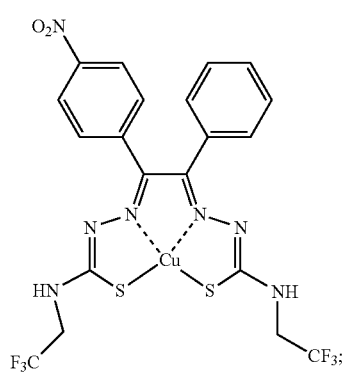 | 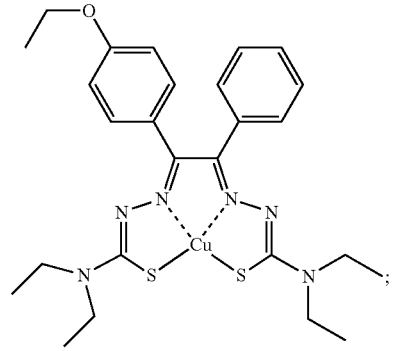 |

151
-continued
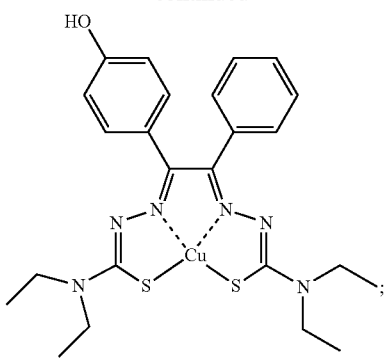
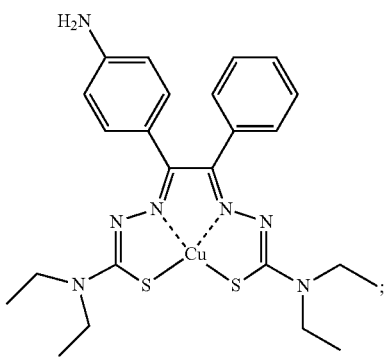
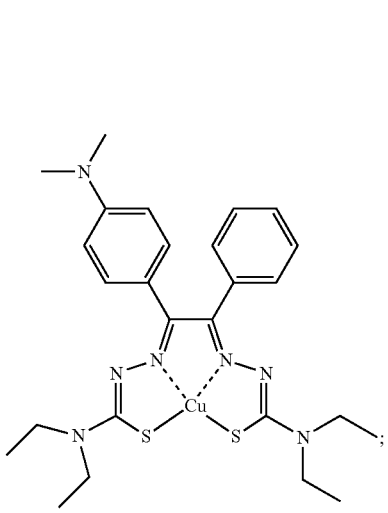
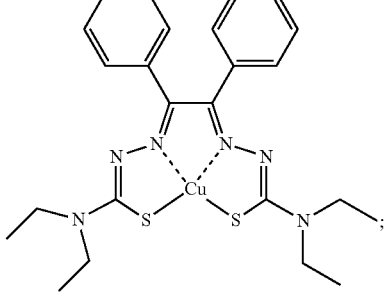
152
-continued
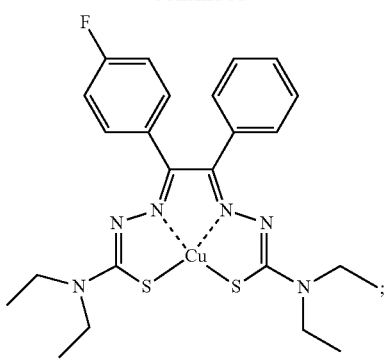
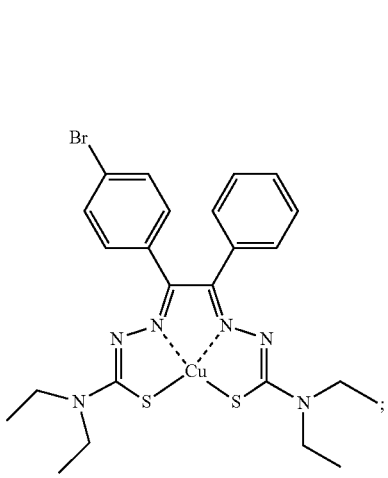
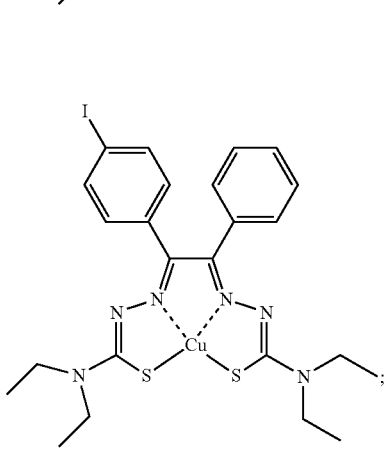
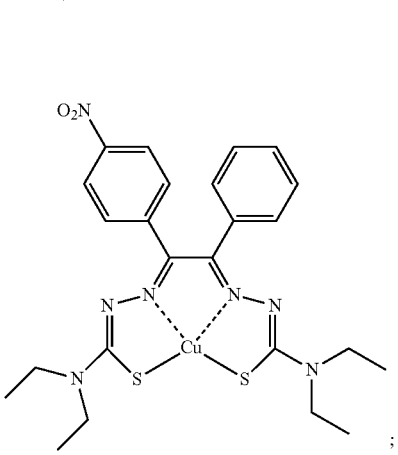

-continued

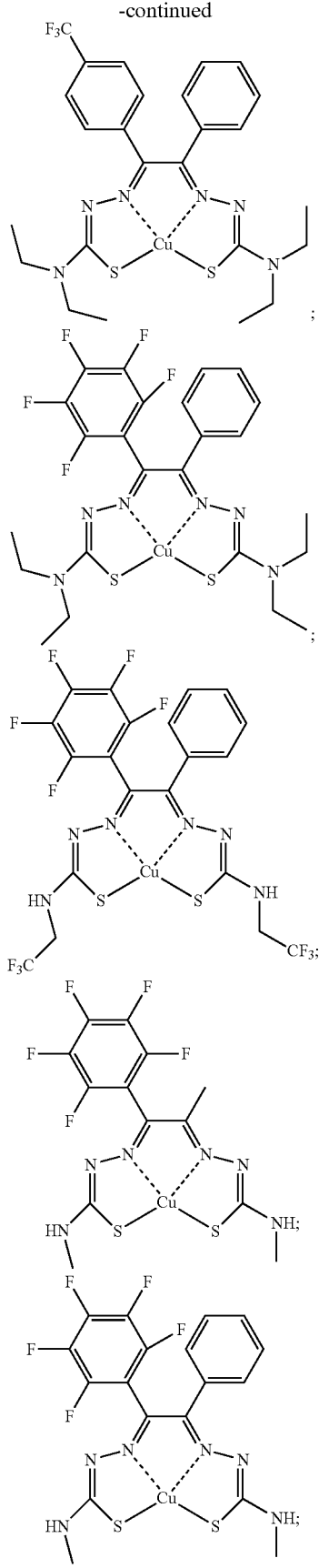

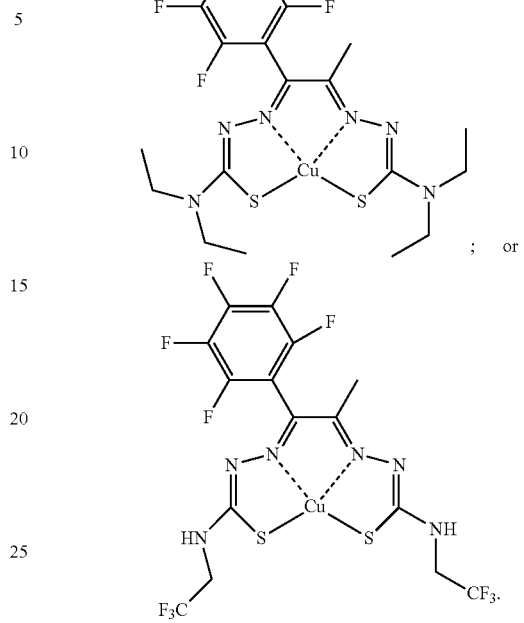

10. The method of claim 1, wherein the subject further suffers from a copper deficiency-based disease or mitochondrial deficiency.

11. The method of claim 1, wherein $R^1$ is selected from pyrimidinyl-$(R^5)_n$, phenyl-$(R^5)_n$, pyridyl-$(R^5)_n$, or naphthyl-$(R^5)_n$.

12. The method of claim 11, wherein each $R^5$ independently is selected from chloro, bromo, fluoro, iodo, or nitro; and n is 1.

13. The method of claim 1, wherein $R^1$ is selected from PhOH; PhOalkyl; —PhN(R)alkyl wherein R is hydrogen or alkyl; or —Ph$(Z)_{1-5}$ wherein each Z independently is Cl, F, Br, I, $NO_2$, $CF_3$, or $C(CF_3)_3$.

14. The method of claim 1, wherein $R^1$ is selected from —PhOH, —PhOMe, —PhCl, —PhNO$_2$, —PhCF$_3$, —PhC(CF$_3$)$_3$, —PhF$_5$, or —PhNMe$_2$; and/or $R^2$ is CH$_3$ or phenyl.

15. A method of treating Parkinson's disease, comprising administering (i) a compound having a structure according to Formula A or (ii) a dosage form containing the compound to a subject in need thereof, Formula A

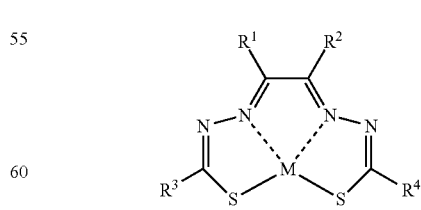

wherein M is Cu; $R^1$ is phenyl; $R^2$ is methyl; and each of $R^3$ and $R^4$ independently is —NHMe.

* * * * *